US012807642B2

(12) United States Patent
Xiao et al.

(10) Patent No.: US 12,807,642 B2
(45) Date of Patent: Nov. 24, 2026

(54) SIZE EXCLUSION CHROMATOGRAPHY FOR CHARACTERIZING HOST CELL PROTEINS

(71) Applicant: Regeneron Pharmaceuticals, Inc., Tarrytown, NY (US)

(72) Inventors: Hui Xiao, Ridgewood, NJ (US); Ning Li, New Canaan, CT (US); Bo Zhao, White Plains, NY (US); Haruna Tomono, Somerville, MA (US); Mengqi Hu, White Plains, NY (US); Rosalynn Molden, Shoreline, WA (US); Yunli Hu, Tarrytown, NY (US); Yu Huang, Ossining, NY (US); Haibo Qiu, Millwood, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 769 days.

(21) Appl. No.: 18/114,047

(22) Filed: Feb. 24, 2023

(65) Prior Publication Data

US 2023/0279046 A1 Sep. 7, 2023

Related U.S. Application Data

(60) Provisional application No. 63/426,221, filed on Nov. 17, 2022, provisional application No. 63/341,381, filed on May 12, 2022, provisional application No. 63/314,144, filed on Feb. 25, 2022.

(51) Int. Cl.

| | |
|---|---|
| ***G01N 33/68*** | (2006.01) |
| ***C07K 1/16*** | (2006.01) |
| ***C07K 1/22*** | (2006.01) |
| ***C07K 1/36*** | (2006.01) |

(52) U.S. Cl.

CPC . *C07K 1/22* (2013.01); *C07K 1/36* (2013.01)

(58) Field of Classification Search

None

See application file for complete search history.

(56) References Cited

U.S. PATENT DOCUMENTS

| | | | | |
|---|---|---|---|---|
| 6,080,398 | A * | 6/2000 | Pelus | A61P 7/00 435/254.11 |
| 2013/0330744 | A1 * | 12/2013 | Da Silva | C07K 14/4716 435/23 |
| 2014/0249072 | A1 * | 9/2014 | Chen | C07K 14/472 514/6.9 |
| 2018/0196051 | A1 * | 7/2018 | Tao | G01N 33/57515 |
| 2019/0169675 | A1 * | 6/2019 | Graham | C12Q 1/37 |
| 2019/0242877 | A1 | 8/2019 | Wang | |
| 2019/0282656 | A1 * | 9/2019 | Mackay | A61K 47/6849 |
| 2020/0333353 | A1 | 10/2020 | Chen | |
| 2021/0239661 | A1 | 8/2021 | Wang | |

OTHER PUBLICATIONS

Yan Yuetian et al., "Versatile, Sensitive, and Robust Navtive LC?MS Platform for Intact Mass Analysis of Protein Drugs," Journal of the American Society for Mass Spectrometry, vol. 31, No. 10, Aug. 31, 2020, pp. 2171-2179.

Pilely Katrine et al., "Monitoring Process-Related Impurities in Biologics-Host Cell Protein Analysis," Analytical and Bioanalytical Chemistry, Springer Berlin Heidelberg, Berlin/Heidelberg, vol. 414, No. 2, Oct. 1, 2021, pp. 747-758.

International Search Report and Written Opinion, International Application No. PCT/US2023/013839, International Filing Date Feb. 24, 2023, Date of Mailing Aug. 7, 2023.

* cited by examiner

*Primary Examiner* — Paul S Hyun

(74) *Attorney, Agent, or Firm* — BakerHostetler

(57) ABSTRACT

The present invention generally pertains to methods of identifying and characterizing host cell proteins. In particular, the present invention pertains to the use of size exclusion chromatography in non-denaturing or denaturing conditions to enrich a sample for host cell proteins and characterize the binding of host cell proteins to a protein of interest.

52 Claims, 62 Drawing Sheets

<table>
<tr><th></th><th colspan="4">Native</th><th colspan="4">Denaturing (20% ACN)</th></tr>
<tr><th></th><th>HMW</th><th>Main</th><th>Tail</th><th>LMW</th><th>HMW</th><th>Main</th><th>Tail</th><th>LMW</th></tr>
<tr><td>>tr|G3HCV4|G3HCV4_CRIGR Alpha-mannosidase</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3GZB2|G3GZB2_CRIGR Acid ceramidase</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3GYY6|G3GYY6_CRIGR Catalase</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3HIM1|G3HIM1_CRIGR Basement membrane-specific heparan sulfate proteoglycan core protein</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3H928|G3H928_CRIGR Adenylate kinase 2, mitochondrial</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3HF46|G3HF46_CRIGR Polypyrimidine tract-binding protein 1</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3GX17|G3GX17_CRIGR Polypeptide N-acetylgalactosaminyltransferase</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3IKH3|G3IKH3_CRIGR Collagen alpha-2(V) chain</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3H7I6|G3H7I6_CRIGR Sulfhydryl oxidase</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3H2P3|G3H2P3_CRIGR Beta-galactosidase (Fragment)</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3I2T9|G3I2T9_CRIGR 3-phosphoinositide-dependent protein kinase 1</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3IKH4|G3IKH4_CRIGR Collagen alpha-2(V) chain</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3IA26|G3IA26_CRIGR Heparanase</td><td>100.0%</td><td>0.0%</td><td>0.0%</td><td>0.0%</td><td>100.0%</td><td>0.0%</td><td>0.0%</td><td>0.0%</td></tr>
<tr><td>>tr|G3HRF8|G3HRF8_CRIGR CD166 antigen</td><td>100.0%</td><td>0.0%</td><td>0.0%</td><td>0.0%</td><td>100.0%</td><td>0.0%</td><td>0.0%</td><td>0.0%</td></tr>
</table>

FIG. 18A

| | Native | | | | Denaturing (20% ACN) | | | |
|---|---|---|---|---|---|---|---|---|
| | HMW | Main | Tail | LMW | HMW | Main | Tail | LMW |
| >tr\|G3I1R6\|G3I1R6_CRIGR Epididymal secretory protein E3-beta | 0.0% | 0.0% | 42.9% | 57.1% | 0.0% | 0.0% | 60.0% | 40.0% |
| >tr\|G3HD51\|G3HD51_CRIGR LisH domain and HEAT repeat-containing protein KIAA1468 | 0.0% | 0.0% | 0.0% | 100.0% | 0.0% | 0.0% | 47.0% | 53.0% |
| >tr\|G3H3C3\|G3H3C3_CRIGR Serine/threonine-protein kinase Nek1 | 0.0% | 0.0% | 44.4% | 55.6% | 0.0% | 0.0% | 42.9% | 57.1% |
| >tr\|G3I234\|G3I234_CRIGR Protein FAM55A (Fragment) | 0.0% | 0.0% | 42.9% | 57.1% | 0.0% | 0.0% | 41.2% | 58.8% |
| >tr\|G3IQ82\|G3IQ82_CRIGR Uncharacterized protein KIAA1267 | 0.0% | 0.0% | 0.0% | 100.0% | 0.0% | 0.0% | 33.3% | 66.7% |
| >tr\|G3I5K8\|G3I5K8_CRIGR Carboxylic ester hydrolase | 0.0% | 0.0% | 100.0% | 0.0% | 0.0% | 0.0% | 16.7% | 83.3% |
| >tr\|G3HXI5\|G3HXI5_CRIGR Peptidylprolyl isomerase domain and WD repeat-containing protein 1 | 0.0% | 0.0% | 20.0% | 80.0% | 0.0% | 0.0% | 0.0% | 100.0% |
| >P61626ups\|LYSC_HUMAN_UPS Lysozyme C (Chain 19-148) | 0.0% | 0.0% | 0.0% | 100.0% | 0.0% | 0.0% | 0.0% | 100.0% |
| >tr\|G3GVD0\|G3GVD0_CRIGR ACTB | 0.0% | 0.0% | 0.0% | 100.0% | 0.0% | 0.0% | 0.0% | 100.0% |
| >tr\|G3HH92\|G3HH92_CRIGR Pirin | 0.0% | 0.0% | 0.0% | 100.0% | 0.0% | 0.0% | 0.0% | 100.0% |
| >tr\|G3HNJ3\|G3HNJ3_CRIGR Clusterin | 0.0% | 0.0% | 0.0% | 100.0% | 0.0% | 0.0% | 0.0% | 100.0% |
| >tr\|G3HCH0\|G3HCH0_CRIGR MYDGF | 0.0% | 0.0% | 0.0% | 100.0% | 0.0% | 0.0% | 0.0% | 100.0% |
| >tr\|G3GU60\|G3GU60_CRIGR Phosphatidylethanolamine-binding protein 1 | 0.0% | 0.0% | 0.0% | 100.0% | 0.0% | 0.0% | 0.0% | 100.0% |
| >tr\|G3H0U6\|G3H0U6_CRIGR Protein disulfide-isomerase A3 | 0.0% | 0.0% | 0.0% | 100.0% | 0.0% | 0.0% | 0.0% | 100.0% |
| >tr\|G3H1D5\|G3H1D5_CRIGR Carboxypeptidase | 0.0% | 0.0% | 0.0% | 100.0% | 0.0% | 0.0% | 0.0% | 100.0% |
| >tr\|G3I973\|G3I973_CRIGR Hypoxia up-regulated protein 1 | 0.0% | 0.0% | 0.0% | 100.0% | 0.0% | 0.0% | 0.0% | 100.0% |
| >tr\|G3HKD0\|G3HKD0_CRIGR Peptidyl-prolyl cis-trans isomerase | 0.0% | 0.0% | 0.0% | 100.0% | 0.0% | 0.0% | 0.0% | 100.0% |
| >tr\|G3I278\|G3I278_CRIGR Laminin subunit beta-1 | 0.0% | 0.0% | 0.0% | 100.0% | 0.0% | 0.0% | 0.0% | 100.0% |
| >tr\|G3IE06\|G3IE06_CRIGR Transmembrane protein 132A | 0.0% | 0.0% | 0.0% | 100.0% | 0.0% | 0.0% | 0.0% | 100.0% |
| >tr\|G3IBK2\|G3IBK2_CRIGR Filamin-A | 0.0% | 0.0% | 0.0% | 100.0% | 0.0% | 0.0% | 0.0% | 100.0% |
| >tr\|G3HIQ0\|G3HIQ0_CRIGR Threonyl-tRNA synthetase, cytoplasmic | 0.0% | 0.0% | 0.0% | 100.0% | 0.0% | 0.0% | 0.0% | 100.0% |
| >tr\|G3I018\|G3I018_CRIGR 26S proteasome non-ATPase regulatory subunit 7 | 0.0% | 0.0% | 0.0% | 100.0% | 0.0% | 0.0% | 0.0% | 100.0% |
| >tr\|G3IDD9\|G3IDD9_CRIGR 40S ribosomal protein S3 | 0.0% | 0.0% | 0.0% | 100.0% | 0.0% | 0.0% | 0.0% | 100.0% |

FIG. 18B

| | Native | | | | Denaturing (20% ACN) | | | |
|---|---|---|---|---|---|---|---|---|
| | HMW | Main | Tail | LMW | HMW | Main | Tail | LMW |
| >tr\|G3IN86\|G3IN86_CRIGR DPP7 | 100.0% | 0.0% | 0.0% | 0.0% | 87.5% | 0.0% | 12.5% | 0.0% |
| >tr\|G3I255\|G3I255_CRIGR L-lactate dehydrogenase | 97.1% | 0.0% | 2.9% | 0.0% | 91.7% | 0.0% | 8.3% | 0.0% |
| >Q06830ups\|PRDX1_HUMAN_UPS Peroxiredoxin 1 (Chain 2-199) | 100.0% | 0.0% | 0.0% | 0.0% | 85.7% | 0.0% | 14.3% | 0.0% |
| >tr\|G3I5L3\|G3I5L3_CRIGR Annexin | 89.3% | 0.0% | 0.0% | 10.7% | 100.0% | 0.0% | 0.0% | 0.0% |
| >tr\|G3IHT7\|G3IHT7_CRIGR Semaphorin-4B | 90.2% | 2.4% | 7.3% | 0.0% | 82.4% | 0.0% | 17.6% | 0.0% |
| >tr\|G3HCL3\|G3HCL3_CRIGR TNFSF9 | 100.0% | 0.0% | 0.0% | 0.0% | 87.5% | 0.0% | 0.0% | 12.5% |
| >tr\|G3HBD3\|G3HBD3_CRIGR Nucleoside diphosphate kinase | 100.0% | 0.0% | 0.0% | 0.0% | 64.3% | 0.0% | 35.7% | 0.0% |
| >tr\|G3GZZ0\|G3GZZ0_CRIGR Aspartate aminotransferase | 100.0% | 0.0% | 0.0% | 0.0% | 63.6% | 0.0% | 36.4% | 0.0% |
| >tr\|G3H8A8\|G3H8A8_CRIGR Mesencephalic astrocyte-derived neurotrophic factor | 100.0% | 0.0% | 0.0% | 0.0% | 42.9% | 57.1% | 0.0% | 0.0% |
| >tr\|G3H5Q0\|G3H5Q0_CRIGR Actin, alpha cardiac muscle 1 | 100.0% | 0.0% | 0.0% | 0.0% | 0.0% | 50.0% | 50.0% | 0.0% |
| >tr\|G3GS79\|G3GS79_CRIGR Zinc finger protein DZIP1 | 100.0% | 0.0% | 0.0% | 0.0% | 72.7% | 0.0% | 0.0% | 27.3% |
| >tr\|G3I7X7\|G3I7X7_CRIGR Carboxylic ester hydrolase | 97.0% | 3.0% | 0.0% | 0.0% | 22.8% | 0.0% | 63.2% | 14.0% |
| >tr\|G3GS89\|G3GS89_CRIGR Uncharacterized protein | 100.0% | 0.0% | 0.0% | 0.0% | 8.3% | 33.3% | 25.0% | 33.3% |
| >tr\|G3GRE1\|G3GRE1_CRIGR Bifunctional aminoacyl-tRNA synthetase (Fragment) | 100.0% | 0.0% | 0.0% | 0.0% | 34.4% | 0.0% | 25.0% | 40.6% |
| >tr\|G3I4W7\|G3I4W7_CRIGR Cathepsin D | 100.0% | 0.0% | 0.0% | 0.0% | 25.0% | 0.0% | 25.0% | 50.0% |
| >tr\|G3HS71\|G3HS71_CRIGR Vasorin | 100.0% | 0.0% | 0.0% | 0.0% | 25.0% | 0.0% | 25.0% | 50.0% |
| >tr\|G3HGW6\|G3HGW6_CRIGR Laminin subunit alpha-5 | 100.0% | 0.0% | 0.0% | 0.0% | 27.6% | 0.0% | 20.7% | 51.7% |
| >tr\|G3GYP9\|G3GYP9_CRIGR Peroxiredoxin | 82.5% | 7.8% | 7.8% | 1.8% | 66.8% | 4.0% | 19.9% | 9.3% |
| >tr\|G3IBH0\|G3IBH0_CRIGR Metalloproteinase inhibitor 1 | 78.8% | 0.0% | 15.2% | 6.1% | 37.9% | 4.2% | 24.2% | 33.7% |

FIG. 18C

| | Native | | | | Denaturing (20% ACN) | | | |
|---|---|---|---|---|---|---|---|---|
| | HMW | Main | Tail | LMW | HMW | Main | Tail | LMW |
| >tr\|G3I5Z5\|G3I5Z5_CRIGR Prostaglandin reductase 1 | 76.8% | 0.0% | 23.2% | 0.0% | 40.0% | 0.0% | 52.5% | 7.5% |
| >tr\|G3GR64\|G3GR64_CRIGR Inter-alpha-trypsin inhibitor heavy chain H5 | 76.1% | 0.0% | 23.9% | 0.0% | 30.3% | 0.0% | 39.4% | 30.3% |
| >tr\|G3IIK9\|G3IIK9_CRIGR Cornifin-A | 100.0% | 0.0% | 0.0% | 0.0% | 13.3% | 0.0% | 6.7% | 80.0% |
| >tr\|G3IKQ6\|G3IKQ6_CRIGR CSTB | 100.0% | 0.0% | 0.0% | 0.0% | 5.6% | 0.0% | 0.0% | 94.4% |
| >tr\|G3H0S7\|GSH0S7_CRIGR Beta-2-microglobulin | 100.0% | 0.0% | 0.0% | 0.0% | 0.0% | 0.0% | 0.0% | 100.0% |
| >tr\|G3I3G8\|G3I3G8_CRIGR Transaldolase | 78.6% | 0.0% | 0.0% | 21.4% | 0.0% | 0.0% | 0.0% | 100.0% |
| >tr\|G3HUU6\|G3HUU6_CRIGR Protein S100 | 66.7% | 0.0% | 0.0% | 33.3% | 0.0% | 0.0% | 0.0% | 100.0% |
| >tr\|G3I4E8\|G3I4E8_CRIGR Fatty acid-binding protein, adipocyte | 55.6% | 22.2% | 0.0% | 22.2% | 5.3% | 0.0% | 0.0% | 94.7% |
| >tr\|G3IDN7\|G3IDN7_CRIGR Protein FAM3C | 35.6% | 0.0% | 0.0% | 64.4% | 4.2% | 0.0% | 0.0% | 95.8% |
| >tr\|G3HH30\|G3HH30_CRIGR Aldose reductase | 64.4% | 0.0% | 0.0% | 35.6% | 15.6% | 0.0% | 0.0% | 84.4% |
| >tr\|G3IEU2\|G3IEU2_CRIGR Protein DJ-1 | 48.1% | 0.0% | 0.0% | 51.9% | 22.2% | 0.0% | 0.0% | 77.8% |
| >tr\|G3I3Y6\|G3I3Y6_CRIGR Glutathione S-transferase P | 47.1% | 0.0% | 2.0% | 51.0% | 8.3% | 0.0% | 1.7% | 90.0% |
| >tr\|G3IDN7\|G3IDN7_CRIGR Protein FAM3C | 35.6% | 0.0% | 0.0% | 64.4% | 4.2% | 0.0% | 0.0% | 95.8% |
| >tr\|G3HAI3\|G3HAI3_CRIGR Follistatin-related protein 1 | 64.3% | 35.7% | 0.0% | 0.0% | 0.0% | 57.9% | 0.0% | 42.1% |
| >tr\|G3I7Y4\|G3I7Y4_CRIGR Ubiquitin-protein ligase E3A (Fragment) | 55.6% | 44.4% | 0.0% | 0.0% | 0.0% | 80.0% | 20.0% | 0.0% |
| >tr\|G3I6T1\|G3I6T1_CRIGR Phospholipase B-like | 53.2% | 22.6% | 11.3% | 12.9% | 8.0% | 11.5% | 19.5% | 61.1% |
| >tr\|G3I5N6\|G3I5N6_CRIGR IGFBP4 | 50.0% | 33.3% | 0.0% | 16.7% | 33.3% | 13.9% | 8.3% | 44.4% |
| >tr\|G3INC5\|G3INC5_CRIGR Cathepsin L1 | 47.3% | 0.0% | 12.7% | 40.0% | 25.6% | 0.0% | 25.6% | 48.8% |
| >tr\|G3GTT2\|G3GTT2_CRIGR C-C motif chemokine | 55.6% | 0.0% | 0.0% | 44.4% | 30.0% | 0.0% | 20.0% | 50.0% |

FIG. 18C
CONTINUED

<table>
<tr><th rowspan="2">Protein Name</th><th colspan="4">Native</th><th colspan="4">Denaturing (20% ACN)</th><th rowspan="2"></th></tr>
<tr><th>HMW</th><th>Main</th><th>Tail</th><th>LMW</th><th>HMW</th><th>Main</th><th>Tail</th><th>LMW</th></tr>
<tr><td>>tr|G3GZB2|G3GZB2_CRIGR Acid ceramidase</td><td>100.0%</td><td>0.0%</td><td>0.0%</td><td>0.0%</td><td>100.0%</td><td>0.0%</td><td>0.0%</td><td>0.0%</td><td>Relatively stronger binding</td></tr>
<tr><td>>tr|G3I7X7|G3I7X7_CRIGR Carboxylic ester hydrolase</td><td>97.0%</td><td>3.0%</td><td>0.0%</td><td>0.0%</td><td>22.8%</td><td>0.0%</td><td>63.2%</td><td>14.0%</td><td rowspan="5">Weak binding<br>Can be interrupted by 20% ACN</td></tr>
<tr><td>>tr|G3I4W7|G3I4W7_CRIGR Cathepsin D</td><td>100.0%</td><td>0.0%</td><td>0.0%</td><td>0.0%</td><td>25.0%</td><td>0.0%</td><td>25.0%</td><td>50.0%</td></tr>
<tr><td>>tr|G3I6T1|G3I6T1_CRIGR Phospholipase B-like</td><td>53.2%</td><td>22.6%</td><td>11.3%</td><td>12.9%</td><td>8.0%</td><td>11.5%</td><td>19.5%</td><td>61.1%</td></tr>
<tr><td>>tr|G3INC5|G3INC5_CRIGR Cathepsin L1</td><td>47.3%</td><td>0.0%</td><td>12.7%</td><td>40.0%</td><td>25.6%</td><td>0.0%</td><td>25.6%</td><td>48.8%</td></tr>
<tr><td>>tr|Q9EPP7|Q9EPP7_CRIGR CTSZ</td><td>22.0%</td><td>0.0%</td><td>6.0%</td><td>72.0%</td><td>8.5%</td><td>0.0%</td><td>8.5%</td><td>83.0%</td></tr>
<tr><td>>tr|G3I7X9|G3I7X9_CRIGR Liver carboxylesterase 1</td><td>18.9%</td><td>0.0%</td><td>29.7%</td><td>51.4%</td><td>17.2%</td><td>0.0%</td><td>37.9%</td><td>44.8%</td><td rowspan="3">Weak binding<br>Not affected by 20% ACN</td></tr>
<tr><td>>tr|G3I7X5|G3I7X5_CRIGR Liver carboxylesterase 4</td><td>12.1%</td><td>0.0%</td><td>48.5%</td><td>39.4%</td><td>17.9%</td><td>0.0%</td><td>33.3%</td><td>48.7%</td></tr>
<tr><td>>tr|G3I5L0|G3I5L0_CRIGR Liver carboxylesterase 4</td><td>8.4%</td><td>1.3%</td><td>63.7%</td><td>26.5%</td><td>14.0%</td><td>2.2%</td><td>47.8%</td><td>36.0%</td></tr>
<tr><td>>tr|G3I5K8|G3I5K8_CRIGR Carboxylic ester hydrolase</td><td>0.0%</td><td>0.0%</td><td>100.0%</td><td>0.0%</td><td>0.0%</td><td>0.0%</td><td>16.7%</td><td>83.3%</td><td rowspan="2">Possibly no binding</td></tr>
<tr><td>>tr|G3H1D5|G3H1D5_CRIGR Carboxypeptidase</td><td>0.0%</td><td>0.0%</td><td>0.0%</td><td>100.0%</td><td>0.0%</td><td>0.0%</td><td>0.0%</td><td>100.0%</td></tr>
</table>

FIG. 19

| Protein Name | Native HMW | Native Main | Native Tail | Native LMW | Denaturing (20% ACN) HMW | Denaturing (20% ACN) Main | Denaturing (20% ACN) Tail | Denaturing (20% ACN) LMW | Denaturing (SLS+SDC) HMW | Denaturing (SLS+SDC) Main | Denaturing (SLS+SDC) Tail | Denaturing (SLS+SDC) LMW |
|---|---|---|---|---|---|---|---|---|---|---|---|---|
| >tr\|G3GZB2\|G3GZB2_CRIGR Acid ceramidase | 100.0% | 0.0% | 0.0% | 0.0% | 100.0% | 0.0% | 0.0% | 0.0% | | | | |
| >tr\|G3I4W7\|G3I4W7_CRIGR Cathepsin D | 100.0% | 0.0% | 0.0% | 0.0% | 25.0% | 0.0% | 25.0% | 50.0% | 30.3% | 0.0% | 0.0% | 69.7% |
| >tr\|G3I7X7\|G3I7X7_CRIGR Carboxylic ester hydrolase | 97.0% | 3.0% | 0.0% | 0.0% | 23.0% | 0.0% | 63.0% | 14.0% | | | | |
| >tr\|G3I6T1\|G3I6T1_CRIGR Phospholipase B-like | 53.0% | 23.0% | 11.0% | 13.0% | 8.0% | 12.0% | 19.0% | 61.0% | 0.0% | 4.2% | 0.0% | 95.8% |
| >tr\|G3INC5\|G3INC5_CRIGR Cathepsin L1 | 47.0% | 0.0% | 13.0% | 40.0% | 26.0% | 0.0% | 26.0% | 49.0% | | | | |
| >tr\|Q9EPP7\|Q9EPP7_CRIGR CTSZ | 22.0% | 0.0% | 6.0% | 72.0% | 9.0% | 0.0% | 9.0% | 83.0% | | | | |
| >tr\|G3I7X9\|G3I7X9_CRIGR Liver carboxylesterase 1 | 19.0% | 0.0% | 30.0% | 51.0% | 17.0% | 0.0% | 38.0% | 45.0% | | | | |
| >tr\|G3I7X5\|G3I7X5_CRIGR Liver carboxylesterase 4 | 12.0% | 0.0% | 48.0% | 39.0% | 18.0% | 0.0% | 33.0% | 49.0% | 0.0% | 0.0% | 0.0% | 100.0% |
| >tr\|G3I5L0\|G3I5L0_CRIGR Liver carboxylesterase 4 | 8.0% | 1.0% | 64.0% | 27.0% | 14.0% | 2.0% | 48.0% | 36.0% | | | | |
| >tr\|G3I5K8\|G3I5K8_CRIGR Carboxylic ester hydrolase | 0.0% | 0.0% | 100.0% | 0.0% | 0.0% | 0.0% | 17.0% | 83.0% | | | | |
| >tr\|G3H1D5\|G3H1D5_CRIGR Carboxypeptidase | 0.0% | 0.0% | 0.0% | 100.0% | 0.0% | 0.0% | 0.0% | 100.0% | 0.0% | 0.0% | 0.0% | 100.0% |
| >tr\|G3H8V5\|G3H8V5_CRIGR Carboxypeptidase | | | | | | | | | 31.8% | 0.0% | 0.0% | 68.2% |
| >tr\|G3IHL7\|G3IHL7_CRIGR Cathepsin M | | | | | | | | | 21.1% | 0.0% | 0.0% | 78.9% |
| >tr\|G3H6V7\|G3H6V7_CRIGR Lipoprotein lipase | | | | | | | | | 0.0% | 40.0% | 0.0% | 60.0% |
| >tr\|G3I769\|G3I769_CRIGR Carboxylic ester hydrolase | | | | | | | | | 0.0% | 0.0% | 0.0% | 100.0% |
| >tr\|G3IBF4\|G3IBF4_CRIGR Serine protease HTRA1 | | | | | | | | | 0.0% | 0.0% | 0.0% | 100.0% |
| >tr\|G3HQY6\|G3HQY6_CRIGR Lipase | | | | | | | | | 0.0% | 0.0% | 0.0% | 100.0% |

FIG. 25

| Accession | Protein Description | mAb2 | | mAb3 | | mAb4 | | mAb5 | | mAb6 | |
|---|---|---|---|---|---|---|---|---|---|---|---|
| | | DS | HMW | DS | HMW | DS | HMW | DS | HMW | DS | HMW |
| G3GTT2 | C-C motif chemokine | 37.4 | 1738.5 | 5.4 | 42.5 | 5.2 | 61.6 | 3.1 | 39.3 | 3.3 | 20.9 |
| G3H8V5 | Carboxypeptidase | 5.7 | 605.3 | 0.1 | 0.1 | 0 | 2.0 | 0 | 0.1 | 0 | 0.3 |
| G3HXN7 | Beta-hexosaminidase | 0 | 120.3 | 0.1 | 13.8 | 0 | 35.7 | 0 | 19.6 | 0 | 9.8 |
| G3GR64 | Inter-alpha-trypsin inhibitor heavy chain H5 | 0.6 | 47.4 | 2.2 | 23.4 | 1.6 | 27.6 | 0.2 | 10.1 | 0.3 | 13.2 |
| G3H6V7 | Lipoprotein lipase | 1.9 | 37.7 | 0.1 | 3.5 | 0.1 | 0.9 | 0.2 | 0.9 | 0.1 | 1.2 |
| G3H533 | Peptidyl-prolyl cis-trans isomerase | 5.2 | 21.9 | 5.9 | 18.9 | 2.5 | 16.0 | 1.4 | 8.9 | 1.3 | 7.6 |
| G3INC5 | Cathepsin L1 | 0.6 | 19.4 | 0.8 | 7.1 | 0.2 | 32.5 | 0.2 | 8.4 | 0.1 | 1.5 |
| G3I5L3 | Annexin | 0.4 | 16.7 | 0.4 | 3.6 | 2.2 | 28.9 | 0.9 | 18.1 | 0.1 | 3.5 |
| G3I1H5 | Legumain | 0.2 | 13.6 | 0.1 | 0.7 | 0 | 0.1 | 0 | 0 | 0 | 0 |
| G3GUR1 | Complement C1r-A subcomponent | 0 | 11.1 | 1.9 | 12.7 | 0.8 | 50.6 | 0.3 | 7.4 | 0 | 5.2 |
| G3IIK9 | Cornifin-A | 0.1 | 9.5 | 0.1 | 2.1 | 4.6 | 77.0 | 0.5 | 14.9 | 2.6 | 51.4 |

0 1 100

FIG. 40

| Accession | Protein Description | mAb2 | | mAb3 | | mAb4 | | mAb5 | | mAb6 | |
|---|---|---|---|---|---|---|---|---|---|---|---|
| | | DS | HMW | DS | HMW | DS | HMW | DS | HMW | DS | HMW |
| G3GYP9 | Peroxiredoxin | 0 | 7.9 | 0.3 | 7.3 | 13.2 | 46.3 | 0.6 | 15.9 | 0.4 | 17.8 |
| G3IIB1 | Sialate O-acetylesterase | 0 | 6.2 | 3.2 | 3.2 | 1.0 | 40.3 | 1.7 | 11.9 | 0.8 | 3.5 |
| G3IKC3 | Glutathione S-transferase Mu 6 | 0.1 | 5.7 | 3.2 | 11.7 | 3.5 | 55.7 | 6.5 | 84.7 | 3.6 | 44.0 |
| G3I3K5 | G-protein coupled receptor 56 | 0.2 | 4.9 | 0.7 | 6.8 | 0.5 | 15.6 | 0.9 | 15.7 | 0.4 | 9.2 |
| Q9EPP7 | Cathepsin Z | 0.1 | 4.3 | 0.3 | 0.2 | 0.5 | 5.7 | 0.3 | 2.8 | 0 | 0 |
| G3IG05 | Annexin | 0.1 | 3.3 | 0.1 | 7.3 | 5.9 | 14.2 | 0.5 | 22.2 | 0.5 | 18.6 |
| G3HQY6 | Lipase | 0.2 | 2.6 | 0.5 | 13.8 | 0.7 | 3.7 | 1.4 | 35.9 | 0.5 | 6.8 |
| G3IBH0 | Metalloproteinase inhibitor 1 | 0.2 | 2.1 | 3.0 | 9.5 | 11.4 | 151.4 | 4 | 39.2 | 4.9 | 57.2 |
| G3HNJ3 | Clusterin | 0.3 | 1.7 | 0.6 | 33.2 | 0.7 | 1.3 | 0.6 | 0.7 | 0.3 | 0.8 |
| G3I4H6 | Fructose-bisphosphate aldolase | 0 | 0.5 | 0.5 | 7.1 | 0.6 | 33.7 | 0.6 | 57.6 | 0.3 | 22.9 |
| G3I4E8 | Fatty acid-binding protein, adipocyte | 0 | 0.3 | 1.9 | 4.5 | 1.4 | 5.1 | 3.3 | 14.9 | 2.8 | 9.3 |
| G3I6T1 | Putative phospholipase B-like 2 | 0 | 0.1 | 0 | 0.5 | 0 | 0 | 0 | 1.6 | 0 | 0.5 |
| G3GZB2 | Acid ceramidase | 0 | 0 | 0 | 0.2 | 0.1 | 0.2 | 0 | 0.2 | 0 | 0.3 |
| G3I4W7 | Cathepsin D | 0 | 0 | 0 | 0.3 | 0 | 0 | 0 | 0.1 | 0 | 0.1 |

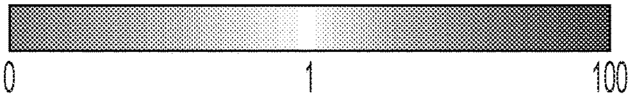

FIG. 40
CONTINUED

| Protein Accession | MW [kDa] | calc. pI | Protein Name | DS | Enriched total HMW | Enriched Dimer | Enriched vHMW |
|---|---|---|---|---|---|---|---|
| G3GTT2 | 15.8 | 9.16 | C-C motif chemokine | 37.4 | 1738.5 | 7733.9 | 934.5 |
| G3H8V5 | 54.2 | 6.11 | Carboxypeptidase | 5.7 | 605.3 | 1530.9 | 266.8 |
| G3IAP3 | 38.1 | 8.36 | Connective tissue growth factor | 0 | 264 | 64.5 | 776.8 |
| G3HXN7 | 60.1 | 7.36 | Beta-hexosaminidase | 0.1 | 120.3 | 261.9 | 67.3 |
| G3I664 | 55.2 | 8.13 | Procollagen C-endopeptidase enhancer 1 | 4.2 | 103.5 | 141.6 | 73.7 |
| G3HEJ4 | 154.4 | 6.64 | Neogenin | 0 | 47.6 | 94.8 | 19.1 |
| G3GR64 | 102 | 8.60 | Inter-alpha-trypsin inhibitor heavy chain H5 | 0.6 | 47.4 | 82.6 | 36.2 |
| G3H6V7 | 50.5 | 7.85 | Lipoprotein lipase | 1.9 | 37.7 | 8.8 | 10.9 |
| G3HRF8 | 65 | 6.30 | CD166 antigen | 0 | 34.2 | 77.2 | 0.7 |
| Q9ERF7 | 57.6 | 7.24 | Intercellular adhesion molecule 1 | 0 | 31.8 | 69.8 | 9.8 |
| G3HX58 | 73.0 | 7.94 | Leucine-rich repeat transmembrane protein FLRT3 | 0 | 29.4 | 45.3 | 33.8 |
| G3HGU9 | 110.4 | 6.15 | Oncostatin-M specific receptor subunit beta | 0 | 24.7 | 63.9 | 0.4 |
| G3I8P7 | 53.7 | 6.87 | N-acetylglucosamine-6-sulfatase | 0 | 23.4 | 55.3 | 11.2 |
| A0A061HWS7 | 89.6 | 8.36 | Ethanolamine-phosphatecytidylyltransferase-like protein | 0 | 23.1 | 13.3 | 11.5 |
| G3H533 | 23.6 | 9.58 | Peptidyl-prolyl cis-trans isomerase | 5.2 | 21.9 | 28.2 | 22.6 |
| G3INC5 | 37.2 | 7.17 | Cathepsin L1 | 0.6 | 19.4 | 106.7 | 11.9 |
| G3IG05 | 27 | 5.97 | Annexin | 0.5 | 16.7 | 17.8 | 12.5 |
| G3HS71 | 72.5 | 7.55 | Vasorin | 0 | 16.4 | 72.0 | 17.8 |
| G3H277 | 66.6 | 7.05 | Tyrosine-protein phosphatase non-receptor type 11 | 0 | 15.6 | 22.2 | 14.3 |
| A0A061IBV6 | 24.6 | 9.39 | Beta-hexosaminidase subunit alpha (Fragment) | 0 | 15.2 | 75.2 | 15.5 |
| Number of HCPs identified (> 0.1 ppm) | | | | 26 | 110 | 123 | 102 |

0 1 100

FIG. 42

SIZE EXCLUSION CHROMATOGRAPHY FOR CHARACTERIZING HOST CELL PROTEINS

CROSS-REFERENCE TO RELATED APPLICATIONS

This application claims priority to and the benefit of U.S. Provisional Patent Application No. 63/314,144, filed Feb. 25, 2022, U.S. Provisional Application No. 63/341,381, filed May 12, 2022 and U.S. Provisional Patent Application No. 63/426,221, filed Nov. 17, 2022 which are each herein incorporated by reference.

FIELD

This application relates to methods for identification, characterization, and removal of host cell proteins.

BACKGROUND

High molecular weight (HMW) aggregates in biotherapeutic products pose challenges in drug development, commercial manufacturing, and product stability throughout the storage life of the product. HMW aggregates can form during manufacturing, formulation, and shipment or delivery to patients. The presence of HMW aggregates in biotherapeutic products may affect drug efficacy and increase the risk of adverse immune responses in patients. Therefore, the level of HMW species in biotherapeutic products is monitored as a critical quality attribute.

An additional potential mechanism for the adverse effects of HMW species in biotherapeutics is the presence of host cell proteins (HCPs). The presence of residual host cell proteins (HCPs) can cause potential safety risk for biopharmaceutical products and problems in manufacturing. Since recombinant DNA technology has been used widely for producing biopharmaceutical products in host cells, it is necessary to remove impurities to obtain biopharmaceutical products having high purity. Any residual impurities after conducting the purification bioprocesses should be present at an acceptably low level prior to conducting clinical studies. In particular, residual HCPs derived from mammalian expression systems, for example Chinese hamster ovary (CHO) cells, can compromise product safety, quality and stability. Even trace amounts of particular HCPs can sometimes cause an immunogenic response or an undesirable modification. Thus, host cell proteins in drug products and during the manufacturing process need to be monitored.

HCPs may end up in a final drug substance through multiple different pathways. For example, a HCP may bind to the biotherapeutic, preventing it from being removed during purification. Alternatively, a HCP may be co-purified alongside the biotherapeutic in an unbound state. Understanding the mechanism of HCP contamination may be useful in process development to prevent further contamination.

Most monoclonal antibody (mAb) purification techniques include an initial affinity chromatography step, for example Protein A affinity chromatography, followed by several polishing steps. The presence of HCPs in Protein A eluate is mainly due to interaction with column resin/ligands or mAbs. The HCPs retained after Protein A purification due to column resin interactions maybe removed in the subsequent polishing steps. However, the HCPs associated with mAbs are difficult to remove and can escape from the purification process. Identifying the co-eluting HCPs and understanding the interaction mechanisms described above are crucial for process development.

The identification of HCP impurities in biopharmaceutical products is challenging due to the broad dynamic range of protein concentrations in samples with very high complexity. In particular, the presence of at least one high-abundance protein or peptide in a sample, such as a therapeutic protein, creates technical obstacles to the detection, identification and quantification of very low-abundance proteins in a sample. Furthermore, the presence of HCPs in the HMW fraction of biotherapeutic products, and the possible contribution of said HCPs to adverse effects such as instability or immunogenicity, has not been extensively characterized.

Therefore, demand exists for methods and systems to identify, characterize, and remove host cell proteins in biotherapeutic products in a sensitive and specific fashion.

SUMMARY

A method has been developed for identifying HCPs using size exclusion chromatography (SEC) as an orthogonal separation method prior to subjecting a sample including a protein of interest to liquid chromatography-mass spectrometry (LC-MS) analysis. A sample including a protein of interest and at least one HCP, wherein the protein of interest is present at a much higher abundance than the at least one HCP, can be separated into, for example, high molecular weight (HMW), main, tail, and/or low molecular weight (LMW) fractions. Biotherapeutics such as antibodies, antibody fusion proteins, receptors, or receptor fusion proteins may be much larger than HCPs and can effectively be separated from HCPs based on size. Enrichment of HCPs into a fraction depleted of the high-abundance protein of interest allows for superior identification of HCPs using LC-MS analysis. This disclosure describes the optimization of an SEC-based method for HCP identification, including exemplary optimized denaturation conditions, digestion conditions, protein loading amount, SEC fraction delineation, surfactant inclusion, and acid precipitation.

A method has also been developed for characterizing the binding of HCPs to a protein of interest using SEC. Understanding the binding properties of HCPs to a protein of interest is valuable, for example in order to understand the mechanism of host cell protein contamination in a sample, for example a drug substance. HCPs bound to a protein of interest will elute earlier in SEC compared to unbound HCPs. In mild denaturing conditions, for example in 20% acetonitrile, weak HCP binding to a protein of interest will be abolished and a HCP will display a shift to lower molecular weight SEC fractions compared to separation in non-denaturing conditions, while strong HCP binding to a protein of interest will be largely unaffected. In strong denaturing conditions, for example in 12 mM sodium lauroyl sarcosate and 12 mM sodium deoxycholate, effectively all HCP binding to a protein of interest may be abolished. By comparing separation profiles of HCPs in non-denaturing and denaturing conditions, the binding properties of an HCP to a protein of interest may be established.

A method has additionally been developed for identifying, quantifying, and removing HCP impurities from a sample of interest, for example a biotherapeutic product. In particular, the present disclosure demonstrates that HCPs of concern may be greatly enriched in a HMW fraction of a biotherapeutic product due to specific interactions with aggregates or multimers of a protein of interest included in the product. HCPs may be identified and quantified using SEC analysis of a biotherapeutic product, followed by analysis and comparison of SEC fractions. For example, a drug substance (DS) may be subjected to native digestion, SEC analysis, fractionation into HMW, monomer, and LMW fractions, further sample preparation such as denaturation, reduction, digestion and alkylation, and liquid chromatography-tandem mass spectrometry (LC-MS/MS) analysis to identify and quantify HCPs that are enriched in HMW fractions of a biotherapeutic product. A profile of HCPs present in each SEC fraction of a biotherapeutic product DS may be developed to determine whether the product may be improved by separating and removing SEC fractions, for example by reducing the abundance of an HCP impurity of concern. This determination may be made, for example, on the basis of the concentration and/or abundance of an HCP, the percentage of the HCP enriched in a particular SEC fraction, and the known risks of inclusion of the particular HCP in a biotherapeutic product. Based on this determination, a process for harvesting and purifying a biotherapeutic product sample, for example DS, may be improved by the addition of an SEC step to remove a HMW fraction containing an enriched HCP, thereby improving the safety and efficacy of the biotherapeutic product.

This disclosure provides a method for identifying HCP impurities in a sample. In some exemplary embodiments, the method comprises: (a) subjecting a sample including at least one protein of interest and at least one HCP impurity to size exclusion chromatography (SEC) analysis to produce fractions, and (b) subjecting said fractions to LC-MS analysis to identify said at least one HCP impurity.

In one aspect, the at least one protein of interest is an antibody, a bispecific antibody, a monoclonal antibody, a fusion protein, an antibody-drug conjugate, an antibody fragment, or a protein pharmaceutical product.

In one aspect, an amount of protein loaded onto the SEC column is between about 0.5 mg and about 20 mg, between about 1 mg and about 10 mg, between about 8 mg and about 12 mg, about 1 mg, about 5 mg, about 10 mg, or about 20 mg. In a specific aspect, an amount of protein loaded onto the SEC column is about 10 mg.

In one aspect, a mobile phase for the SEC analysis comprises about 10 mM phosphate and about 150 mM NaCl. In another aspect, a mobile phase for the SEC analysis is a denaturing mobile phase. In a further aspect, a mobile phase for the SEC analysis is a non-denaturing mobile phase.

In one aspect, a mobile phase for the SEC analysis comprises acetonitrile, optionally wherein a concentration of the acetonitrile is between about 5% v/v and about 20% v/v, between about 10% v/v and about 20% v/v, between about 15% v/v and about 20% v/v, about 5% v/v, about 10% v/v, about 15% v/v, or about 20% v/v. In a specific aspect, a concentration of the acetonitrile is about 20% v/v.

In one aspect, a mobile phase for the SEC analysis comprises at least one surfactant, optionally wherein a concentration of the at least one surfactant is between about 6 mM and about 36 mM, about 12 mM, or about 24 mM. In a specific aspect, the at least one surfactant is a detergent. In a more specific aspect, the at least one detergent is selected from a group consisting of sodium deoxycholate, sodium lauroyl sarcosinate, and a combination thereof. In a further specific aspect, the at least one detergent is sodium deoxycholate and sodium lauroyl sarcosinate, wherein a concentration of sodium deoxycholate is about 12 mM and a concentration of sodium lauroyl sarcosinate is about 12 mM.

In one aspect, the fractions comprise a high molecular weight (HMW) fraction, a main fraction, and a low molecular weight (LMW) fraction. In a specific aspect, the fractions further comprise a tail fraction. In another specific aspect, the HMW fraction includes eluate between about 0.3 column volumes (CV) and about 5 milli absorbance units (mAU). In a further specific aspect, the main fraction includes eluate between about 5 mAU and about 40 mAU. In yet another specific aspect, the tail fraction includes eluate between about 40 mAU and about 10 mAU, or between about 40 mAU and about 3 mAU. In still another specific aspect, the LMW fraction includes eluate between about 10 mAU and about 1.1 CV, or between about 3 mAU and about 1.1 CV.

In one aspect, the method further comprises subjecting the fractions to enzymatic digestion prior to the LC-MS analysis of step (b). In a specific aspect, the enzymatic digestion is a limited digestion. In another specific aspect, the enzymatic digestion is performed by contacting the fractions to trypsin. In a further specific aspect, the enzymatic digestion is performed by contacting the fractions to a digestive enzyme at an enzyme to protein ratio of between about 1:100 and about 1:2000, about 1:100, about 1:200, about 1:300, about 1:400, about 1:500, about 1:1000, or about 1:2000. In still another specific aspect, the enzyme to protein ratio is about 1:200 for the HMW fraction. In another specific aspect, the enzyme to protein ratio is about 1:2000 for the main fraction. In a further specific aspect, the enzyme to protein ratio is about 1:500 for the tail fraction. In yet another specific aspect, the enzyme to protein ratio is about 1:200 for the LMW fraction.

In one aspect, the method further comprises subjecting the fractions to acid precipitation prior to the LC-MS analysis of step (b). In a specific aspect, the acid precipitation comprises contacting the fractions to about 1% trifluoroacetic acid.

In one aspect, the liquid chromatography of step (b) comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, the mass spectrometer is an electrospray ionization mass spectrometer, nano-electrospray ionization mass spectrometer, or an Orbitrap-based mass spectrometer, wherein the mass spectrometer is coupled to said liquid chromatography system.

This disclosure provides an additional method for identifying host cell protein (HCP) impurities in a sample. In some exemplary embodiments, the method comprises: (a) subjecting a sample including at least one protein of interest and at least one HCP impurity to size exclusion chromatography (SEC) analysis to produce fractions, wherein a mobile phase for said SEC analysis comprises about 12 mM sodium lauroyl sarcosinate and about 12 mM sodium deoxycholate; (b) subjecting said fractions to acid precipitation to produce detergent-depleted fractions, wherein said acid precipitation comprises contacting said fractions to about 1% trifluoroacetic acid; (c) subjecting said detergent-depleted fractions to buffer exchange to produce buffer-exchanged fractions; (d) subjecting said buffer-exchanged fractions to limited digestion to produce peptide digests, wherein said limited digestion comprises contacting said buffer-exchanged fractions to trypsin at an enzyme to substrate ratio between about 1:200 and about 1:2000; and (e) subjecting said peptide digests to LC-MS analysis to identify said at least one HCP impurity.

In one aspect, the at least one protein of interest is an antibody, a bispecific antibody, a monoclonal antibody, a fusion protein, an antibody-drug conjugate, an antibody fragment, or a protein pharmaceutical product.

In one aspect, an amount of protein loaded onto the SEC column is between about 0.5 mg and about 20 mg, between about 1 mg and about 10 mg, between about 8 mg and about 12 mg, about 1 mg, about 5 mg, about 10 mg, or about 20 mg. In a specific aspect, an amount of protein loaded onto the SEC column is about 10 mg.

In one aspect, the fractions comprise a high molecular weight (HMW) fraction, a main fraction, and a low molecular weight (LMW) fraction. In a specific aspect, the fractions further comprise a tail fraction. In another specific aspect, the HMW fraction includes eluate between about 0.3 column volumes (CV) and about 5 milli absorbance units (mAU). In a further specific aspect, the main fraction includes eluate between about 5 mAU and about 40 mAU. In yet another specific aspect, the tail fraction includes eluate between about 40 mAU and about 10 mAU, or between about 40 mAU and about 3 mAU. In still another specific aspect, the LMW fraction includes eluate between about 10 mAU and about 1.1 CV, or between about 3 mAU and about 1.1 CV.

In one aspect, the liquid chromatography of step (e) comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, the mass spectrometer is an electrospray ionization mass spectrometer, nano-electrospray ionization mass spectrometer, or an Orbitrap-based mass spectrometer, wherein said mass spectrometer is coupled to said liquid chromatography system.

This disclosure also provides a method for characterizing the binding of a HCP impurity to a protein of interest. In some exemplary embodiments, the method comprises: (a) obtaining a sample including a protein of interest and at least one HCP impurity, (b) subjecting said sample to size exclusion chromatography (SEC) analysis using a non-denaturing mobile phase to produce native fractions; (c) subjecting said sample of (a) to SEC analysis using a denaturing mobile phase to produce denatured fractions; (d) subjecting said native fractions and said denatured fractions to LC-MS analysis to produce a native separation profile and a denatured separation profile of said at least one HCP impurity; and (e) comparing said native separation profile to said denatured separation profile to characterize the binding of said at least one HCP impurity to said protein of interest.

In one aspect, the protein of interest is an antibody, a bispecific antibody, a monoclonal antibody, a fusion protein, an antibody-drug conjugate, an antibody fragment, or a protein pharmaceutical product.

In one aspect, an amount of protein loaded onto the SEC column is between about 0.5 mg and about 20 mg, between about 1 mg and about 10 mg, between about 8 mg and about 12 mg, about 1 mg, about 5 mg, about 10 mg, or about 20 mg. In a specific aspect, an amount of protein loaded onto the SEC column is about 10 mg.

In one aspect, a mobile phase for the SEC analysis comprises about 10 mM phosphate and about 150 mM NaCl. In another aspect, the denaturing mobile phase is a mild denaturing mobile phase.

In one aspect, the denaturing mobile phase comprises acetonitrile, optionally wherein a concentration of the acetonitrile is between about 5% v/v and about 20% v/v, between about 10% v/v and about 20% v/v, between about 15% v/v and about 20% v/v, about 5% v/v, about 10% v/v, about 15% v/v, or about 20% v/v. In a specific aspect, a concentration of the acetonitrile is about 20% v/v.

In one aspect, the fractions comprise a high molecular weight (HMW) fraction, a main fraction, and a low molecular weight (LMW) fraction. In a specific aspect, the fractions further comprise a tail fraction. In another specific aspect, the HMW fraction includes eluate between about 0.3 column volumes (CV) and about 5 milli absorbance units (mAU). In a further specific aspect, the main fraction includes eluate between about 5 mAU and about 40 mAU. In yet another specific aspect, the tail fraction includes eluate between about 40 mAU and about 10 mAU, or between about 40 mAU and about 3 mAU. In still another specific aspect, the LMW fraction includes eluate between about 10 mAU and about 1.1 CV, or between about 3 mAU and about 1.1 CV.

In one aspect, the method further comprises subjecting the fractions to enzymatic digestion prior to the LC-MS analysis of step (d). In a specific aspect, the enzymatic digestion is a limited digestion. In another specific aspect, the enzymatic digestion is performed by contacting the fractions to trypsin. In a further specific aspect, the enzymatic digestion is performed by contacting the fractions to a digestive enzyme at an enzyme to protein ratio of between about 1:100 and about 1:2000, about 1:100, about 1:200, about 1:300, about 1:400, about 1:500, about 1:1000, or about 1:2000. In still another specific aspect, the enzyme to protein ratio is about 1:200 for the HMW fraction. In another specific aspect, the enzyme to protein ratio is about 1:2000 for the main fraction. In a further specific aspect, the enzyme to protein ratio is about 1:500 for the tail fraction. In yet another specific aspect, the enzyme to protein ratio is about 1:200 for the LMW fraction.

In one aspect, the liquid chromatography of step (d) comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, the mass spectrometer is an electrospray ionization mass spectrometer, nano-electrospray ionization mass spectrometer, or an Orbitrap-based mass spectrometer, wherein said mass spectrometer is coupled to the liquid chromatography system.

This disclosure provides a method for identifying HCP impurities in a sample. In some exemplary embodiments, the method comprises: (a) combining a sample including at least one protein of interest and at least one HCP impurity with a dissociation reagent to produce a first combination; (b) subjecting said first combination to acid precipitation to produce dissociation reagent-depleted fractions; and (c) subjecting said dissociation reagent-depleted fractions to liquid chromatography-mass spectrometry analysis to identify said at least one HCP impurity.

In one aspect, the at least one protein of interest is an antibody, a bispecific antibody, a monoclonal antibody, a fusion protein, an antibody-drug conjugate, an antibody fragment, or a protein pharmaceutical product.

In one aspect, the sample is incubated in said dissociation reagent for between about 5 minutes and about 120 minutes, about 15 minutes, about 30 minutes, about 60 minutes or about 120 minutes.

In one aspect, the dissociation reagent comprises at least one surfactant, optionally wherein a concentration of said at least one surfactant is between about 20 mM and about 120 mM, about 20 mM, about 40 mM, about 60 mM, about 100 mM or about 120 mM.

In one aspect, the at least one surfactant is a detergent.

In one aspect, the at least one detergent is selected from a group consisting of sodium deoxycholate, sodium lauroyl sarcosinate and a combination thereof.

In one aspect, the at least one detergent is sodium lauroyl sarcosinate, wherein a concentration of sodium lauroyl sarcosinate is between about 20 mM and about 120 mM, about 20 mM, about 40 mM, about 60 mM, about 100 mM or about 120 mM.

In one aspect, the at least one detergent is sodium deoxycholate and sodium lauroyl sarcosinate, wherein a concentration of sodium deoxycholate is between about 20 mM and about 120 mM, about 20 mM, about 40 mM, about 60 mM, about 100 mM or about 120 mM, and a concentration of sodium lauroyl sarcosinate is between about 20 mM and about 120 mM, about 20 mM, about 40 mM, about 60 mM, about 100 mM or about 120 mM.

In one aspect, the at least one detergent is sodium deoxycholate, wherein a concentration of sodium deoxycholate is between about 20 mM and about 120 mM, about 20 mM, about 40 mM, about 60 mM, about 100 mM or about 120 mM In one aspect, the method further comprises subjecting said dissociation reagent-depleted fractions to enzymatic digestion to produce peptides digests prior to the liquid chromatography-mass spectrometry analysis of step (c).

In one aspect, the enzymatic digestion is a limited digestion.

In one aspect, the enzymatic digestion is performed by contacting said dissociation reagent-depleted fractions to trypsin.

In one aspect, the enzymatic digestion is performed by contacting said dissociation reagent-depleted fractions to a digestive enzyme at an enzyme to protein ratio of between about 1:100 and about 1:2000, between about 1:200 and about 1:2000, about 1:100, about 1:200, about 1:300, about 1:400, about 1:500, about 1:1000, or about 1:2000.

In one aspect, the enzyme to protein ratio is about 1:200.

In one aspect, the method further comprises desalting the peptide digests prior to the liquid chromatography-mass spectrometry analysis of step (c).

In one aspect, the acid precipitation is incubated for between about 5 minutes and about 60 minutes, about 5 minutes or about 60 minutes.

In one aspect, the acid precipitation comprises contacting said first combination to between about 2.5% and about 10% trifluoroacetic acid, about 2.5% trifluoroacetic acid, about 5% trifluoroacetic acid, about 7.5% trifluoroacetic acid or about 10% trifluoroacetic acid.

In one aspect, the liquid chromatography comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, the mass spectrometer is an electrospray ionization mass spectrometer, nano-electrospray ionization mass spectrometer, or an Orbitrap-based mass spectrometer, wherein said mass spectrometer is coupled to said liquid chromatography system.

This disclosure provides a method for identifying HCP impurities in a sample. In some exemplary embodiments, the method comprises: (a) combining a sample including at least one protein of interest and at least one HCP impurity with a dissociation reagent to produce a first combination; (b) subjecting said first combination to acid precipitation to produce dissociation reagent-depleted fractions; (c) subjecting said dissociation reagent-depleted fractions to buffer exchange to produce buffer-exchanged fractions; (d) subjecting said buffer-exchanged fractions to enzymatic digestion to produce peptide digests; and (e) subjecting said peptide digests to liquid chromatography-mass spectrometry analysis to identify said at least one HCP impurity.

In one aspect, the at least one protein of interest is an antibody, a bispecific antibody, a monoclonal antibody, a fusion protein, an antibody-drug conjugate, an antibody fragment, or a protein pharmaceutical product.

In another aspect, the dissociation reagent comprises at least one surfactant, optionally wherein a concentration of said at least one surfactant is between about 20 mM and about 120 mM, about 20 mM, about 40 mM, about 60 mM, about 100 mM or about 120 mM.

In another aspect, the at least one surfactant is a detergent.

In yet another aspect, the at least one detergent is selected from a group consisting of sodium deoxycholate, sodium lauroyl sarcosinate and a combination thereof.

In one aspect, the first combination is incubated for between about 5 minutes and about 120 minutes, about 5 minutes, about 15 minutes, about 30 minutes, about 60 minutes, about 90 minutes or about 120 minutes prior to the acid precipitation of step (b).

In another aspect, the at least one detergent is sodium lauroyl sarcosinate, wherein a concentration of sodium lauroyl sarcosinate is between about 20 mM and about 120 mM, about 20 mM, about 40 mM, about 60 mM, about 100 mM or about 120 mM.

In another aspect, the at least one detergent is sodium deoxycholate and sodium lauroyl sarcosinate, wherein a concentration of sodium deoxycholate between about 20 mM and about 120 mM, about 20 mM, about 40 mM, about 60 mM, about 100 mM or about 120 mM, and a concentration of sodium lauroyl sarcosinate is between about 20 mM and about 120 mM, about 20 mM, about 40 mM, about 60 mM, about 100 mM or about 120 mM.

In yet another aspect, the at least one detergent is sodium deoxycholate, wherein a concentration of sodium deoxycholate is between about 20 mM and about 120 mM, about 20 mM, about 40 mM, about 60 mM, about 100 mM or about 120 mM.

In one aspect, the enzymatic digestion is a limited digestion.

In one aspect, the enzymatic digestion is performed by contacting said buffer-exchanged fractions to trypsin.

In another aspect, the enzymatic digestion is performed by contacting said buffer-exchanged fractions to a digestive enzyme at an enzyme to protein ratio of between about 1:100 and about 1:2000, between about 1:200 and about 1:2000, about 1:100, about 1:200, about 1:300, about 1:400, about 1:500, about 1:1000, or about 1:2000.

In yet another aspect, the enzyme to protein ratio is about 1:200.

In one aspect, the method further comprises desalting the peptide digests prior to the liquid chromatography-mass spectrometry analysis of step (e).

In one aspect, the acid precipitation is incubated for between about 5 minutes and about 60 minutes, about 5 minutes or about 60 minutes.

In one aspect, the acid precipitation comprises contacting said first combination to between about 2.5% and about 10% trifluoroacetic acid, about 2.5% trifluoroacetic acid, about 5% trifluoroacetic acid, about 7.5% trifluoroacetic acid or about 10% trifluoroacetic acid.

In one aspect, the liquid chromatography comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

This disclosure further provides a method for manufacturing a biotherapeutic product. In some exemplary embodiments, the method comprises (a) subjecting a first sample including at least one protein of interest and at least one host cell protein (HCP) impurity to size exclusion chromatography (SEC) analysis to produce a plurality of fractions; (b) subjecting said plurality of fractions to liquid chromatography-tandem mass spectrometry (LC-MS/MS) analysis to determine an identity and quantity of said at least one HCP impurity; (c) using said identity and quantity to determine whether said at least one HCP impurity is an impurity of concern in at least one of said plurality of fractions; (d) subjecting a second sample including said at least one protein of interest and said at least one HCP impurity to SEC analysis to produce a second plurality of fractions; and (e) using the determination of step (c), removing said at least one fraction in which said at least one HCP impurity is an impurity of concern from said plurality of fractions of step (d) to manufacture a biotherapeutic product.

In one aspect, the protein of interest is an antibody, a bispecific antibody, a monoclonal antibody, a fusion protein, an antibody-drug conjugate, an antibody fragment, or a protein pharmaceutical product.

In one aspect, the mobile phase for said SEC analysis comprises about 150 mM ammonium acetate.

In one aspect, the at least one HCP impurity comprises a lipase, a protease, or a combination thereof. In another aspect, the at least one HCP impurity comprises C-C motif chemokine.

In one aspect, the plurality of fractions comprise a high molecular weight (HMW) fraction, a very high molecular weight (vHMW) fraction, a dimer fraction, a monomer fraction, a low molecular weight (LMW) fraction, a tail fraction, or a combination thereof.

In one aspect, a fraction in which said at least one HCP impurity is an impurity of concern is a HMW fraction.

In one aspect, the at least one HCP impurity is present in a fraction at between about 1000 parts per million (ppm) and about 10000 ppm, about 1000 ppm, about 2000 ppm, about 3000 ppm, about 4000 ppm, about 5000 ppm, about 6000 ppm, about 7000 ppm, about 8000 ppm, about 9000 ppm, or about 10000 ppm.

In one aspect, a percentage of the at least one HCP impurity enriched in a HMW fraction is between about 30% and about 100%, about 30%, about 40%, about 50%, about 60%, about 70%, about 80%, about 90%, or about 100%.

In one aspect, the method further comprises subjecting the sample of (a) to native digestion prior to SEC analysis. In a specific aspect, the native digestion is a limited digestion. In another specific aspect, the native digestion is performed by contacting the sample to trypsin.

In one aspect, the LC-MS/MS analysis comprises reverse phase liquid chromatography, ion exchange chromatography, anion exchange chromatography, cation exchange chromatography, strong cation exchange chromatography, size exclusion chromatography, affinity chromatography, Protein A chromatography, hydrophobic interaction chromatography, hydrophilic interaction chromatography, mixed-mode chromatography, or a combination thereof.

In one aspect, the LC-MS/MS analysis comprises parallel reaction monitoring.

This disclosure provides an additional method for manufacturing a biotherapeutic product. In some exemplary embodiments, the method comprises subjecting a sample including a protein of interest, at least one HMW species, and at least one HCP impurity to one or more chromatography steps that reduce the abundance of said at least one HCP impurity, wherein said at least one HCP impurity interacts with said at least one HMW species.

In one aspect, an interaction of said at least one HCP impurity and said at least one HMW species may be identified by enriching said at least one HMW species. In a specific aspect, the enriching comprises subjecting a sample including said at least one HMW species and said at least one HCP impurity to SEC. In a more specific aspect, the method further comprises subjecting said at least one HMW species and said at least one HCP impurity to buffer exchange, native digestion, denaturation, molecular weight filtration, one or more additional chromatography steps, and/or mass spectrometry analysis.

In one aspect, the protein of interest is an antibody, a bispecific antibody, a monoclonal antibody, a fusion protein, an antibody-drug conjugate, an antibody fragment, or a protein pharmaceutical product.

In one aspect, the at least one HCP impurity comprises a lipase, a protease, or a combination thereof. In another aspect, the at least one HCP impurity comprises C-C motif chemokine.

In one aspect, the at least one HMW species comprises a dimer, an aggregate, or a combination thereof.

In one aspect, the one or more chromatography steps comprise reverse phase liquid chromatography, ion exchange chromatography, anion exchange chromatography, cation exchange chromatography, strong cation exchange chromatography, size exclusion chromatography, affinity chromatography, Protein A chromatography, hydrophobic interaction chromatography, hydrophilic interaction chromatography, mixed-mode chromatography, or a combination thereof These, and other, aspects of the present invention will be better appreciated and understood when considered in conjunction with the following description and accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

FIG. 18A shows HCPs detected in mAb1 drug substance that were found to have strong binding to mAb1 using the method of the present invention, according to an exemplary embodiment.

FIG. 18B shows HCPs detected in mAb1 drug substance that were found to have no binding to mAb1 using the method of the present invention, according to an exemplary embodiment.

FIG. 18C shows HCPs detected in mAb1 drug substance that were found to have weak binding to mAb1 using the method of the present invention, according to an exemplary embodiment.

FIG. 19 shows a binding profile of HCPs of particular interest in mAb1 drug substance, according to an exemplary embodiment.

FIG. 25 shows the change in HCPs of interest in mAb1 drug substance from later SEC fractions, indicating an antibody-bound state, to earlier SEC fractions, indicating an unbound state, according to an exemplary embodiment.

FIG. 40 shows a heatmap of HCPs identified and quantified in DS and enriched HMW samples from various mAbs, according to an exemplary embodiment.

FIG. 42 shows a heatmap of HCPs identified and quantified in enriched HMW, enriched dimer, enriched vHMW and DS samples from mAb2, according to an exemplary embodiment.

DETAILED DESCRIPTION

Figure 1A:
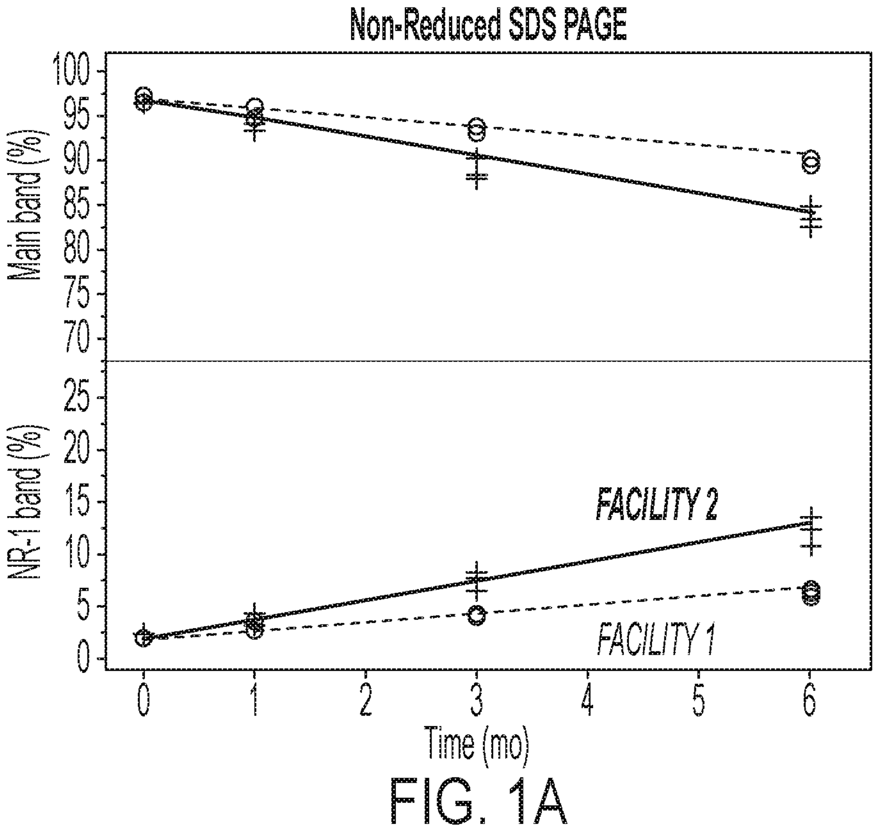
FIG. 1A shows degradation of aflibercept over time at 25° C. using SDS-PAGE, according to an exemplary embodiment.

High molecular weight (HMW) aggregates in biotherapeutic products pose challenges in drug development, commercial manufacturing, and product stability throughout the storage life of the product. HMW aggregates can form during manufacturing, formulation, and shipment or delivery to patients. The formation of these aggregates may be attributed to various external factors, such as exposure to interfaces, freeze-thaw cycles, heat and light stress, and agitation stress (Kiese et al., 2008, *J Pharm Sci,* 97(10): 4347-4366; Hawe et al., 2009, *Eur J Pharm Sci,* 38(2):79-87; Joubert et al., 2011, *J Biol Chem,* 286(28):25118-25133). The presence of HMW aggregates in biotherapeutic products may affect drug efficacy and increase the risk of adverse immune responses in patients (Ratanji et al., 2014, *J Immunotoxicol,* 11(2):99-109). Therefore, the level of HMW species in biotherapeutic products is monitored as a critical quality attribute. Moreover, various analytical methods have been developed to characterize the biophysical and biochemical properties of HMW aggregates, to understand the HMW formation mechanisms, and to assess the potential effects on product safety.

Recent studies have shown that the immunogenicity of HMW species is associated with modifications of the primary structure. For example, oxidized species incorporated into aggregates pose an elevated immunogenic risk (Filipe et al., 2012, mAbs, 4(6):740-752). Therefore, multiple analytical techniques are also used to study the primary structure and post-translational modifications (PTMs) of HMW species during the drug development process. The PTMs of HMW species, such as glycosylation, glycation, deamidation, and oxidation, have been evaluated and compared against the drug substance (DS).

Another potential critical quality attribute in biotherapeutic products is the presence of host cell proteins (HCPs). HCPs are process-related impurities introduced during antibody production from mammalian cell lines, and must be controlled to appropriate levels to ensure product safety and efficacy. The composition and abundance of HCPs in each step of the manufacturing process and in the final drug substance depends on many factors: the host expression system (for example, *E. coli* with about 4,300 genes compared to Chinese Hamster Ovary (CHO) cells with about 30,000 genes), expression manner (for example, cytoplasm compared to culture medium), physiochemical properties of the biotherapeutic (for example, hydrophobicity, charge, and structure), and the purification process (for example, Protein A chromatography, ion exchange chromatography, hydrophobic interaction chromatography, or filtration).

HCP impurities in biotherapeutic products may potentially cause a number of issues. HCPs may jeopardize patient safety: for example, the HCP PLBD2 may trigger a dose-dependent immune response, and host cell cytokines such as MCP-1 or TGF-β1 may cause toxicity. They may also compromise product quality and efficacy: for example, cathepsin D causes drug degradation, while lipases cause degradation of polysorbate, a common excipient that contributes to drug stability. Recent studies have revealed that low levels of HCPs can lead to product fragmentation (Robert et al., 2009, *Biotechnol Bioeng,* 104(6):1132-1141; Dick et al., 2008, *Biotechnol Bioeng,* 100(6):1132-1143; Luo et al., 2019, *Biotechnol Prog,* 35(1):e2732), immunogenic responses (Fischer et al., 2017, AAPS J, 19(1):254-263; Jawa et al., 2016, *AAPS J,* 18(6):1439-1452), and changes in formulations (Chiu et al., 2017, *Biotechnol Bioeng,* 114(5):1006-1015; McShan et al., 2016, PDA *J Pharm Sci Technol,* 70(4):332-345; Zhang et al., 2020, *J Pharm Sci,* 109(11):3300-3307; Zhang et al., 2021, *J Pharm Sci,* 110(12):3866-3873). For example, a trace amount of lipase may degrade polysorbate 20 and polysorbate 80, thereby causing drug product aggregation and affecting the product's shelf life (Chiu et al.; McShan et al.; Zhang et al. 2020; Zhang et al. 2021). In order to guide process development, it is important to assess critical process parameters and critical quality attributes (CQAs) of biotherapeutics and biotherapeutic candidates using analytical methods. Therefore, highly sensitive analytical methods are needed to monitor the downstream process activities and remove low-level HCPs to avoid harmful clinical events. The disclosure herein provides novel improvements to analytical methods for assessing HCPs in a biotherapeutic product.

A sub-population of residual HCPs often get co-purified with biotherapeutics through the purification process. Identification of HCPs is challenging at least in part due to the comparatively high abundance of a biotherapeutic, which creates a technical obstacle to detection of low-abundance proteins in a sample. Various approaches have been developed to ameliorate this issue, for example compressing the dynamic range of protein concentrations of a sample using ProteoMiner beads, or specifically enriching for HCPs using immunoassays, but each has logistical, technical or analytical shortcomings.

Traditionally, enzyme-linked immunosorbent assay (ELISA) and western blotting have been used for HCP analysis in biotherapeutics. However, these methods are unlikely to detect HCPs eliciting weak or no immune responses. In addition, ELISA usually does not indicate the identities of individual HCPs. Because the risks posed by individual HCP species differ, methods that can provide information regarding individual HCPs should be implemented as an orthogonal strategy for risk mitigation (Bracewell et al., 2015, *Biotechnol Bioeng,* 112(9):1727-1737; Abiri et al., 2018, *PLoS ONE,* 13(3)e0193339).

Liquid chromatography coupled with tandem mass spectrometry (LC-MS/MS) based proteomics has become a commonly used orthogonal HCP analysis strategy after recent advances in instrumentation and improved workflows. LC-MS/MS for HCP analysis not only enables the identification and quantitation of individual HCPs, but also mitigates the risk of lacking coverage for specific HCPs in polyclonal antibody reagent used in ELISA HCP assays. Moreover, LC-MS/MS-based HCP analysis enables understanding of the downstream process and can provide guidance for the removal of abundant or problematic HCPs.

Most monoclonal antibody (mAb) purification techniques include an initial affinity chromatography step, for example Protein A affinity chromatography, followed by several polishing steps. The presence of HCPs in Protein A eluate is mainly due to interaction with column resin/ligands or mAbs. The HCPs retained after Protein A purification due to column resin interactions maybe removed in the subsequent polishing steps. However, the HCPs associated with mAbs are difficult to remove and can escape from the purification process. Identifying the co-eluting HCPs and understanding the interaction mechanisms described above are crucial for process development.

The main challenge in identifying the HCPs in the final drug substance (DS) by MS is the large dynamic range in concentration. This challenge can be overcome by adding an additional dimension in separation, such as 2D-LC (Yang et al., 2018, *Anal Chem,* 90(22):13365-13372; Farrell et al., 2015, *Anal Chem,* 87(18):9186-9193) or ion mobility (Doneanu et al., 2015, *Anal Chem,* 87(20):10283-10291). Other strategies include Protein A depletion (Madsen et al., 2015, *mAbs,* 7(6):1128-1137; Thompson et al., 2014, *Rapid Commun Mass Spectrom,* 28(8):855-860; Johnson et al., 2020, *Anal Chem,* 92(15):10478-10484) or native digestion (Huang et al., 2017, *Anal Chem,* 89(10):5436-5444) to remove therapeutic proteins in sample preparation steps (Madsen et al.; Huang et al.). In addition, chromatographic separation can be performed to resolve HCPs and therapeutic proteins before sample preparation. Examples of these methods include HCP analysis of reverse-phase HPLC fractionations (Bomans et al., 2013, *PLoS ONE,* 8(11):e81639), strong-cation exchange (SCX) fractionations (Soderquist et al., 2015, *Biotechnol Prog,* 31(4):983-989), and hydrophilic interaction liquid chromatography (HILIC) fractionations (Wang et al., 2020, *Anal Chem,* 92(15):10327-10335).

While many characterization methods focus on the aggregates of protein products as a causative mechanism of product issues related to HMW species, profiling of HCP impurities in HMW fractions has seldom been conducted (Xu et al., 2021, *J Pharm Sci,* 110(10):3403-3409). Therefore, a need exists for characterization of HCPs in biotherapeutic products, in particular the distribution of HCPs in fractions separated by size.

The Examples set forth below demonstrate several surprising findings that are important for development and manufacture of a biotherapeutic product. It was surprisingly found that a size exclusion chromatography (SEC) analytical method could be used for HCP identification with comparable or superior sensitivity and specificity compared to alternative methods. It was further surprisingly found that SEC analysis using a denaturing mobile phase compared to a non-denaturing mobile phase can be used to characterize binding of an HCP to a protein of interest, and further to generate a binding profile for all detected HCPs in a sample. Additionally, it was surprisingly found that a surfactant-assisted method with acid precipitation could further enhance detection, identification, and characterization of HCPs.

Relatedly, it was surprisingly found that a HMW fraction of a biotherapeutic product may include a high abundance of HCPs, and said HCPs selectively interact with particular HMW species, as opposed to eluting at an early SEC retention time based on their own size. It was also surprisingly found that samples, such as total biotherapeutic product DS, that include an unacceptably high abundance of HCPs may have a large percentage of those HCPs in LMW or HMW fractions. Finally, it was found that, even when using the same purification process, the identity and quantity of HCPs in total drug substance and in HMW fractions varied widely across different biotherapeutic products. These findings illuminate a potential mechanism of deleterious activity in the HMW species of a biotherapeutic product, which may include a high abundance of HCPs in a manner that is specific to the particular product. These findings also demonstrate the utility of a novel approach to the production of a biotherapeutic product, including determining whether the HMW fraction of the specific product contains a high abundance of problematic HCPs, and, if so, using SEC to remove HCPs that interact with HMW species, thereby improving the qualities of the product, for example stability and immunogenicity.

This disclosure provides a method for identifying, quantifying, and characterizing HCPs in a sample, for example a drug substance or a HMW fraction of a biotherapeutic product, and for removal of said HCPs in order to improve the production process of a biotherapeutic product. The examples set for below describe, for example, the use of native digestion to characterize HCPs in enriched HMW from drug substance (DS). More HCPs are identified in enriched HMW fractions than total DS across five studied mAbs, thus demonstrating that SEC can potentially be used as a fractionation strategy to enhance HCP detection. Some frequently identified and problematic HCPs were present at higher levels in the enriched HMW fractions than total DS, thus indicating that certain HCPs may preferentially interact with HMW species in biotherapeutic products. The most abundant HCP from mAb1, C-C motif chemokine, was substantially enriched in the HMW fraction. Therefore, further studies were conducted on HCP profiles of enriched dimer and enriched very HMW (vHMW) fractions to pinpoint the fraction associated with C-C motif chemokine. The association of C-C motif chemokine with mAb1 was attributed specifically to the mAb1 dimer. Finally, HMW species were removed from mAb1 by SEC, and MS quantification was performed to determine the C-C motif chemokine levels in HMW, monomer, and LMW fractions.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described.

The terms "a" and "an" should be understood to mean "at least one" and the terms "about" and "approximately" should be understood to permit standard variation as would be understood by those of ordinary skill in the art and where ranges are provided, endpoints are included. As used herein, the terms "include," "includes," and "including" are meant to be non-limiting and are understood to mean "comprise," "comprises," and "comprising" respectively.

As used herein, the terms "protein" and "protein of interest" can include any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptide or polypeptide" refers to a non-naturally occurring peptide or polypeptide. Synthetic peptides or polypeptides can be synthesized, for example, using an automated polypeptide synthesizer. Various solid-phase peptide synthesis methods are known to those of skill in the art. A protein may comprise one or multiple polypeptides to form a single functioning biomolecule. A protein can include antibody fragments, nanobodies, recombinant antibody chimeras, cytokines, chemokines, peptide hormones, and the like. Proteins of interest can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. Proteins may be produced using recombinant cell-based production systems, such as the insect baculovirus system, yeast systems (e.g., *Pichia* sp.), mammalian systems (e.g., CHO cells and CHO derivatives like CHO-K1 cells). For a recent review discussing bio-therapeutic proteins and their production, see Ghaderi et al., "Production platforms for biotherapeutic glycoproteins. Occurrence, impact, and challenges of non-human sialylation" (Darius Ghaderi et al., *Production platforms for biotherapeutic glycoproteins. Occurrence, impact, and challenges of non-human sialylation,* 28 Biotechnology and Genetic Engineering Reviews 147-176 (2012), the entire teachings of which are herein incorporated by reference). In some exemplary embodiments, proteins comprise modifications, adducts, and other covalently linked moieties. These modifications, adducts and moieties include, for example, avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as globular proteins and fibrous proteins; conjugated proteins, such as nucleoproteins, glycoproteins, mucoproteins, chromoproteins, phosphoproteins, metalloproteins, and lipoproteins; and derived proteins, such as primary derived proteins and secondary derived proteins. Non-limiting examples of a protein or a pharmaceutical protein product can include a recombinant protein, an antibody, a bispecific antibody, a multispecific antibody, an antibody fragment, a monoclonal antibody, a fusion protein, an scFv and combinations thereof.

As used herein, the term "recombinant protein" refers to a protein produced as the result of the transcription and translation of a gene carried on a recombinant expression vector that has been introduced into a suitable host cell. In certain exemplary embodiments, the recombinant protein can be an antibody, for example, a chimeric, humanized, or fully human antibody. In certain exemplary embodiments, the recombinant protein can be an antibody of an isotype selected from group consisting of. IgG (e.g., IgG1, IgG2, IgG3, IgG4), IgM, IgA1, IgA2, IgD, or IgE. In certain exemplary embodiments, the antibody molecule is a full-length antibody (e.g., an IgG1 or IgG4 immunoglobulin), or the antibody can be a fragment (e.g., an Fc fragment or a Fab fragment).

The term "antibody," as used herein, includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FRs). Each VH and VL is composed of three complementarity determining regions and four framework regions, arranged from amino-terminus to carboxy-terminus in the following order: FR1, CDR1, FR2, CDR2, FR3, CDR3, and FR4. In different embodiments of the invention, the framework regions of the anti-big-ET-1 antibody (or antigen-binding portion thereof) may be identical to the human germline sequences or may be naturally or artificially modified. An amino acid consensus sequence may be defined based on a side-by-side analysis of two or more complementarity determining regions. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, for example, from full antibody molecules using any suitable standard techniques such as proteolytic digestion or recombinant genetic engineering techniques involving the manipulation and expression of DNA encoding antibody variable and optionally constant domains. Such DNA is known and/or is readily available from, for example, commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, an F(ab')2 fragment, an scFv fragment, an Fv fragment, a dsFv diabody, a dAb fragment, an Fd' fragment, an Fd fragment, and an isolated complementarity determining region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment comprises a sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively, or additionally, an antibody fragment may be wholly or partially synthetically produced. An antibody fragment may optionally comprise a single-chain antibody fragment. Alternatively, or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The term "bispecific antibody" includes an antibody capable of selectively binding two or more epitopes. Bispecific antibodies generally comprise two different heavy chains, with each heavy chain specifically binding a different epitope-either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions and such sequences can be expressed in a cell that expresses an immunoglobulin light chain.

A typical bispecific antibody has two heavy chains, each having three heavy chain complementarity determining regions, followed by a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding of one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bispecific antibodies (bsAbs) can have different formats such as, but not limited to, triomab, knobs-into-holes IgG (KiH IgG), crossMab, orth-Fab IgG, Dual-variable domains Ig (DVD-Ig), two-in-one or dual action Fab (DAF), IgG-single-chain Fv (IgG-scFv), or k-bodies. The non-IgG-like different formats include tandem scFvs, diabody format, single-chain diabody, tandem diabodies (TandAbs), Dual-affinity retargeting molecule (DART), DART-Fc, nanobodies, or antibodies produced by the dock-and-lock (DNL) method (Gaowei Fan, Zujian Wang and Mingju Hao, Bispecific Antibodies and Their Applications, 8 Journal of Hematology & Oncology 130; Dafne Müller and Roland E. Kontermann, Bispecific Antibodies, Handbook of Therapeutic Antibodies 265-310 (2014), the entire teachings of which are herein incorporated). The methods of producing bsAbs are not limited to quadroma technology based on the somatic fusion of two different hybridoma cell lines, chemical conjugation, which involves chemical cross-linkers, and genetic approaches utilizing recombinant DNA technology.

As used herein, "multispecific antibody" refers to an antibody with binding specificities for at least two different antigens. While such molecules normally will only bind two antigens (e.g., bispecific antibodies/bsAbs), antibodies with additional specificities such as trispecific antibodies and KiH trispecific antibodies can also be addressed by the system and method disclosed herein.

The term "monoclonal antibody" as used herein, is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art, including the use of hybridoma, recombinant, and phage display technologies, or a combination thereof.

As used herein, the term "host-cell protein" (HCP) includes protein derived from a host cell in the production of a recombinant protein. Host-cell protein can be a process-related impurity, which can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables. In some exemplary embodiments, the types of host-cell proteins in the composition can be at least two. In some exemplary embodiments, a host-cell protein may bind to a biotherapeutic. In some exemplary embodiments, a host-cell protein may have strong, weak, or no binding to a biotherapeutic. In some exemplary embodiments, a host cell protein may preferentially bind to a particular form of a biotherapeutic, for example an aggregate, a multimer, dimer, a monomer, a post-translationally modified form, a truncated form, or a fragment of a biotherapeutic.

The presence of a host cell protein in a biotherapeutic product may be considered to be a higher or lower risk based on a number of measurable factors. One such factor is the concentration or abundance (quantity) of an HCP impurity in a biotherapeutic product. An HCP may have no discernible impact at a low enough abundance, as measured by, for example, ELISA or mass spectrometry. The level at which an HCP may present a considerable risk, which may be considered an unacceptable level in a product and may be monitored as a critical quality attribute (CQA), may depend on the specific identity of the HCP. Particular HCPs may be known to present a risk at a particular level, for example depending on the level of enzymatic activity of an HCP that is an enzyme.

Relatedly, the criticality of the presence of an HCP may depend on the function of that HCP, in particular in relation to the components of the biotherapeutic product. For example, an HCP lipase that may or is known to degrade polysorbate that is present in the biotherapeutic product of interest may be closely monitored and may have a low threshold for how much of the HCP impurity can be allowed in the biotherapeutic product. Other HCPs of particular concern may be, for example, proteases that may or are known to degrade a protein of interest in the biotherapeutic product, or immunogenic HCPs that may or are known to cause an immune reaction when administered to a subject.

Using the method of the present invention, a person skilled in the art may evaluate the abundance, distribution, and/or identity of an HCP impurity in the context of the biotherapeutic product of interest to determine if the HCP impurity is an HCP impurity of concern, and based on that determination may use chromatographic or other separation methods to remove the impurity when producing the biotherapeutic product.

In some exemplary embodiments, a sample can comprise at least one high-abundance protein or peptide and at least one HCP. In some exemplary embodiments, a concentration of the at least one high-abundance protein or peptide can be at least about 1000 times, 10,000 times, 100,000 times or 1,000,000 times higher than a concentration of the at least one HCP. Another way of expressing the relative concentrations is, for example, in parts per million (ppm). It should be understood that when using ppm to describe the concentration of a low-abundance protein or peptide, such as an HCP, in a sample that includes a high-abundance protein or peptide, such as a therapeutic protein, ppm is measured relative to the concentration of the high-abundance protein or peptide. In some exemplary embodiments, a concentration of the at least one HCP can be less than about 1000 ppm, less than about 100 ppm, less than about 10 ppm, or less than about 1 ppm.

In some exemplary embodiments, a sample can comprise at least one protein of interest and at least one HCP. In some exemplary embodiments, a sample can comprise at least one protein of interest and at least one HCP, wherein the protein of interest is larger in size than the HCP. In some exemplary embodiments, a sample can comprise at least one protein of interest and at least one HCP, wherein the protein of interest is larger in size than the HCP such that they can be separated using SEC. A protein of interest may be, for example, larger than 50 kilodaltons (kDa), larger than 100 kDa, larger than 150 kDa, between about 50 kDa and about 250 kDa, between about 100 kDa and about 250 kDa, between about 100 kDa and about 200 kDa, between about 150 kDa and about 250 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 kDa, about 230 kDa, about 240 kDa, about 250 kDa, about 260 kDa, about 270 kDa, about 280 kDa, about 290 kDa, about 300 kDa, about 310 kDa, about 320 kDa, about 330 kDa, about 340 kDa, about 350 kDa, about 360 kDa, about 370 kDa, about 380 kDa, about 390 kDa, about 400 kDa, about 410 kDa, about 420 kDa, about 430 kDa, about 440 kDa, about 450 kDa, about 460 kDa, about 470 kDa, about 480 kDa, about 490 kDa, about 500 kDa, about 510 kDa, about 520 kDa, about 530 kDa, about 540 kDa, about 550 kDa, about 560 kDa, about 570 kDa, about 580 kDa, about 590 kDa, or about 600 kDa.. A host cell protein may be about 1 kDa, about 2 kDa, about 3 kDa, about 4 kDa, about 5 kDa, about 6 kDa, about 7 kDa, about 8 kDa, about 9 kDa, about 10 kDa, about 15 kDa, about 20 kDa, about 25 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 kDa, about 230 kDa, about 240 kDa, about 250 kDa, about 260 kDa, about 270 kDa, about 280 kDa, about 290 kDa, about 300 kDa, about 310 kDa, about 320 kDa, about 330 kDa, about 340 kDa, about 350 kDa, about 360 kDa, about 370 kDa, about 380 kDa, about 390 kDa, about 400 kDa, about 410 kDa, about 420 kDa, about 430 kDa, about 440 kDa, about 450 kDa, about 460 kDa, about 470 kDa, about 480 kDa, about 490 kDa, about 500 kDa, about 510 kDa, about 520 kDa, about 530 kDa, about 540 kDa, about 550 kDa, about 560 kDa, about 570 kDa, about 580 kDa, about 590 kDa, or about 600 kDa.

As used herein, a "protein pharmaceutical product," "biopharmaceutical product" or "biotherapeutic" includes an active ingredient which can be fully or partially biological in nature. In one aspect, the protein pharmaceutical product can comprise a peptide, a protein, a fusion protein, an antibody, an antigen, vaccine, a peptide-drug conjugate, an antibody-drug conjugate, a protein-drug conjugate, cells, tissues, or combinations thereof. In another aspect, the protein pharmaceutical product can comprise a recombinant, engineered, modified, mutated, or truncated version of a peptide, a protein, a fusion protein, an antibody, an antigen, vaccine, a peptide-drug conjugate, an antibody-drug conjugate, a protein-drug conjugate, cells, tissues, or combinations thereof.

A protein, pharmaceutical protein product, biopharmaceutical product or biotherapeutic can be produced from mammalian cells. The mammalian cells can be of human origin or non-human origin, and can include primary epithelial cells (e.g., keratinocytes, cervical epithelial cells, bronchial epithelial cells, tracheal epithelial cells, kidney epithelial cells and retinal epithelial cells), established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LSI80 cells, LS174T cells, NCI-H-548 cells, RPM12650 cells, SW-13 cells, T24 cells, WI-28 VA13, 2RA cells, WISH cells, BS-C-I cells, LLC-MK2 cells, Clone M-3 cells, 1-10 cells, RAG cells, TCMK-1 cells, Y-1 cells, LLC-PKi cells, PK(15) cells, GHi cells, GH3 cells, L2 cells, LLC-RC 256 cells, MHiCi cells, XC cells, MDOK cells, VSW cells, and TH-I, B1 cells, BSC-1 cells, RAf cells, RK-cells, PK-15 cells or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, Midi cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDMiC3 cells, KLN205 cells, McCoy cells, Mouse L cells, Strain 2071 (Mouse L) cells, L-M strain (Mouse L) cells, L-MTK' (Mouse L) cells, NCTC clones 2472 and 2555, SCC-PSA1 cells, Swiss/3T3 cells, Indian muntjac cells, SIRC cells, Cn cells, and Jensen cells, Sp2/0, NS0, NS1 cells or derivatives thereof).

As used herein, a "sample" can be obtained from any step of a bioprocess, such as cell culture fluid (CCF), harvested cell culture fluid (HCCF), any step in the downstream processing, drug substance (DS), or a drug product (DP) comprising the final formulated product. In some specific exemplary embodiments, the sample can be selected from any step of the downstream process of clarification, chromatographic production, or filtration.

In some exemplary embodiments, a sample including a protein of interest can be prepared prior to LC-MS analysis. Preparation steps can include denaturation, alkylation, dilution, digestion, precipitation, centrifugation, buffer exchange and desalting. In some exemplary embodiments, precipitation can be mediated by an acid. In some preferred exemplary embodiments, precipitation can be mediated by trifluoroacetic acid.

As used herein, the term "protein alkylating agent" or "alkylation agent" refers to an agent used for alkylating certain free amino acid residues in a protein. Non-limiting examples of protein alkylating agents are iodoacetamide (IOA/IAA), chloroacetamide (CAA), acrylamide (AA), N-ethylmaleimide (NEM), methyl methanethiosulfonate (MMTS), and 4-vinylpyridine or combinations thereof.

As used herein, "protein denaturing" or "denaturation" can refer to a process in which the three-dimensional shape of a molecule is changed from its native state. Protein denaturation can be carried out using a protein denaturing agent. Non-limiting examples of a protein denaturing agent include heat, high or low pH, reducing agents like DTT, or exposure to chaotropic agents. Several chaotropic agents can be used as protein denaturing agents. Chaotropic solutes increase the entropy of the system by interfering with intramolecular interactions mediated by non-covalent forces such as hydrogen bonds, van der Waals forces, and hydrophobic effects. Non-limiting examples of chaotropic agents include butanol, ethanol, guanidinium chloride, lithium perchlorate, lithium acetate, magnesium chloride, phenol, propanol, sodium dodecyl sulfate, thiourea, N-lauroylsarcosine, urea, and salts thereof. In some exemplary embodiments, denaturing agents may be used in the mobile phase in a chromatography analysis. In some exemplary embodiments, a denaturing agent used in a mobile phase may be acetonitrile. In some exemplary embodiments, a denaturing agent used in a mobile phase may be a surfactant.

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion. Digestion of a protein into constituent peptides can produce a "peptide digest" that can further be analyzed using peptide mapping analysis.

As used herein, the term "digestive enzyme" refers to any of a large number of different agents that can perform digestion of a protein. Non-limiting examples of hydrolyzing agents that can carry out enzymatic digestion include protease from *Aspergillus saitoi*, elastase, subtilisin, protease XIII, pepsin, trypsin, Tryp-N, chymotrypsin, aspergillopepsin I, LysN protease (Lys-N), LysC endoproteinase (Lys-C), endoproteinase Asp-N(Asp-N), endoproteinase Arg-C(Arg-C), endoproteinase Glu-C(Glu-C) or outer membrane protein T (OmpT), immunoglobulin-degrading enzyme of *Streptococcus pyogenes* (IdeS), thermolysin, papain, pronase, V8 protease or biologically active fragments or homologs thereof or combinations thereof. For a recent review discussing the available techniques for protein digestion see Switazar et al., "Protein Digestion: An Overview of the Available Techniques and Recent Developments" (Linda Switzar, Martin Giera & Wilfried M. A. Niessen, Protein Digestion: An Overview of the Available Techniques and Recent Developments, 12 JOURNAL OF PROTEOME RESEARCH 1067-1077 (2013)).

Conventional methods use a digestive enzyme in conditions and concentrations sufficient to completely digest all protein in a sample prior to LC-MS analysis. The present disclosure finds that identification and characterization of HCPs can be improved through limited digestion, meaning that digestive enzymes are used in conditions such that proteins in a sample are not completely digested. In some exemplary embodiments, a ratio of digestive enzyme to substrate, for example enzyme to protein if the enzyme is a protease and the substrate is a protein or mix of proteins, is selected to ensure limited digestion. In some exemplary embodiments, a ratio of digestive enzyme to substrate is less than about 1:100, less than about 1:200, less than about 1:300, less than about 1:400, less than about 1:500, less than about 1:600, less than about 1:700, less than about 1:800, less than about 1:900, less than about 1:1000, less than about 1:2000, less than about 1:3000, less than about 1:4000, less than about 1:5000, less than about 1:6000, less than about 1:7000, less than about 1:8000, less than about 1:9000, less than about 1:10000, between about 1:100 and about 1:10000, between about 1:200 and about 1:2000, about 1:200, about 1:400, about 1:500, about 1:1000, about 1:2000, about 1:2500, or about 1:10000.

As used herein, the term "protein reducing agent" or "reduction agent" refers to the agent used for reduction of disulfide bridges in a protein. Non-limiting examples of protein reducing agents used to reduce a protein are dithiothreitol (DTT), 8-mercaptoethanol, Ellman's reagent, hydroxylamine hydrochloride, sodium cyanoborohydride, tris(2-carboxyethyl)phosphine hydrochloride (TCEP-HCl), or combinations thereof. A conventional method of protein analysis, reduced peptide mapping, involves protein reduction prior to LC-MS analysis. In contrast, non-reduced peptide mapping omits the sample preparation step of reduction in order to preserve endogenous disulfide bonds.

As used herein, the term "dissociation reagent" refers to a class of molecules that can modulate protein-protein interactions, stabilize a molecule in an unbound state, or both. In some exemplary embodiments, a dissociation reagent can destabilize an interaction between at least one protein of interest and at least one HCP. In some exemplary embodiments, a dissociation reagent can comprise a surfactant, a detergent or both.

As used herein, the term "surfactant" refers to a class of molecules comprising a hydrophobic "head" domain and hydrophilic "tail" domain. A surfactant may be used, for example, to modulate the interactions of solvents and solutes, or to modulate protein-protein interactions. A surfactant may be, for example, a phase transfer surfactant, an ionic surfactant, an anionic surfactant, a cationic surfactant, or combinations thereof.

An exemplary type of surfactant useful in the method of the present invention is a detergent. Non-limiting examples of detergents include anionic detergents, such as salts of deoxycholic acid, 1-heptanesulfonic acid, N-laurylsarcosine, lauryl sulfate, 1-octane sulfonic acid, taurocholic acid, and sodium lauroyl sarcosinate (SLS); cationic detergents such as benzalkonium chloride, cetylpyridinium, methylbenzethonium chloride, and decamethonium bromide; zwitterionic detergents such as alkyl betaines, alkyl amidoalkyl betaines, N-dodecyl-N,N-dimethyl-3-ammonio-1-propanesulfonate, and phosphatidylcholine; and non-ionic detergents such as n-decyl α-D-glucopyranoside, n-decyl β-D-maltopyranoside, n-dodecyl β-D-maltoside, n-octyl β-D-glucopyranoside, sorbitan esters, n-tetradecyl β-D-maltoside, tritons, Nonidet-P-40, Poloxamer 188, and any of the Tween group of detergents; sodium lauryl sulfate (SLS);

and sodium deoxycholate (SDC). A detergent may be a combination of multiple surfactants. Detergents may be denaturing or non-denaturing with respect to protein structure. In some exemplary embodiments, a preferred detergent is a denaturing detergent. In some exemplary embodiments, a preferred detergent is SLS, SDC, or a combination thereof.

As used herein, the term "liquid chromatography" refers to a process in which a biological/chemical mixture carried by a liquid can be separated into components as a result of differential distribution of the components as they flow through (or into) a stationary liquid or solid phase. Non-limiting examples of liquid chromatography include reverse phase liquid chromatography, ion-exchange chromatography, size exclusion chromatography, affinity chromatography, hydrophobic interaction chromatography, hydrophilic interaction chromatography, or mixed-mode chromatography. In some aspects, a sample containing the at least one protein of interest or peptide digest can be subjected to any one of the aforementioned chromatographic methods or a combination thereof. Analytes separated using chromatography will feature distinctive retention times, reflecting the speed at which an analyte moves through the chromatographic column. Analytes may be compared using a chromatogram, which plots retention time on one axis and measured signal on another axis, where the measured signal may be produced from, for example, UV detection or fluorescence detection.

Size exclusion chromatography (SEC) or gel filtration relies on the separation of components as a function of their molecular size. Separation depends on the amount of time that the substances spend in the porous stationary phase as compared to time in the fluid. The probability that a molecule will reside in a pore depends on the size of the molecule and the pore. In addition, the ability of a substance to permeate into pores is determined by the diffusion mobility of macromolecules which is higher for small macromolecules. Very large macromolecules may not penetrate the pores of the stationary phase at all; and, for very small macromolecules the probability of penetration is close to unity. While components of larger molecular size move more quickly past the stationary phase, components of small molecular size have a longer path length through the pores of the stationary phase and are thus retained longer in the stationary phase.

Analytes eluting from an SEC column may be separated into fractions based on elution time. For example, analytes eluting earlier than the functional form of a protein of interest, for example the monomeric form, may be broadly categorized as high molecular weight (HMW) species. A HMW fraction may be further subdivided into, for example, a very high molecular weight (vHMW) fraction and a dimer fraction (representing the elution time of a dimer of the protein of interest). Analytes eluting later than the functional form of a protein of interest may be broadly categorized as low molecular weight (LMW) species, and may be further subdivided into a LMW fraction and a later tail fraction.

The chromatographic material can comprise a size exclusion material wherein the size exclusion material is a resin or membrane. The matrix used for size exclusion is preferably an inert gel medium which can be a composite of cross-linked polysaccharides, for example, cross-linked agarose and/or dextran in the form of spherical beads. The degree of cross-linking determines the size of pores that are present in the swollen gel beads. Molecules greater than a certain size do not enter the gel beads and thus move through the chromatographic bed the fastest. Smaller molecules, such as detergent, protein, DNA and the like, which enter the gel beads to varying extent depending on their size and shape, are retarded in their passage through the bed. Molecules are thus generally eluted in the order of decreasing molecular size.

Porous chromatographic resins appropriate for size exclusion chromatography of viruses may be made of dextrose, agarose, polyacrylamide, or silica which have different physical characteristics. Polymer combinations can also be also used. Most commonly used are those under the tradename, "SEPHADEX" available from Amersham Biosciences. Other size exclusion supports from different materials of construction are also appropriate, for example Toyopearl 55F (polymethacrylate, from Tosoh Bioscience, Montgomery Pa.) and Bio-Gel P-30 Fine (BioRad Laboratories, Hercules, Calif.).

As used herein, the term "mass spectrometer" includes a device capable of identifying specific molecular species and measuring their accurate masses. The term is meant to include any molecular detector into which a polypeptide or peptide may be characterized. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization) or through separate processes. The choice of ion source depends on the application.

In some exemplary embodiments, the mass spectrometer can be a tandem mass spectrometer. As used herein, the term "tandem mass spectrometry" includes a technique where structural information on sample molecules is obtained by using multiple stages of mass selection and mass separation. A prerequisite is that the sample molecules be transformed into a gas phase and ionized so that fragments are formed in a predictable and controllable fashion after the first mass selection step. MS/MS, or $MS^2$, can be performed by first selecting and isolating a precursor ion ($MS^1$), and fragmenting it to obtain meaningful information. Tandem MS has been successfully performed with a wide variety of analyzer combinations. Which analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m z separation functions can be designed so that in one section of the instrument ions are selected, dissociated in an intermediate region, and the product ions are then transmitted to another analyzer for m/z separation and data acquisition. In tandem-in-time, mass spectrometer ions produced in the ion source can be trapped, isolated, fragmented, and m z separated in the same physical device.

The peptides identified by the mass spectrometer can be used as surrogate representatives of the intact protein and their post-translational modifications or other modifications. They can be used for protein characterization by correlating experimental and theoretical MS/MS data, the latter generated from possible peptides in a protein sequence database. The characterization includes, but is not limited, to sequencing amino acids of the protein fragments, determining protein sequencing, determining protein de novo sequencing, locating post-translational modifications, or identifying post-translational modifications, or comparability analysis, or combinations thereof.

In some exemplary aspects, the mass spectrometer can work on nanoelectrospray or nanospray. The term "nanoelectrospray" or "nanospray" as used herein refers to electrospray ionization at a very low solvent flow rate, typically hundreds of nanoliters per minute of sample solution or lower, often without the use of an external solvent delivery. The electrospray infusion setup forming a nanoelectrospray can use a static nanoelectrospray emitter or a dynamic nanoelectrospray emitter. A static nanoelectrospray emitter performs a continuous analysis of small sample (analyte) solution volumes over an extended period of time. A dynamic nanoelectrospray emitter uses a capillary column and a solvent delivery system to perform chromatographic separations on mixtures prior to analysis by the mass spectrometer.

In some exemplary embodiments, mass spectrometry can be performed under native conditions. As used herein, the term "native conditions" can include performing mass spectrometry under conditions that preserve non-covalent interactions in an analyte. For a detailed review on native MS, refer to the review: Elisabetta Boeri Erba & Carlo Petosa, The emerging role of native mass spectrometry in characterizing the structure and dynamics of macromolecular complexes, 24 PROTEIN SCIENCE 1176-1192 (2015).

As used herein, the term "database" refers to a compiled collection of protein sequences that may possibly exist in a sample, for example in the form of a file in a FASTA format. Relevant protein sequences may be derived from cDNA sequences of a species being studied. Public databases that may be used to search for relevant protein sequences included databases hosted by, for example, Uniprot or Swiss-prot. Databases may be searched using what are herein referred to as "bioinformatics tools." Bioinformatics tools provide the capacity to search uninterpreted MS/MS spectra against all possible sequences in the database(s), and provide interpreted (annotated) MS/MS spectra as an output. Non-limiting examples of such tools are Mascot (www.matrixscience.com), Spectrum Mill (www.chem.agilent.com), PLGS (www.waters.com), PEAKS (www.bioinformaticssolutions.com), Proteinpilot (download.appliedbiosystems.com/proteinpilot), Phenyx (www.phenyx-ms.com), Sorcerer (www.sagenresearch.com), OMSSA (www.pubchem.ncbi.nlm.nih.gov/omssa/), X!Tandem (www.thegpm.org/TANDEMI), Protein Prospector (prospector.ucsf.edu/prospector/mshome.htm), Byonic (www.proteinmetrics.com/products/byonic) or Sequest (fields.scripps.edu/sequest).

This disclosure provides a method for identifying HCP impurities in a sample. In some exemplary embodiments, the method comprises: (a) subjecting a sample including at least one protein of interest and at least one HCP impurity to size exclusion chromatography (SEC) analysis to produce fractions, and (b) subjecting said fractions to LC-MS analysis to identify said at least one HCP impurity.

In some exemplary embodiments, an amount of protein loaded onto the SEC column may be between about 0.5 mg and about 20 mg, between about 1 mg and about 10 mg, between about 8 mg and about 12 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg.

In some exemplary embodiments, a mobile phase for the SEC analysis may comprise acetonitrile. In some exemplary embodiments, a concentration of said acetonitrile may be between about 5% v/v and about 20% v/v, between about 10% v/v and about 20% v/v, between about 15% v/v and about 20% v/v, about 5% v/v, about 6% v/v, about 7% v/v, about 8% v/v, about 9% v/v, about 10% v/v, about 11% v/v, about 12% v/v, about 13% v/v, about 14% v/v, about 15% v/v, about 16% v/v, about 17% v/v, about 18% v/v, about 19% v/v, or about 20% v/v.

In some exemplary embodiments, a mobile phase for the SEC analysis may comprise at least one surfactant. In some exemplary embodiments, a concentration of said at least one surfactant may be between about 6 mM and about 36 mM, between about 10 mM and about 20 mM, between about 12 mM and about 24 mM, between about 10 mM and about 14 mM, between about 20 mM and about 28 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, or about 36 mM.

In some exemplary embodiments, the at least one surfactant may be a detergent. In some exemplary embodiments, a sample may be incubated in a detergent. In some exemplary embodiments, a sample may be incubated in a detergent prior to acid precipitation. In some exemplary embodiments, the time a sample is incubated in a detergent may be between about 5 minutes and about 120 minutes, between about 15 minutes and about 90 minutes, between about 30 minutes and about 75 minutes, between about 45 minutes and about 60 minutes, about 5 minutes, about 15 minutes, about 30 minutes, about 45 minutes, about 60 minutes, about 75 minutes, about 90 minutes, about 105 minutes or about 120 minutes. In some exemplary embodiments, the at least one detergent may be selected from a group consisting of sodium deoxycholate, sodium lauroyl sarcosinate, and a combination thereof. In some exemplary embodiments, a concentrate of sodium deoxycholate may be between about 6 mM and about 120 mM, about 20 mM and about 120 mM, about 20 mM and about 60 mM, about 40 mM and about 60 mM, about 6 mM and about 36 mM, between about 10 mM and about 20 mM, between about 12 mM and about 24 mM, between about 10 mM and about 14 mM, between about 20 mM and about 28 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM. about 37 mM, about 38 mM, about 39 mM, about 40 mM, about 41 mM, about 42 mM, about 43, mM, about 44 mM, about 45 mM, about 46 mM, about 47 mM, about 48 mM, about 49 mM, about 50 mM, about 55 mM, about 60 mM, about 65 mM, about 70 mM, about 75 mM, about 80 mM, about 85 mM, about 90 mM, about 95, mM, about 100 mM, about 105 mM, about 110 mM, about 115 mM or about 120 mM. In some exemplary embodiments, a concentration of sodium lauroyl sarcosinate may be between about 6 mM and about 120 mM, about 20 mM and about 120 mM, about 20 mM and about 60 mM, about 40 mM and about 60 mM, about 6 mM and about 36 mM, between about 10 mM and about 20 mM, between about 12 mM and about 24 mM, between about 10 mM and about 14 mM, between about 20 mM and about 28 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM. about 37 mM, about 38 mM, about 39 mM, about 40 mM, about 41 mM, about 42 mM, about 43, mM, about 44 mM, about 45 mM, about 46 mM, about 47 mM, about 48 mM, about 49 mM, about 50 mM, about 55 mM, about 60 mM, about 65 mM, about 70 mM, about 75 mM, about 80 mM, about 85 mM, about 90 mM, about 95, mM, about 100 mM, about 105 mM, about 110 mM, about 115 mM or about 120 mM.

In some exemplary embodiments, the method may further comprise subjecting the fractions to enzymatic digestion prior to LC-MS analysis. In some exemplary embodiments, the enzymatic digestion may be performed by contacting the fractions to trypsin. In some exemplary embodiments, the enzymatic digestion may be performed by contacting the fractions to a digestive enzyme at an enzyme to protein ratio of between about 1:100 and about 1:2000, between about 1:100 and about 1:2000, about 1:50, about 1:100, about 1:150, about 1:200, about 1:300, about 1:400, about 1:500, about 1:600, about 1:700, about 1:800, about 1:900, about 1:1000, or about 1:2000.

In some exemplary embodiments, the method may further comprise subjecting the fractions to acid precipitation prior to LC-MS analysis. In some exemplary embodiments, the acid precipitation may comprise contacting the fractions to trifluoroacetic acid. In some exemplary embodiments, the acid precipitation may comprise centrifugation. In some exemplary embodiments, a concentration of trifluoroacetic acid may be between about 0.5% and about 20%, between about 1% and about 10%, between about 0.5% and about 5%, between about 1% and about 2%, about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19% or about 20%.

In some exemplary embodiments, the method may further comprise subjecting the fractions to buffer exchange. In some exemplary embodiments, the steps of the method may be in the order of SEC analysis, acid precipitation, buffer exchange, digestion, and LC-MS analysis. In some exemplary embodiments, the steps of the method may be in the order of SEC analysis, buffer exchange, digestion, and LC-MS analysis. In some exemplary embodiments, the steps of the method may be in the order of SEC analysis, buffer exchange, and LC-MS analysis. In some exemplary embodiments, the steps of the method may be in the order of acid precipitation, buffer exchange, digestion and liquid chromatography-mass spectrometry analysis. In some exemplary embodiments, the steps of the method may be in the order of acid precipitation, buffer exchange, digestion, desalting and liquid chromatography-mass spectrometry analysis. In some exemplary embodiments, acid precipitation may include centrifugation.

This disclosure also provides a method for characterizing the binding of a HCP impurity to a protein of interest. In some exemplary embodiments, the method comprises: (a) obtaining a sample including a protein of interest and at least one HCP impurity, (b) subjecting said sample to size exclusion chromatography (SEC) analysis using a non-denaturing mobile phase to produce native fractions; (c) subjecting said sample of (a) to SEC analysis using a denaturing mobile phase to produce denatured fractions; (d) subjecting said native fractions and said denatured fractions to LC-MS analysis to produce a native separation profile and a denatured separation profile of said at least one HCP impurity; and (e) comparing said native separation profile to said denatured separation profile to characterize the binding of said at least one HCP impurity to said protein of interest.

In some exemplary embodiments, an amount of protein loaded onto the SEC column may be between about 0.5 mg and about 20 mg, between about 1 mg and about 10 mg, between about 8 mg and about 12 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg.

In some exemplary embodiments, the denaturing mobile phase for the SEC analysis may comprise acetonitrile. In some exemplary embodiments, a concentration of said acetonitrile may be between about 5% v/v and about 20% v/v, between about 10% v/v and about 20% v/v, between about 15% v/v and about 20% v/v, about 5% v/v, about 6% v/v, about 7% v/v, about 8% v/v, about 9% v/v, about 10% v/v, about 11% v/v, about 12% v/v, about 13% v/v, about 14% v/v, about 15% v/v, about 16% v/v, about 17% v/v, about 18% v/v, about 19% v/v, or about 20% v/v.

In some exemplary embodiments, the denaturing mobile phase for the SEC analysis may comprise at least one surfactant. In some exemplary embodiments, a concentration of said at least one surfactant may be between about 6 mM and about 120 mM, about 20 mM and about 120 mM, about 20 mM and about 60 mM, about 40 mM and about 60 mM, about 6 mM and about 36 mM, between about 10 mM and about 20 mM, between about 12 mM and about 24 mM, between about 10 mM and about 14 mM, between about 20 mM and about 28 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM. about 37 mM, about 38 mM, about 39 mM, about 40 mM, about 41 mM, about 42 mM, about 43, mM, about 44 mM, about 45 mM, about 46 mM, about 47 mM, about 48 mM, about 49 mM, about 50 mM, about 55 mM, about 60 mM, about 65 mM, about 70 mM, about 75 mM, about 80 mM, about 85 mM, about 90 mM, about 95, mM, about 100 mM, about 105 mM, about 110 mM, about 115 mM or about 120 mM.

In some exemplary embodiments, the at least one surfactant may be a detergent. In some exemplary embodiments, the at least one detergent may be selected from a group consisting of sodium deoxycholate, sodium lauroyl sarcosinate, and a combination thereof. In some exemplary embodiments, a concentrate of sodium deoxycholate may be between about 6 mM and about 120 mM, about 20 mM and about 120 mM, about 20 mM and about 60 mM, about 40 mM and about 60 mM, about 6 mM and about 36 mM, between about 10 mM and about 20 mM, between about 12 mM and about 24 mM, between about 10 mM and about 14 mM, between about 20 mM and about 28 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM. about 37 mM, about 38 mM, about 39 mM, about 40 mM, about 41 mM, about 42 mM, about 43, mM, about 44 mM, about 45 mM, about 46 mM, about 47 mM, about 48 mM, about 49 mM, about 50 mM, about 55 mM, about 60 mM, about 65 mM, about 70 mM, about 75 mM, about 80 mM, about 85 mM, about 90 mM, about 95, mM, about 100 mM, about 105 mM, about 110 mM, about 115 mM or about 120 mM. In some exemplary embodiments, a concentration of sodium lauroyl sarcosinate may be between about 6 mM and about 120 mM, about 20 mM and about 120 mM, about 20 mM and about 60 mM, about 40 mM and about 60 mM, about 6 mM and about 36 mM, between about 10 mM and about 20 mM, between about 12 mM and about 24 mM, between about 10 mM and about 14 mM, between about 20 mM and about 28 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM. about 37 mM, about 38 mM, about 39 mM, about 40 mM, about 41 mM, about 42 mM, about 43, mM, about 44 mM, about 45 mM, about 46 mM, about 47 mM, about 48 mM, about 49 mM, about 50 mM, about 55 mM, about 60 mM, about 65 mM, about 70 mM, about 75 mM, about 80 mM, about 85 mM, about 90 mM, about 95, mM, about 100 mM, about 105 mM, about 110 mM, about 115 mM or about 120 mM.

In some exemplary embodiments, the method may further comprise subjecting the fractions to enzymatic digestion prior to LC-MS analysis. In some exemplary embodiments, the enzymatic digestion may be performed by contacting the fractions to trypsin. In some exemplary embodiments, the enzymatic digestion may be performed by contacting the fractions to a digestive enzyme at an enzyme to protein ratio of between about 1:100 and about 1:2000, between about 1:200 and about 1:2000, about 1:50, about 1:100, about 1:150, about 1:200, about 1:300, about 1:400, about 1:500, about 1:600, about 1:700, about 1:800, about 1:900, about 1:1000, or about 1:2000.

In some exemplary embodiments, the method may further comprise subjecting the fractions to acid precipitation prior to LC-MS analysis. In some exemplary embodiments, the acid precipitation may comprise contacting the fractions to trifluoroacetic acid. In some exemplary embodiments, a concentration of trifluoroacetic acid may be between about 0.5% and about 20%, between about 1% and about 10%, between about 0.5% and about 5%, between about 1% and about 2%, about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19% or about 20%.

In some exemplary embodiments, the method may further comprise subjecting the fractions to buffer exchange. In some exemplary embodiments, the method may further comprise desalting a peptide digest after digestion, before subjecting the peptide digest to liquid chromatography-mass spectrometry analysis or both. In some exemplary embodiments, the steps of the method may be in the order of SEC analysis, acid precipitation, buffer exchange, digestion, and LC-MS analysis. In some exemplary embodiments, the steps of the method may be in the order of SEC analysis, buffer exchange, digestion, and LC-MS analysis. In some exemplary embodiments, the steps of the method may be in the order of SEC analysis, buffer exchange, and LC-MS analysis.

This disclosure further provides a method for manufacturing a biotherapeutic product. In some exemplary embodiments, the method comprise (a) subjecting a first sample including at least one protein of interest and at least one host cell protein (HCP) impurity to size exclusion chromatography (SEC) analysis to produce a plurality of fractions; (b) subjecting said plurality of fractions to liquid chromatography-tandem mass spectrometry (LC-MS/MS) analysis to determine an identity and quantity of said at least one HCP impurity; (c) using said identity and quantity to determine whether said at least one HCP impurity is an impurity of concern in at least one of said plurality of fractions; (d) subjecting a second sample including said at least one protein of interest and said at least one HCP impurity to SEC analysis to produce a second plurality of fractions; and (e) using the determination of step (c), removing said at least one fraction in which said at least one HCP impurity is an impurity of concern from said plurality of fractions of step (d) to manufacture a biotherapeutic product.

In some exemplary embodiments, the protein of interest may be an antibody, a bispecific antibody, a monoclonal antibody, a fusion protein, an antibody-drug conjugate, an antibody fragment, or a protein pharmaceutical product. In some exemplary embodiments, the sample may include more than one protein of interest.

In some exemplary embodiments, the at least one HCP impurity may comprise a lipase, a protease, or a combination thereof. In some exemplary embodiments, the at least one HCP impurity may comprise C-C motif chemokine, carboxypeptidase, beta-hexosaminidase, inter-alpha-trypsin inhibitor heavy chain H5, lipoprotein lipase, peptidyl-prolyl cis-trans isomerase, cathepsin L1, annexin, legumain, complement C1r-A subcomponent, cornifin-A, peroxiredoxin, sialate O-acetylesterase, glutathione S-transferase mu 6, G-protein coupled receptor 56, cathepsin Z, annexin, lipase, metalloproteinase inhibitor 1, clusterin, fructose-biphosphate aldolase, fatty acid-binding protein, putative phospholipase B-like 2, acid ceramidase, cathepsin D, connective tissue growth factor, procollagen C-endopeptidase enhancer 1, neogenin, CD166 antigen, intercellular adhesion molecule 1, leucine-rich repeat transmembrane protein FLRT3, oncostatin-M specific receptor subunit beta, N-acetylglucosamine-6-sulfatase, ethanolamine-phosphate-cytidylyltransferase-like protein, vasorin, tyrosine-protein phosphatase non-receptor type 11, beta-hexosaminidase subunit alpha, or a combination thereof.

In some exemplary embodiments, the plurality of fractions may comprise a high molecular weight (HMW) fraction, a very high molecular weight (vHMW) fraction, a multimer fraction, a dimer fraction, a monomer fraction, a low molecular weight (LMW) fraction, a tail fraction, or a combination thereof.

In some exemplary embodiments, a fraction in which said at least one HCP impurity is an impurity of concern may be a HMW fraction, a total HMW fraction, a vHMW fraction, a dimer fraction, or a LMW fraction.

In some exemplary embodiments, an HCP may be primarily enriched in a dimer fraction. In some exemplary embodiments, an HCP may be primarily enriched in a vHMW fraction.

In some exemplary embodiments, an HCP may be present in a fraction at between about 1 ppm and about 10000 ppm; about 1 ppm, about 2 ppm, about 3 ppm, about 4 ppm, about 5 ppm, about 6 ppm, about 7 ppm, about 8 ppm, about 9 ppm, about 10 ppm, about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, about 600 ppm, about 700 ppm, about 800 ppm, about 900 ppm, about 1000 ppm, about 1100 ppm, about 1200 ppm, about 1300 ppm, about 1400 ppm, about 1500 ppm, about 1600 ppm, about 1700 ppm, about 1800 ppm, about 1900 ppm, about 2000 ppm, about 2100 ppm, about 2200 ppm, about 2300 ppm, about 2400 ppm, about 2500 ppm, about 3000 ppm, about 3500 ppm, about 4000 ppm, about 4500 ppm, about 5000 ppm, about 5500 ppm, about 6000 ppm, about 6500 ppm, about 7000 ppm, about 7500 ppm, about 8000 ppm, about 8500 ppm, about 9000 ppm, about 9500 ppm, or about 10000 ppm.

In some exemplary embodiments, an HCP may be determined to be an impurity of concern if it is present in the sample at between about 1 ppm and about 10000 ppm; about 1 ppm, about 2 ppm, about 3 ppm, about 4 ppm, about 5 ppm, about 6 ppm, about 7 ppm, about 8 ppm, about 9 ppm, about 10 ppm, about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, about 600 ppm, about 700 ppm, about 800 ppm, about 900 ppm, about 1000 ppm, about 1100 ppm, about 1200 ppm, about 1300 ppm, about 1400 ppm, about 1500 ppm, about 1600 ppm, about 1700 ppm, about 1800 ppm, about 1900 ppm, about 2000 ppm, about 2100 ppm, about 2200 ppm, about 2300 ppm, about 2400 ppm, about 2500 ppm, about 3000 ppm, about 3500 ppm, about 4000 ppm, about 4500 ppm, about 5000 ppm, about 5500 ppm, about 6000 ppm, about 6500 ppm, about 7000 ppm, about 7500 ppm, about 8000 ppm, about 8500 ppm, about 9000 ppm, about 9500 ppm, or about 10000 ppm.

In some exemplary embodiments, an HCP may be determined to be an impurity of concern if it is a lipase, a protease, and/or immunogenic.

In some exemplary embodiments, a percent of an HCP found in an HMW fraction may be between about 1% and about 100%, between about 20% and about 95%, between about 50% and about 90%, between about 60% and about 80%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100%.

In some exemplary embodiments, a sample may be subjected to sample preparation prior to SEC analysis. In some exemplary embodiments, these sample preparation steps may comprise buffer exchange, addition of at least one internal standard at a known concentration, reduction, alkylation, filtration, deglycosylation, acidification, or a combination thereof.

In some exemplary embodiments, a sample may be subjected to sample preparation prior to LC-MS/MS analysis. In some exemplary embodiments, these sample preparation steps may comprise addition of at least one internal standard at a known concentration, drying (for example using SpeedVac), concentration, denaturation, reduction, alkylation, digestion, acidification, or a combination thereof.

It is understood that the present invention is not limited to any of the aforesaid protein(s), protein(s) of interest, antibody(ies), host cell protein(s), protein alkylating agent(s), protein denaturing agent(s), protein reducing agent(s), digestive enzyme(s), sample(s), surfactant(s), detergent(s), chromatographic method(s), mass spectrometer(s), database (s), bioinformatics tool(s), pH, temperature(s), or concentration(s), and any protein(s), protein(s) of interest, antibody (ies), host cell protein(s), protein alkylating agent(s), protein denaturing agent(s), protein reducing agent(s), digestive enzyme(s), sample(s), surfactant(s), detergent(s), chromatographic method(s), mass spectrometer(s), database(s), bioinformatics tool(s), pH, temperature(s), or concentration(s) can be selected by any suitable means.

The present invention will be more fully understood by reference to the following examples. They should not, however, be construed as limiting the scope of the invention.

EXAMPLES

Example 1. Degradation of a Biotherapeutic

Figure 1B:
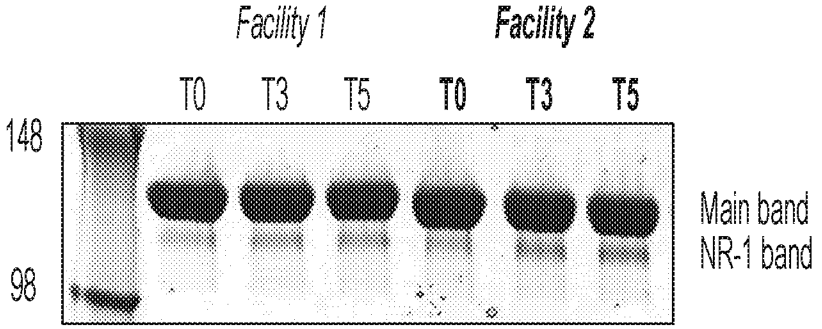
FIG. 1B shows degradation of aflibercept over time at 37° C. using SDS-PAGE, according to an exemplary embodiment.

Aflibercept was manufactured in two different production facilities, and stability of the final drug substance was assessed using an accelerated stability study at 25° C., as shown in FIG. 1A. Degradation was indicated by non-reduced band 1 (NR-1) fragment formation. This study revealed that degradation of aflibercept processed in Facility 2 was faster than in Facility 1. A confirmatory study was conducted by incubating aflibercept from each facility at 37° C. for 2 weeks, and visualizing degradation over time using SDS-PAGE, as shown in FIG. 1B. The results of the first study were confirmed.

Figure 2:
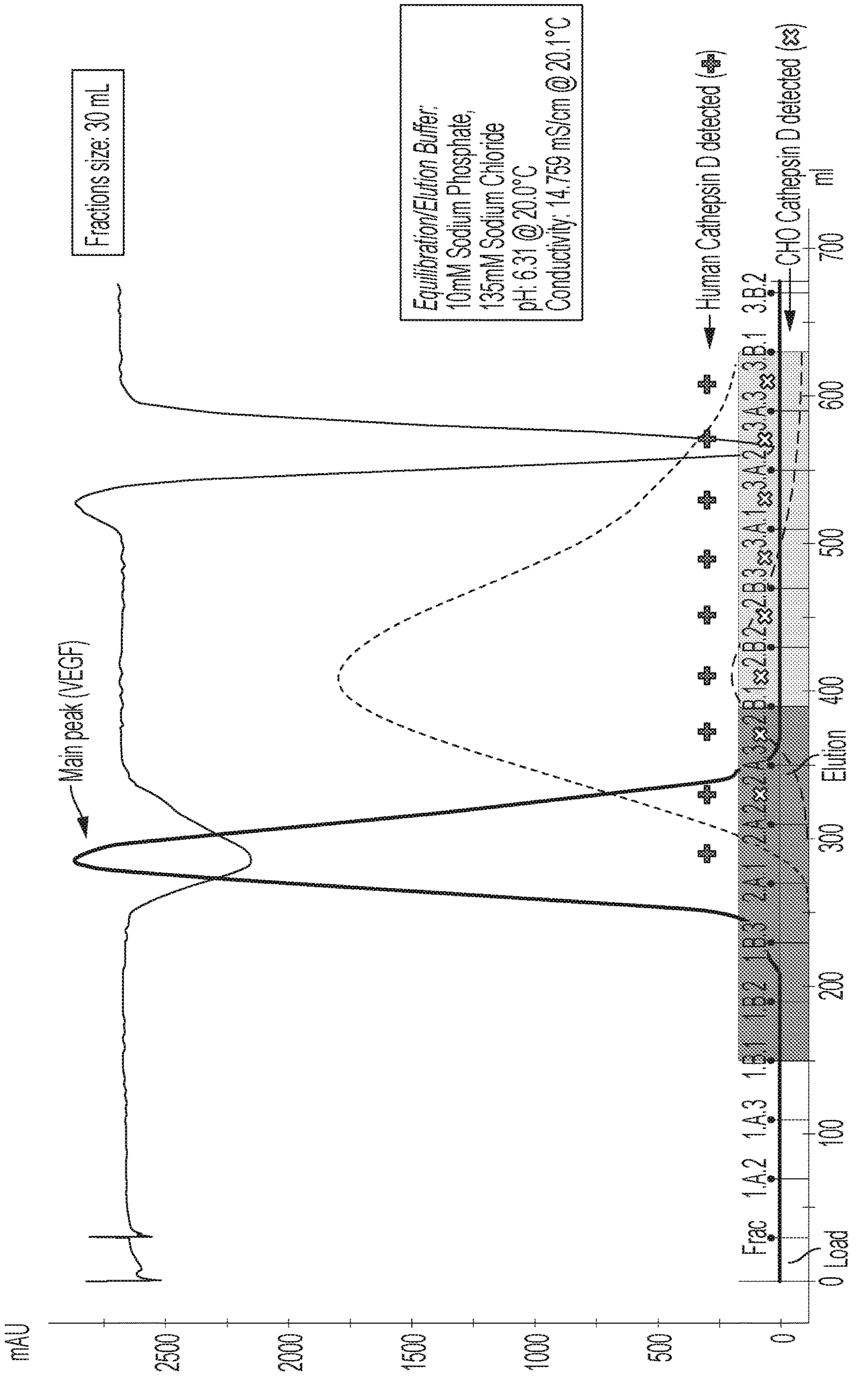
FIG. 2 shows SEC analysis of aflibercept drug substance revealing cathepsin D contamination, according to an exemplary embodiment.

In order to investigate the cause of biotherapeutic degradation, drug substance samples from Facility 2 were subjected to size exclusion chromatography (SEC) analysis to detect any contaminating HCPs, as shown in FIG. 2. Cathepsin D, a protease known to cause drug degradation, was detected in aflibercept samples from Facility 2.

Example 2. Size Exclusion Chromatography Method for Host Cell Protein Identification HCPs may end up in a drug substance due to binding to a biotherapeutic at some point in or throughout the purification process, and/or through co-purification in an unbound form. An SEC-based HCP characterization method was developed in order to determine a mechanism of HCP contamination in a sample, designed as an orthogonal separation method to enrich HCPs based on size. SEC has not previously been reported as an analytical method for HCP identification in process development.

Analytical scale separation of analytes from an exemplary therapeutic protein sample, mAb1, was conducted as follows. The concentration of the mAb was 25 mg/mL. An exemplary chromatography system suitable for this method is a Waters Acquity UPLC with fraction collector, with a Waters Xbridge Protein BEH200 Å SEC (7.8×300 mm, 3.5 μm) column. 500 μg of sample was injected over 2 replicates. Spiked-in standards used included BSA (66.5 kDa) and angiotensin (1 kDa). Mobile phases tested included a native (non-denaturing) mobile phase, a denaturing mobile phase with 2M urea, and a denaturing mobile phase with 20% acetonitrile.

Figure 3:
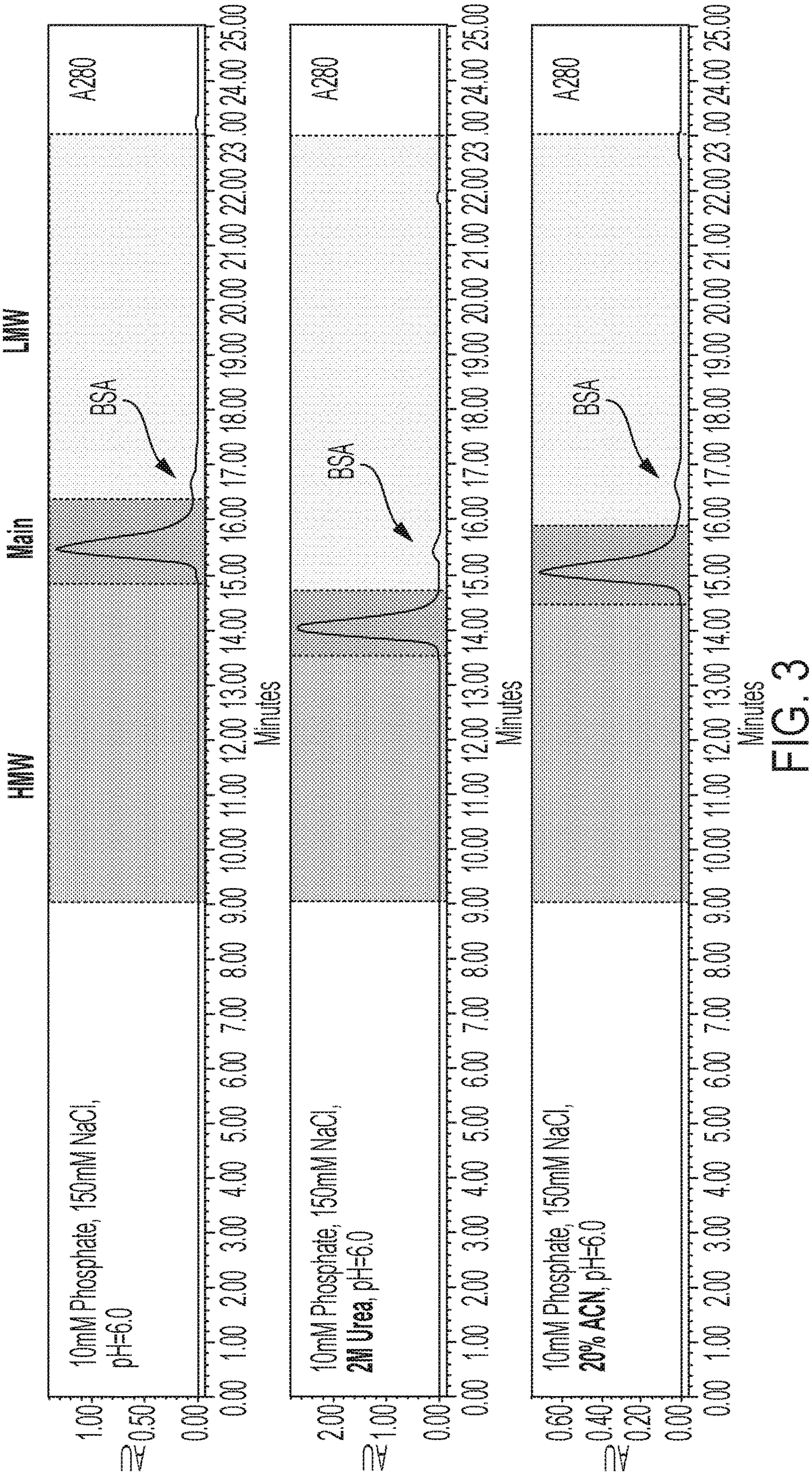
FIG. 3 shows SEC chromatograms of mAb1 drug substance with spiked-in BSA in three different mobile phases, according to an exemplary embodiment.
Figure 4:
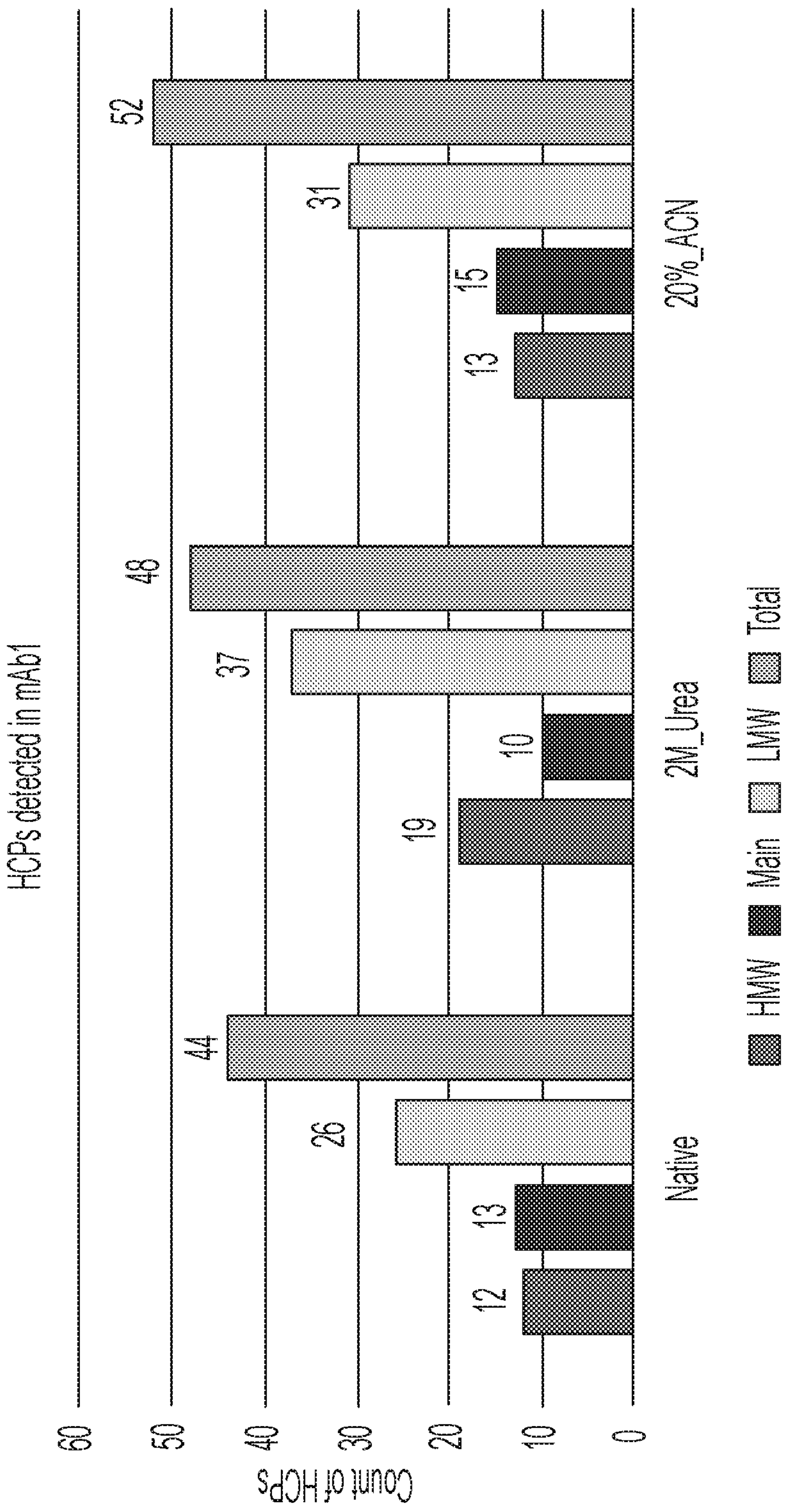
FIG. 4 shows the number of HCPs detected in mAb1 drug substance using the method of the present invention with three different mobile phases, according to an exemplary embodiment.

SEC analysis of mAb1 was performed using the three described mobile phases with BSA as a standard, as shown in FIG. 3. Based on these results, three distinct fractions were identified and collected for further analysis: a high molecular weight (HMW) fraction, a main fraction including the mAb peak, and low molecular weight (LMW) fraction. The collected SEC fractions were further subjected to LC-MS analysis and the number of HCPs identified in each fraction and using each mobile phase were compared, as shown in FIG. 4. In all cases, most HCPs were enriched in the LMW fraction. Based on the total number of HCPs detected, denaturing conditions with 20% acetonitrile were selected for further optimization.

Figure 5:
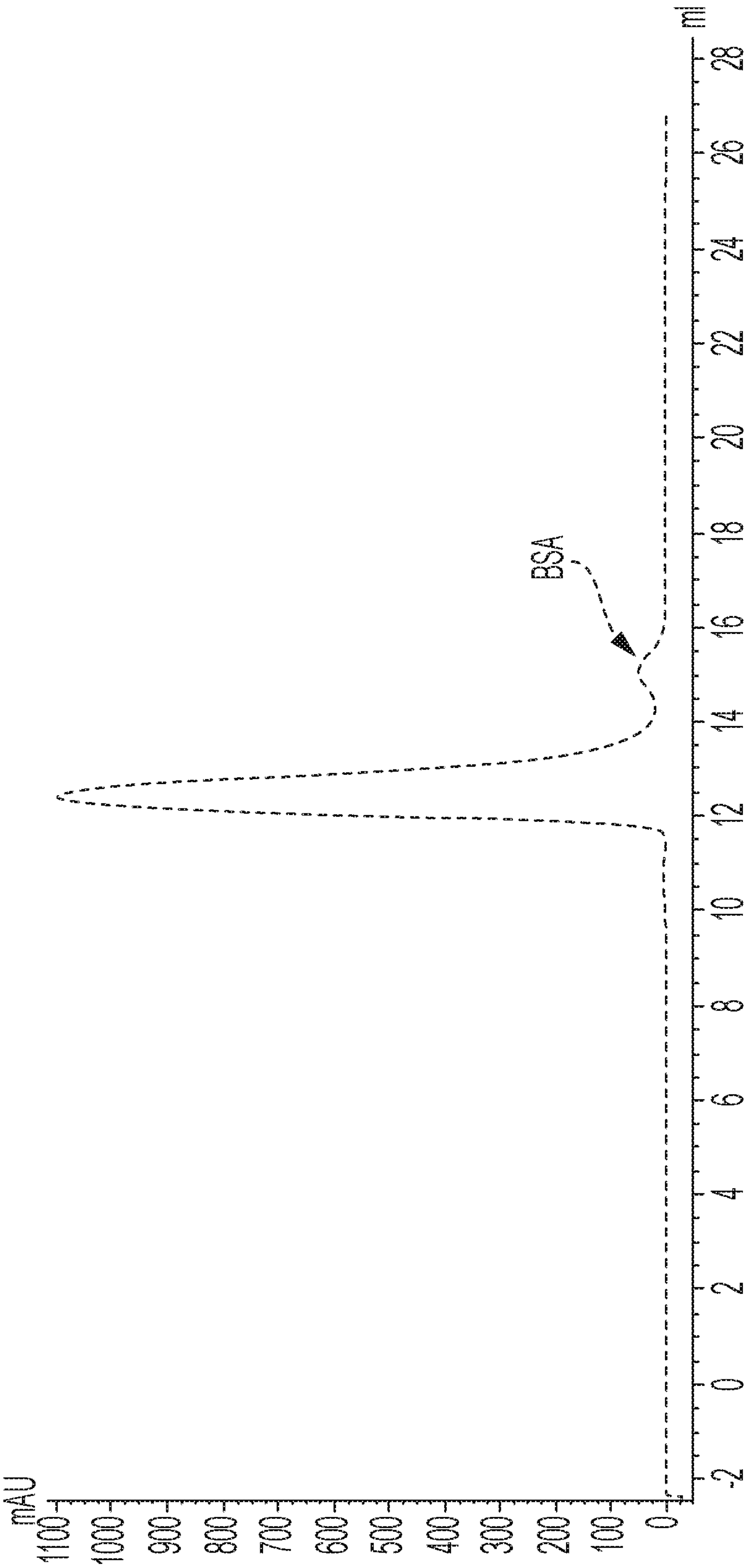
FIG. 5 shows an SEC chromatogram of mAb1 drug substance with spiked-in BSA at a semi-preparative scale, according to an exemplary embodiment.
Figure 6:
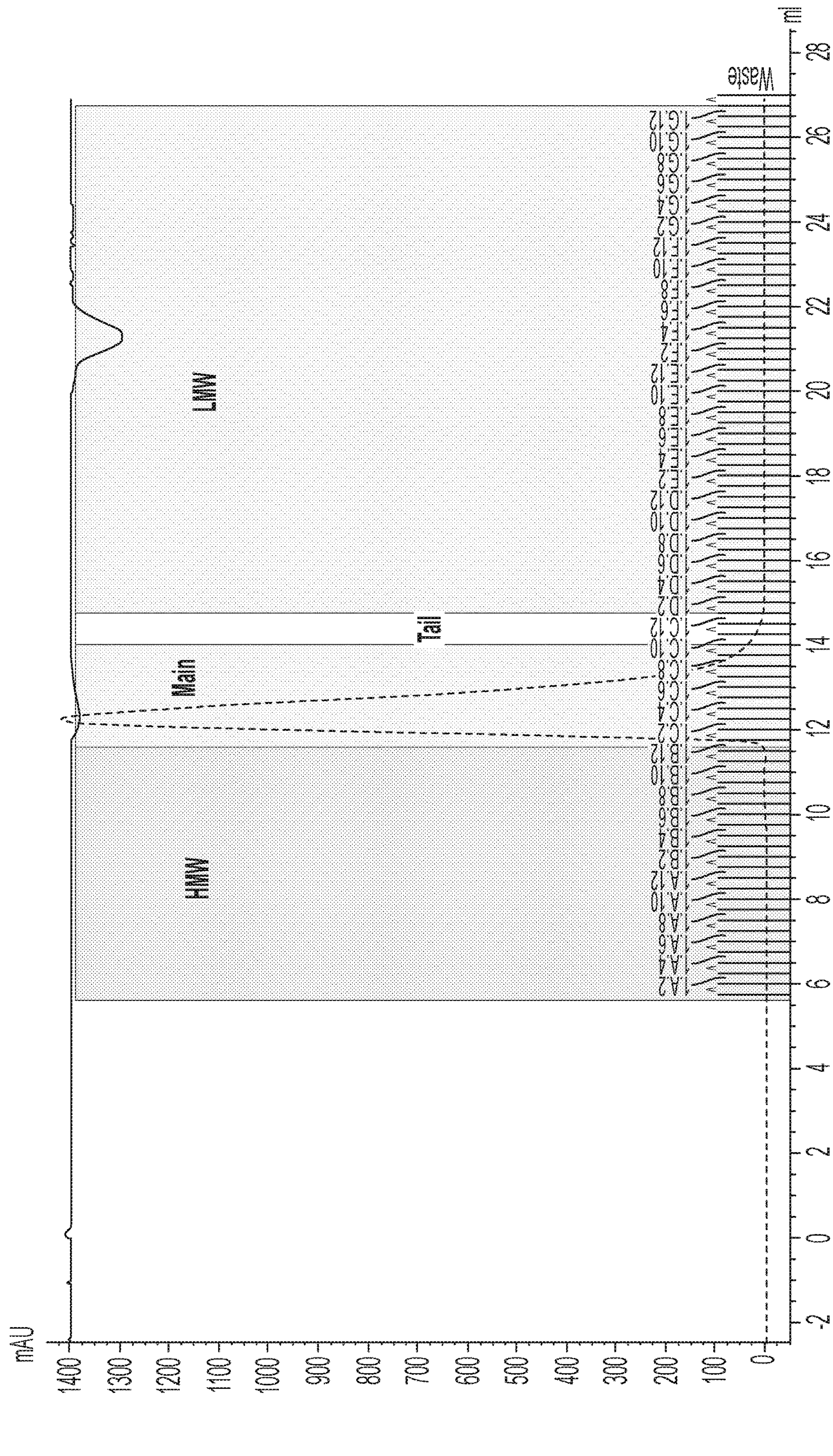
FIG. 6 shows an SEC chromatogram of mAb1 drug substance at a semi-preparative scale, according to an exemplary embodiment.

Example 3. Optimization of the Size Exclusion Chromatography Method for Host Cell Protein Identification Based on the results of the analytical scale SEC method described above, loading amount of the protein was increased to create a semi-preparative scale SEC method. An exemplary chromatography system suitable for this method is an AKTA Pure 25 chromatography system with a Cytiva Superdex 200 Increase 10/300 GL (8.6 μm) column. Feasibility of the semi-preparative scale method was tested using spiked-in BSA as a standard, as shown in FIG. 5. Based on method optimization, final semi-preparative SEC parameters included loading 5 mg of protein (for example, mAb1), using a denaturing mobile phase comprising 20% acetonitrile, a 0.5 mL/min flow rate, and 0.25 mL/well collection. Fractions of interest from the SEC chromatogram were defined as an HMW fraction, from 0.3 column volumes (CV) to the 5 milli absorbance units (mAU) front, a main fraction from the 5 mAU front to the 40 mAU end, a tail fraction from the 40 mAU front to the 10 mAU end, and an LMW fraction from the 10 mAU front to 1.1. CV, as shown in FIG. 6.

Figure 7A:
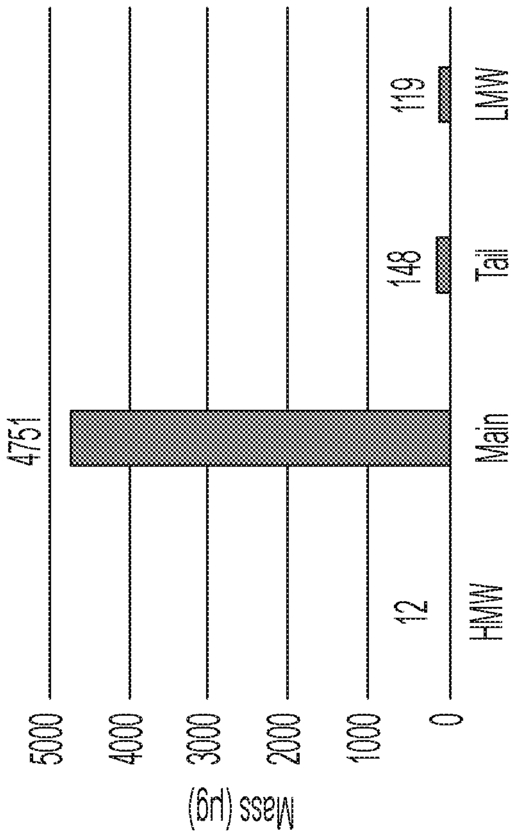
FIG. 7A shows the amount of protein detected in each SEC fraction from mAb1 drug substance, according to an exemplary embodiment.
Figure 7B:
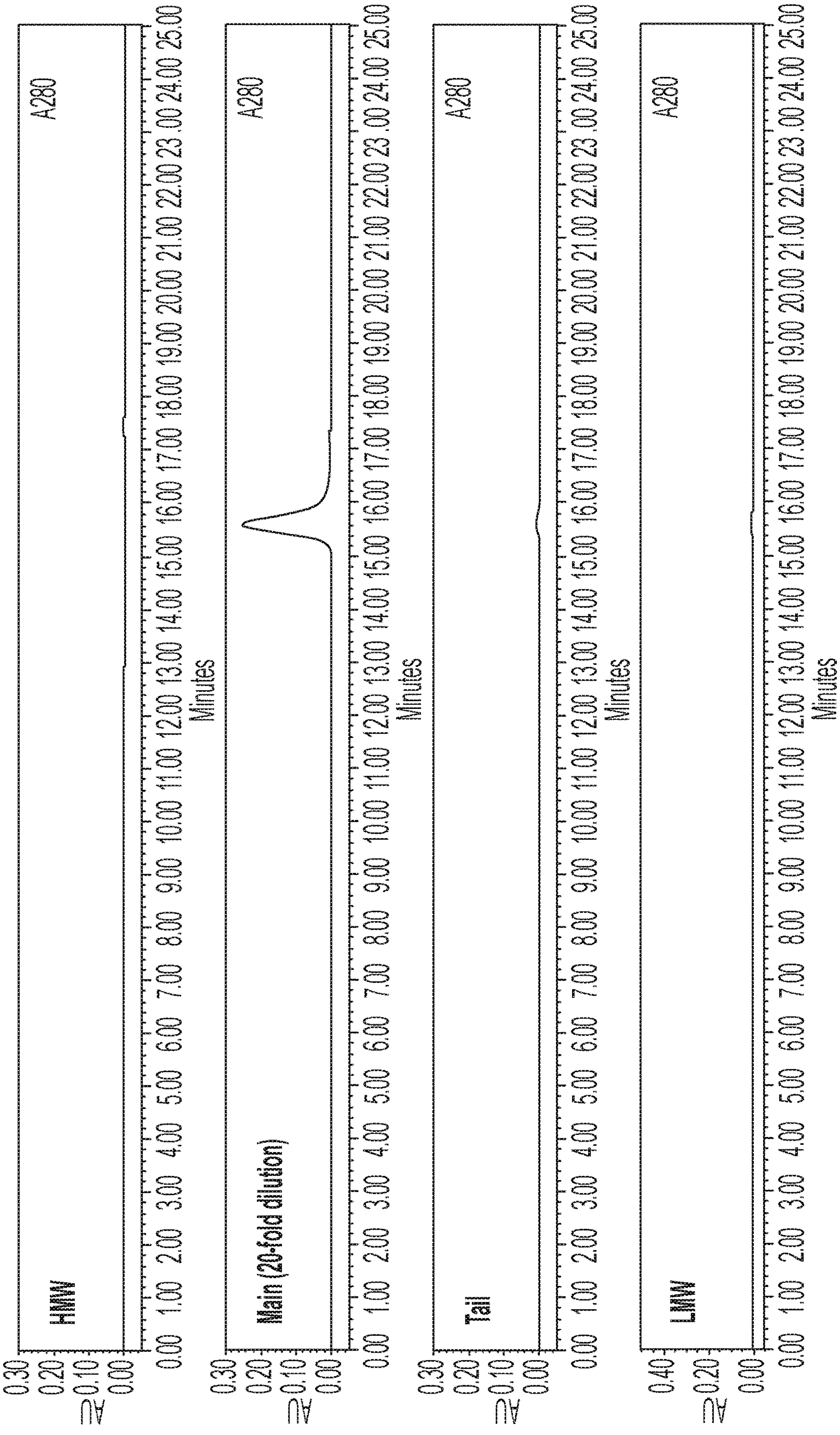
FIG. 7B shows UV chromatograms of each SEC fraction from mAb1 drug substance, according to an exemplary embodiment.

The amount of protein in each fraction was estimated using re-injection, as shown in FIG. 7A and FIG. 7B. Each collected fraction was injected to SEC again to check the purity of the collected fraction. About 95% of the mAb was enriched in the main fraction. About 5% of the sample was lost during buffer exchange. HCPs were expected to be enriched in the HMW, tail, and LMW fractions.

Figure 8:
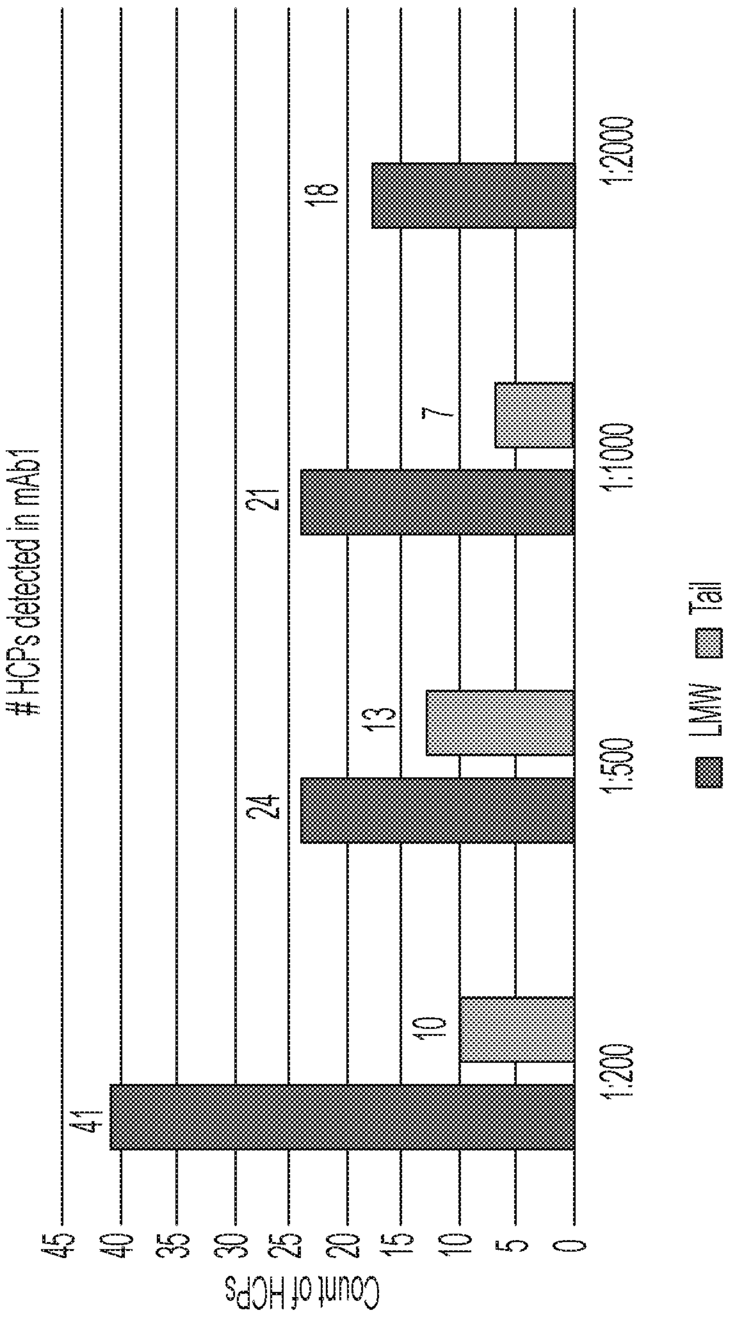
FIG. 8 shows the number of HCPs detected using various enzyme to substrate ratios in a limited digestion step, according to an exemplary embodiment.
Figure 9:
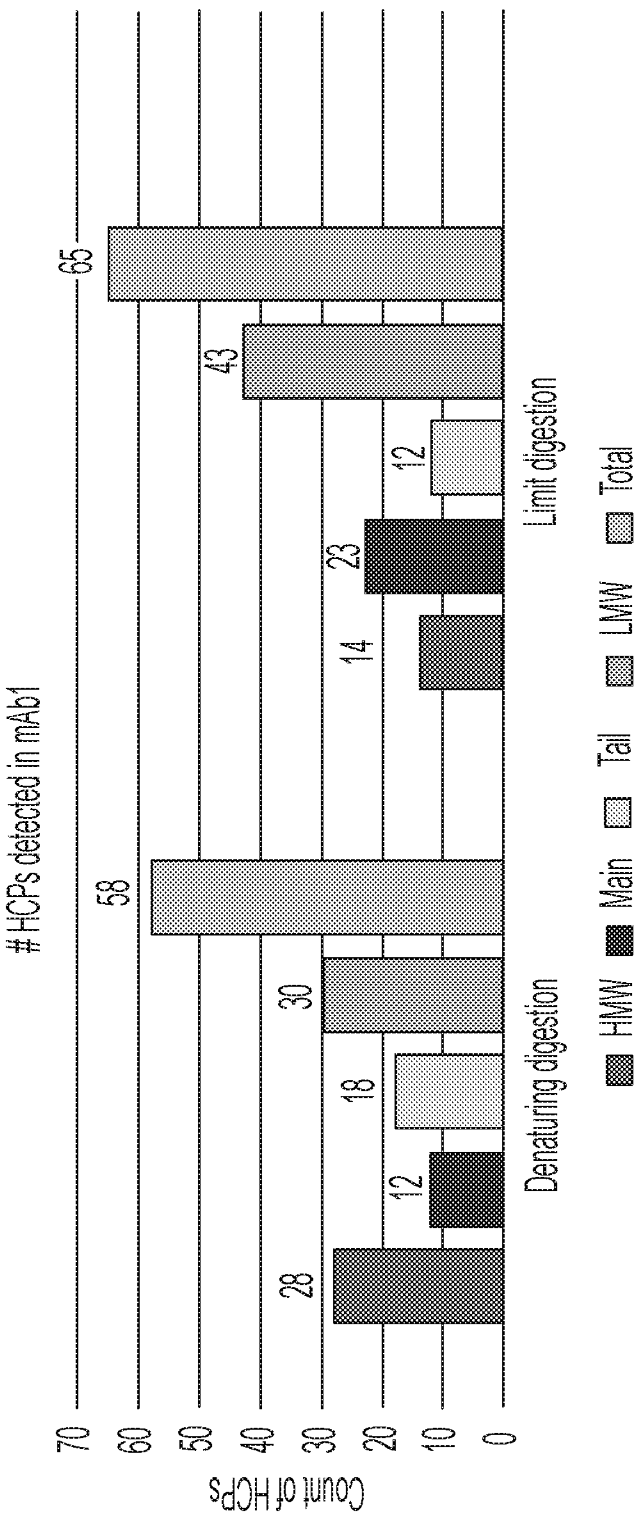
FIG. 9 shows the number of HCPs detected in each SEC fraction using either denaturing digestion or limited digestion, according to an exemplary embodiment.

The method was further optimized using limited digestion, which has previously been shown to be useful in HCP analysis. To produce limited digestion, the enzyme to protein (substrate) ratio must be optimized. A test of limited digestion using a range of enzyme to protein ratios is shown in FIG. 8. Optimized enzyme to protein ratios selected were 1:200 for the HMW fraction, 1:2000 for the main fraction, 1:500 for the tail fraction, and 1:200 for the LMW fraction. The optimized limited digestion step was compared to a denaturing digestion step in combination with the SEC method of the present invention and was found to show an improved ability to identify HCPs, as shown in FIG. 9.

Figure 10:
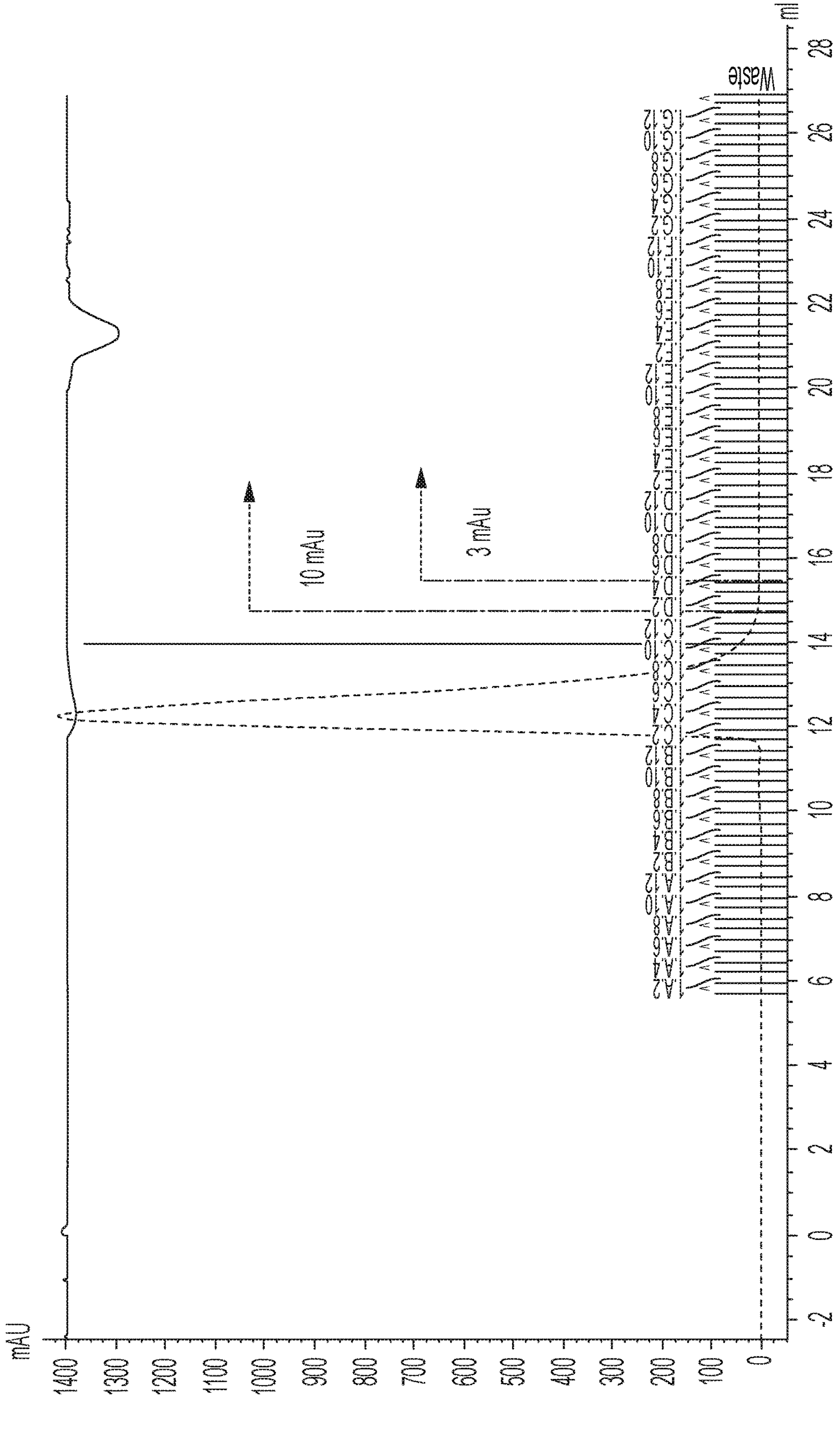
FIG. 10 shows 10 mAU and 3 mAU UV cutoffs in an SEC chromatogram, according to an exemplary embodiment.
Figure 11:
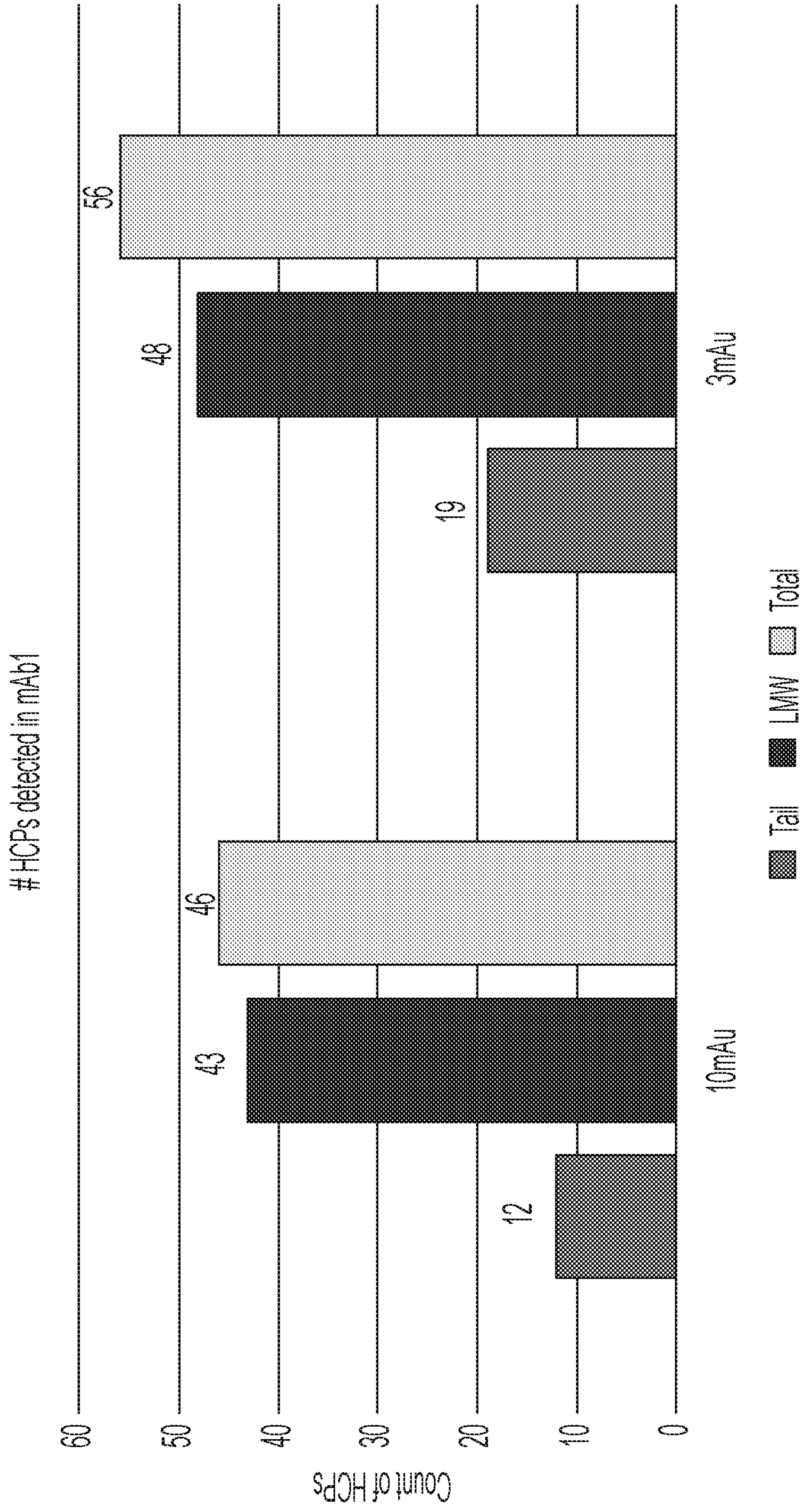
FIG. 11 shows the number of HCPs detected in mAb1 drug substance using either 10 mAU or 3 mAU UV cutoffs with the method of the present invention, according to an exemplary embodiment.

An additional optimization of the method of the present invention involved testing delimiting the tail and LMW fractions at different UV mAU values, which affects the depletion of antibody drug product from the tested fractions and sensitivity for HCP detection. A 10 mAU cutoff and a 3 mAU cutoff were evaluated, as shown in FIG. 10. The number of HCPs identified using each cutoff was compared, as shown in FIG. 11. The 3 mAU cutoff was found to be more effective and was selected for use in the optimized method of the present invention.

Figure 12:
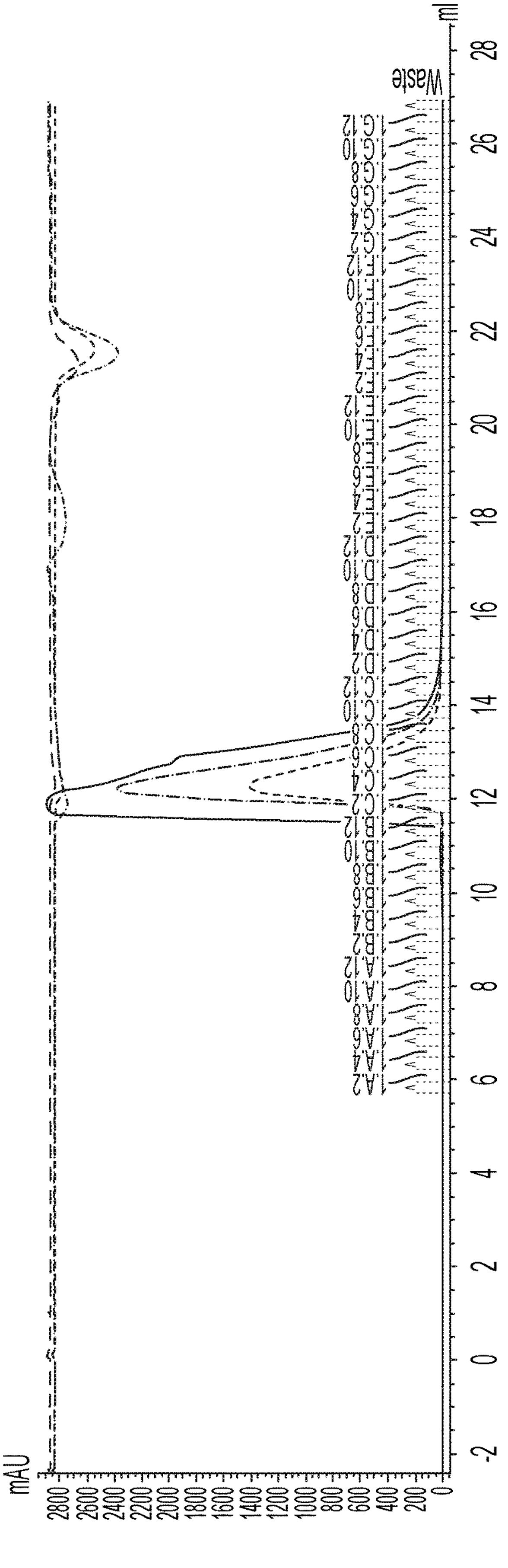
FIG. 12 shows SEC chromatograms for mAb1 drug substance using 5 mg, 10 mg or 20 mg loading, according to an exemplary embodiment.
Figure 13:
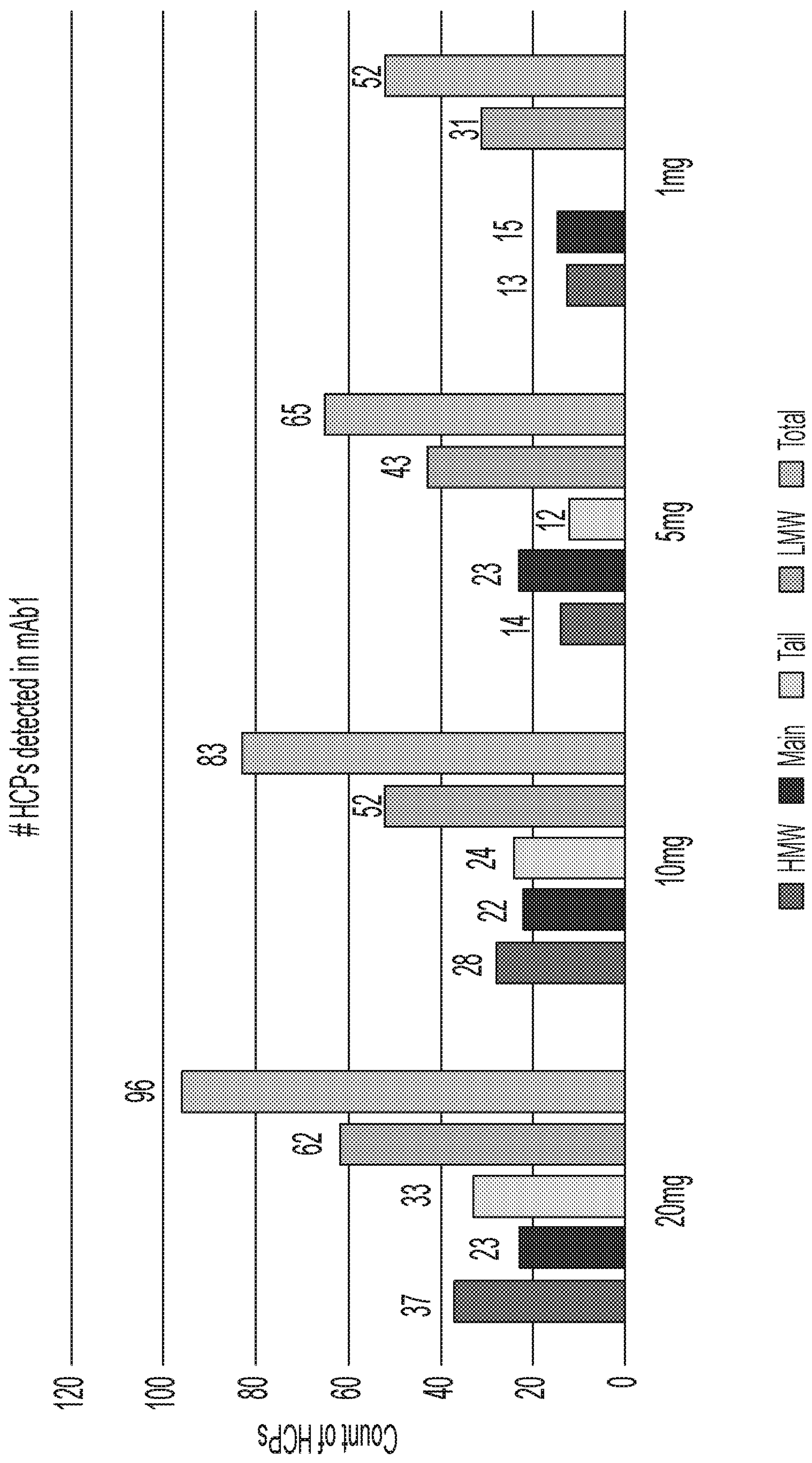
FIG. 13 shows the number of HCPs detected in mAb1 drug substance using the method of the present invention with various protein loading amounts, according to an exemplary embodiment.

The loading amount for the semi-preparative scale method was further optimized by testing loading increasing amounts of protein. An SEC chromatogram of the method using 5 mg protein (small blue peak), 10 mg protein (medium green peak) or 20 mg protein (large black peak) is shown in FIG. 12. The number of HCPs identified using loading amounts of 1, 5, 10 or 20 mg was compared, as shown in FIG. 13. There was found to be a positive correlation between loading amount and number of HCPs detected, but loading the highest amount, 20 mg, led to a distorted peak shape due to over-loading. Therefore, 10 mg was selected as the optimized loading amount. Higher overall loading amounts could be achieved by loading 10 mg per run.

Figure 14:
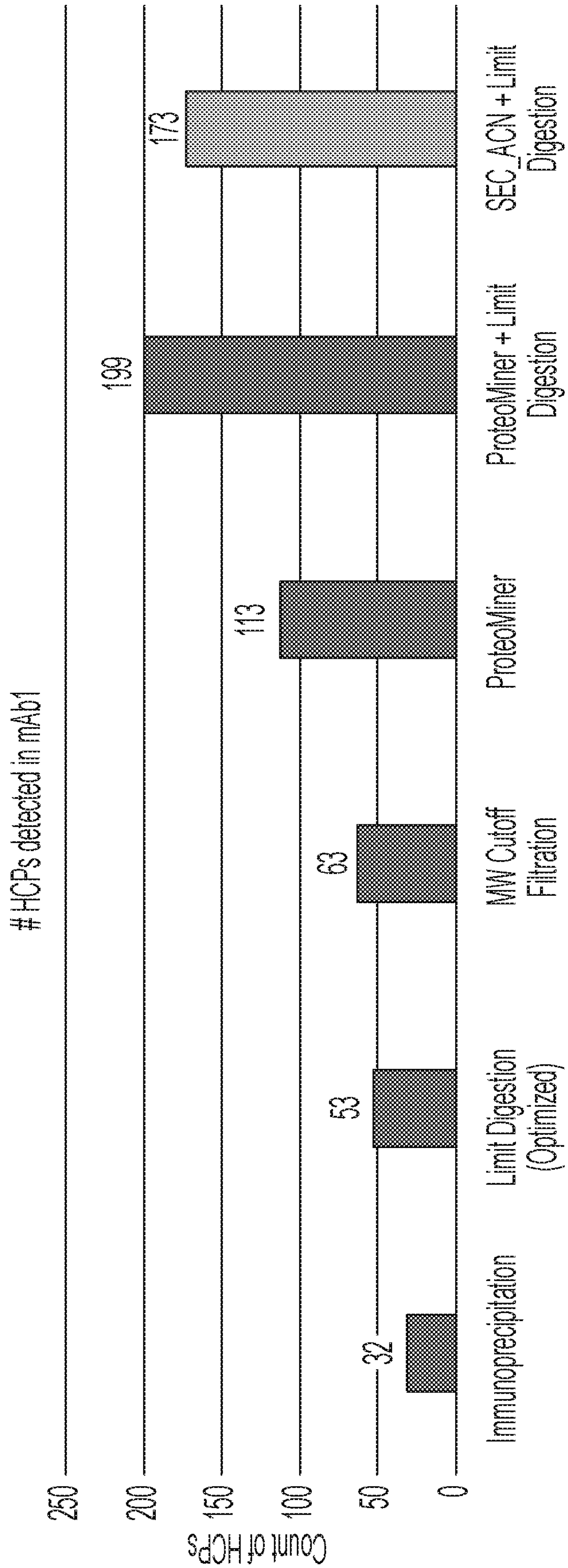
FIG. 14 shows the number of HCPs detected in mAb1 drug substance using the method of the present invention compared to previously described methods, according to an exemplary embodiment.

The ability of the method of the present invention to detect HCPs was compared to previously described methods. mAb1 sample was subjected to HCP analysis using immunoprecipitation, limited digestion, molecular weight cutoff filtration, ProteoMiner beads, ProteoMiner with limited digestion, or the SEC-limited digestion method of the present invention, as shown in FIG. 14. The method of the present invention was found to be more effective than almost any previously described method.

Figure 15A:
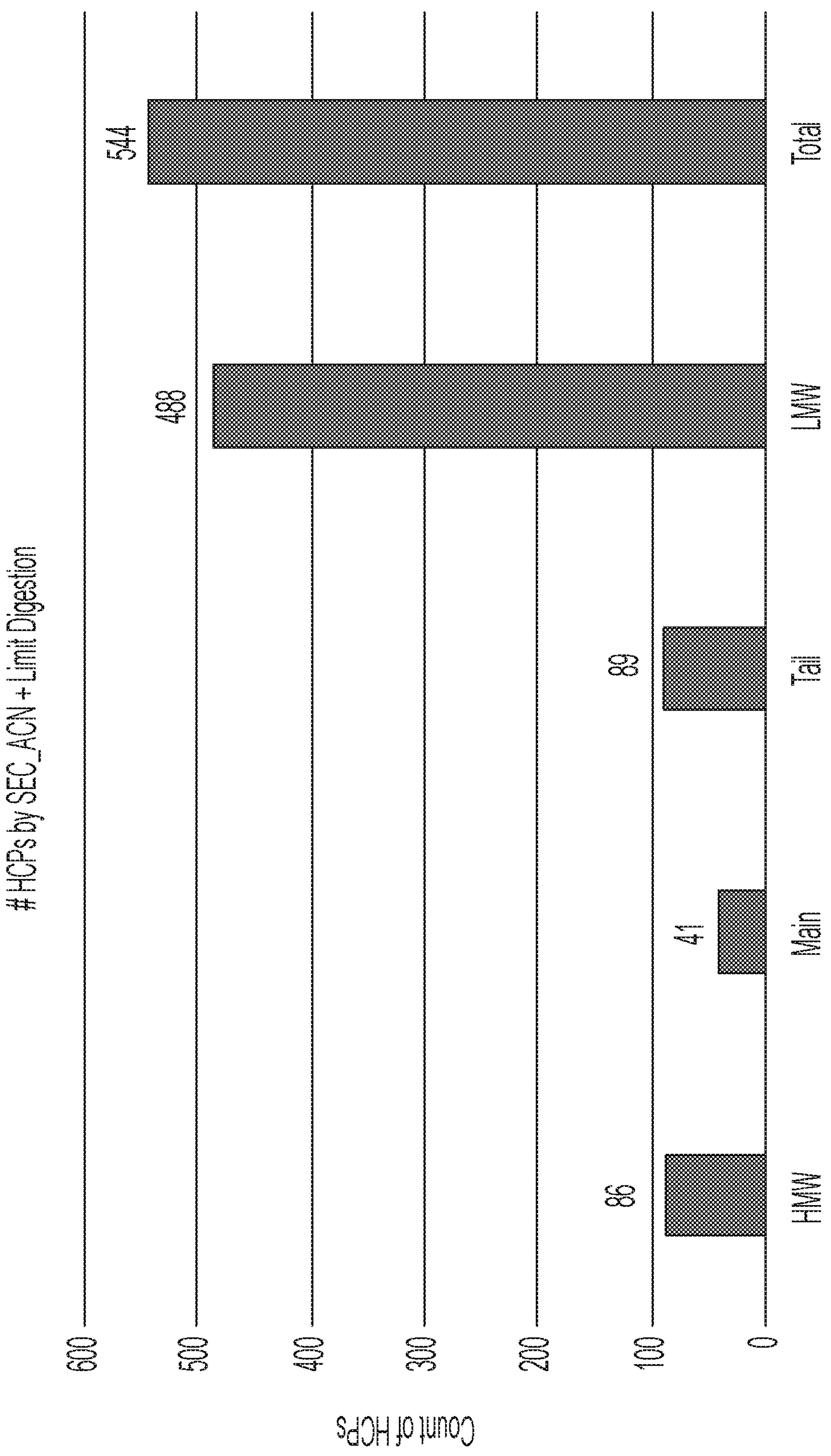
FIG. 15A shows the number of HCPs detected in a NISTmAb 8671 sample using the method of the present invention, according to an exemplary embodiment.
Figure 15B:
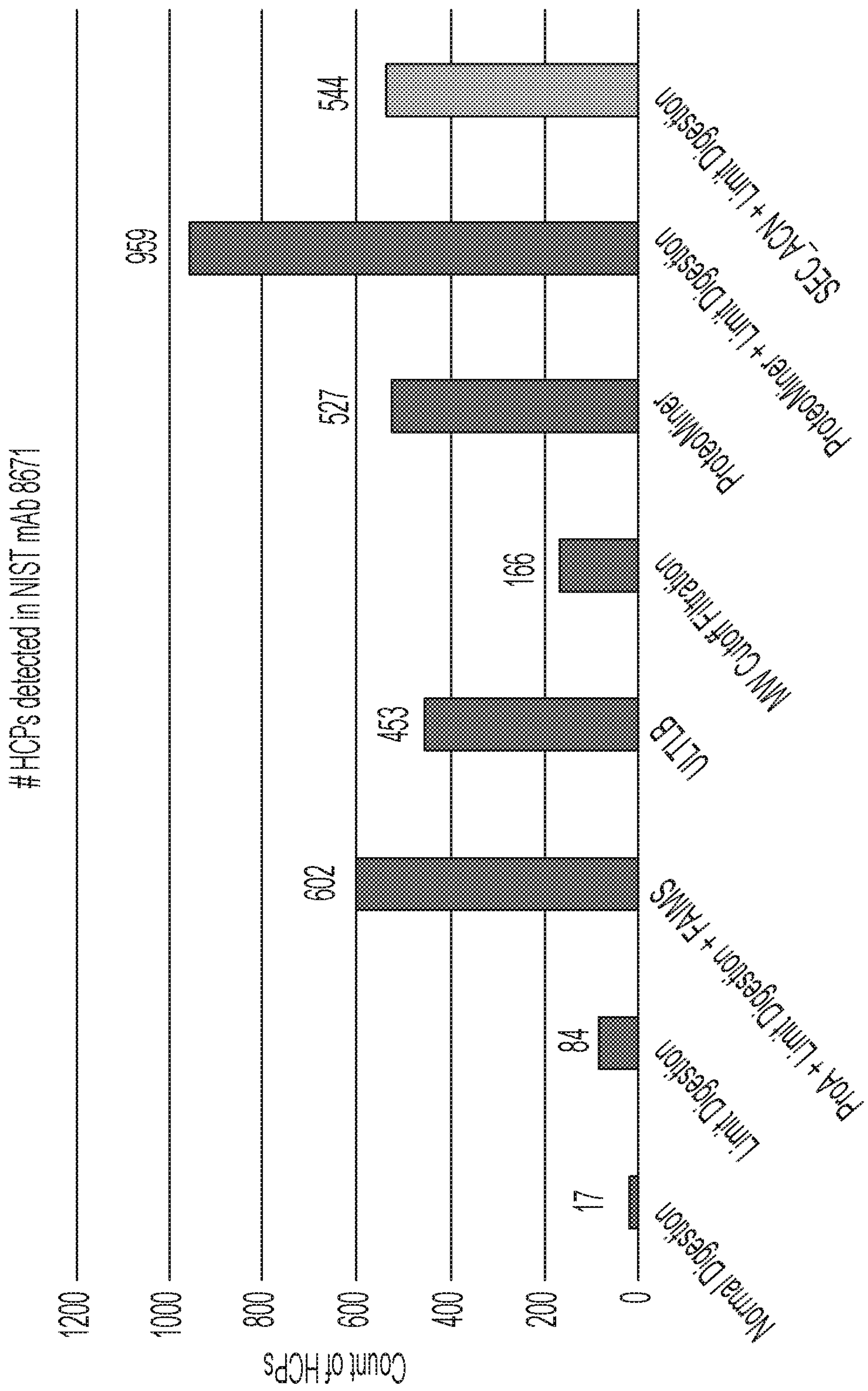
FIG. 15B shows the number of HCPs detected in a NISTmAb 8671 sample using the method of the present invention compared to published results from previously described methods, according to an exemplary embodiment.

Further comparison was made using the protein standard NISTmAb 8671. A total of 544 HCPs were identified in a NISTmAb sample using the method of the present invention, as shown in FIG. 15A. This result was compared to historical data of NISTmAb analyses using previously described methods and was found to be comparably effective, as shown in FIG. 15B.

Example 4. Size Exclusion Chromatography Method for Host Cell Protein Binding Analysis An advantage of the method of the present invention is the ability to analyze HCPs on the basis of size, due to the separation mechanism of SEC. In addition to gaining information about the size of a protein itself, this provides information about the binding properties of a protein, since a protein bound to another protein will show an apparent shift in size. This distinction can be assessed using a comparison between proteins separated with a native mobile phase, which will preserve protein-protein interactions, and the same proteins separated with a mildly denaturing mobile phase such as 20% acetonitrile, which will abolish weak protein-protein interactions without disrupting strong protein-protein interactions.

The sensitivity of the method of the present invention conducted with two different mobile phases was assessed using a UPS2 standard. UPS2 is a commercially available proteomics standard comprising 48 human proteins at a wide dynamic range of concentrations spanning many orders of magnitude. mAb1 was fractionated using the optimized conditions described above, with one of two different mobile phases: either the native, non-denaturing mobile phase, or the denaturing mobile phase comprising 20% acetonitrile. The number of UPS2 proteins detected in each condition at each level of concentration is shown in Table 1. Ppm is given in molar ratio.

TABLE 1

UPS2 detected using native or 20% acetonitrile mobile phases

| Mobile Phase | # UPS2 Detected | 1.875 × $10^1$ ppm | 1.875 × $10^0$ ppm | 1.875 × $10^{-1}$ ppm | 1.875 × $10^{-2}$ ppm | 1.875 × $10^{-3}$ ppm | 1.875 × $10^{-4}$ ppm |
|---|---|---|---|---|---|---|---|
| Native | 15/48 | 7/8 | 4/8 | 2/8 | 1/8 | 1/8 | 0/8 |
| 20% Acetonitrile | 16/48 | 7/8 | 7/8 | 1/8 | 1/8 | 0/8 | 0/8 |

Figure 16A:
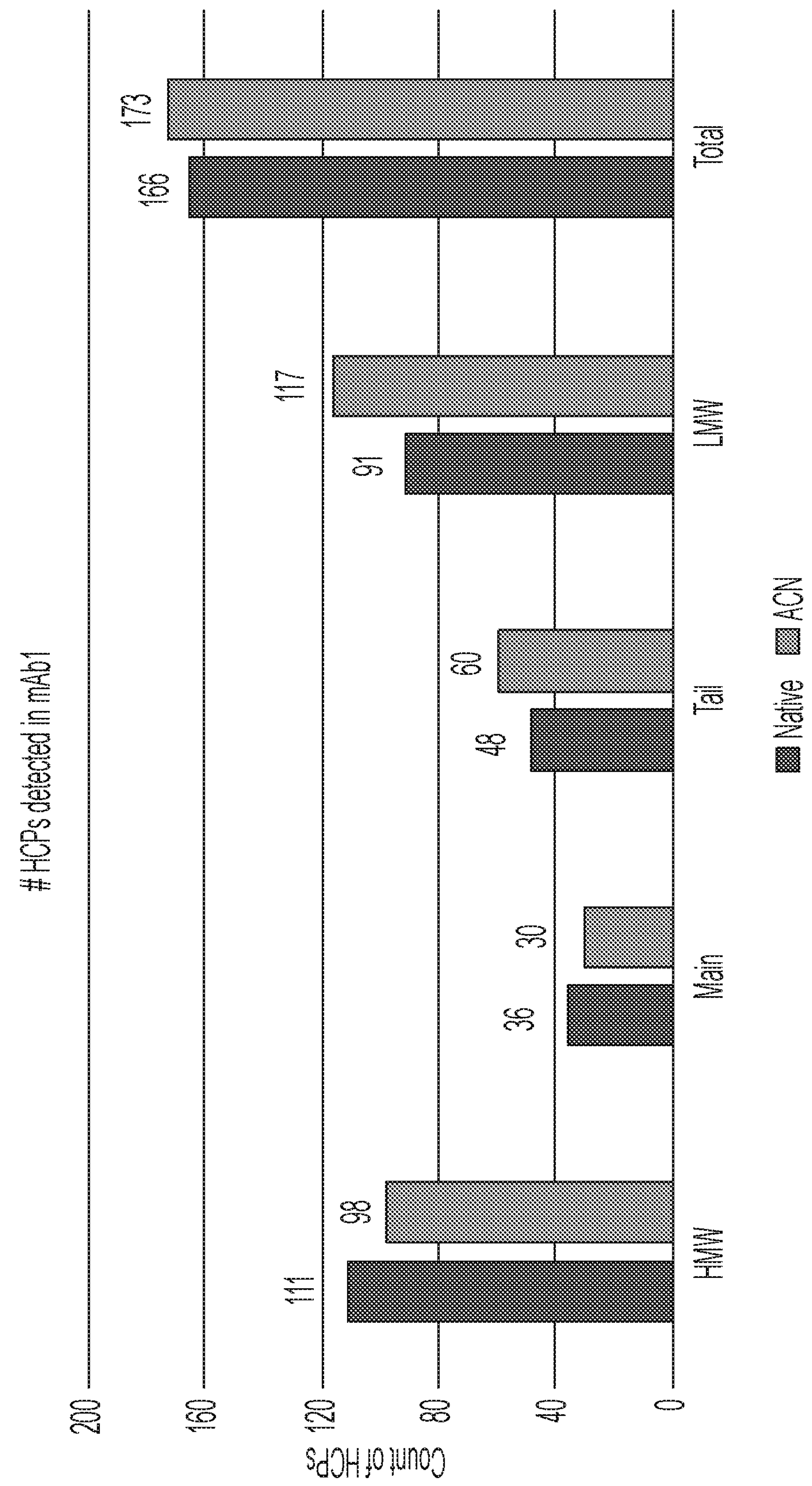
FIG. 16A shows the number of HCPs detected in mAb1 drug substance in each SEC fraction using the method of the present invention with either native or acetonitrile (ACN) mobile phase, according to an exemplary embodiment.
Figure 16B:
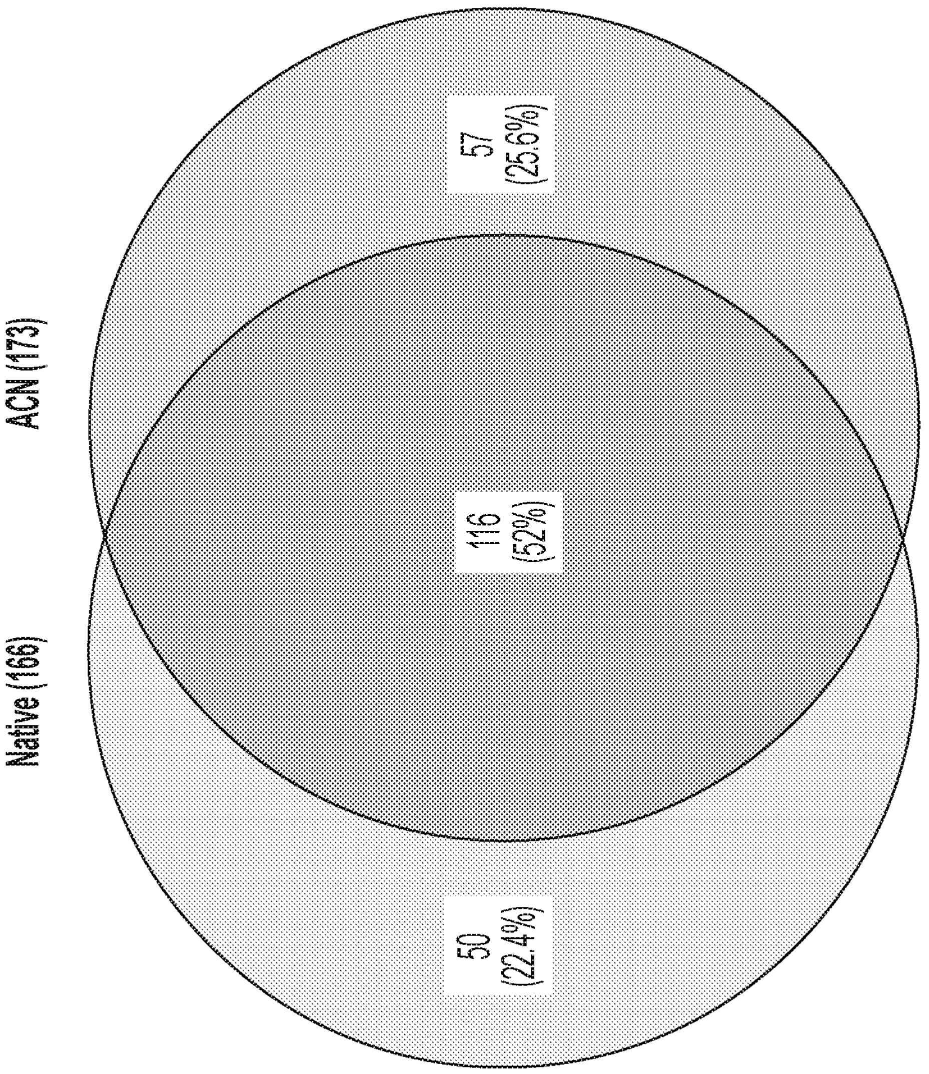
FIG. 16B shows the overlap of HCPs detected in mAb1 drug substance using the method of the present invention with either native or acetonitrile mobile phase, according to an exemplary embodiment.

The number of HCPs from each fraction of a mAb1 sample detected by the method of the present invention using either a native mobile phase or 20% acetonitrile mobile phase was compared, as shown in FIG. 16A. More HCPs were detected in the HMW and main fractions using a native mobile phase, while more HCPs were detected in the tail and LMW fractions using a 20% acetonitrile mobile phase. The overlap of total HCPs detected in each condition is shown in FIG. 16B.

Figure 17A:
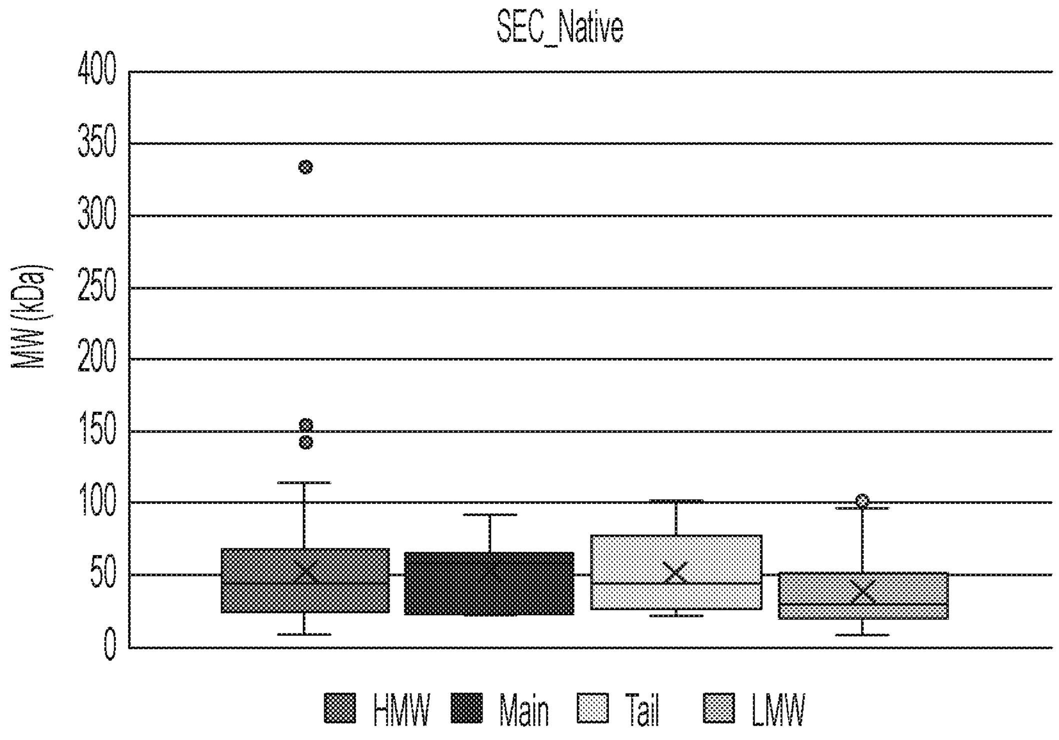
FIG. 17A shows the masses of HCPs detected in mAb1 drug substance in each SEC fraction using the method of the present invention with native mobile phase, according to an exemplary embodiment.
Figure 17B:
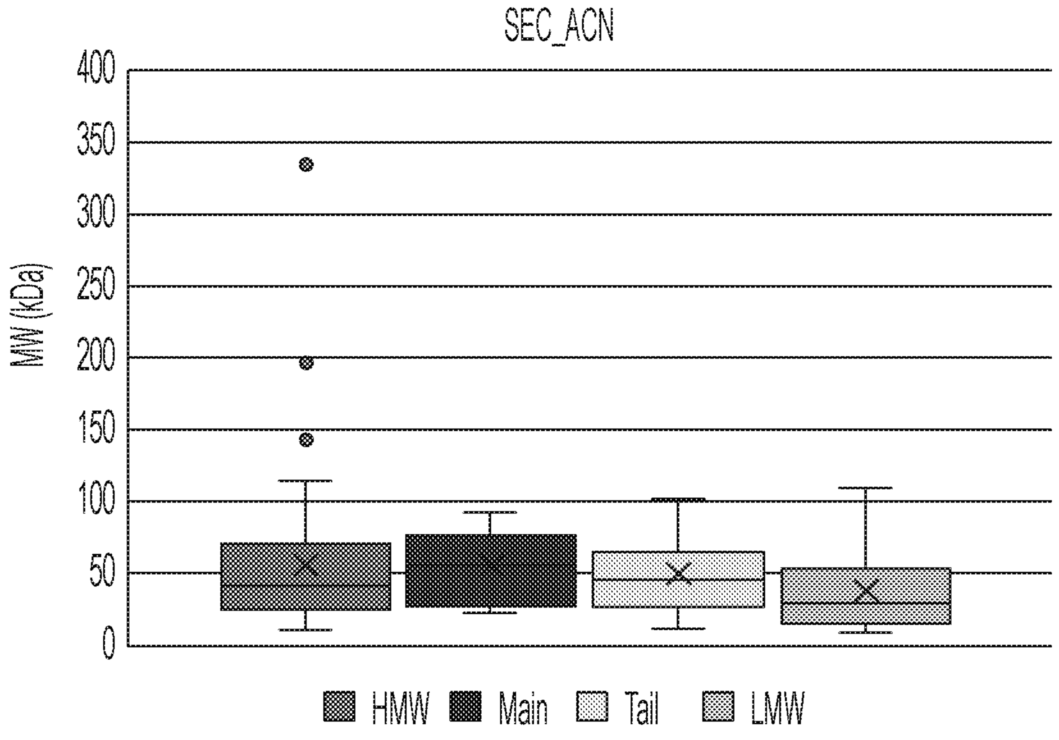
FIG. 17B shows the masses of HCPs detected in mAb1 drug substance in each SEC fraction using the method of the present invention with acetonitrile mobile phase, according to an exemplary embodiment.

HCPs identified in each condition were further characterized by molecular weight, as shown in FIG. 17A and FIG. 17B. Overall, there was a decreasing trend of molecular weight going from the HMW fraction through the LMW fraction, consistent with the separation mechanism of SEC. However, the HMW fraction also included proteins with lower molecular weights than would be expected, for example below 100 kDa, suggesting that they may have a shorter retention time in the SEC column due to binding to mAb1.

In order to generate a binding profile of all detected HCPs, the apparent size of each identified HCP by SEC in native (non-denaturing) or denaturing conditions was compared, as shown in Table 2.

TABLE 2

Host cell protein separation by size exclusion chromatography in native or denaturing conditions

| HCP | Native HMW | Native Main | Native Tail | Native LMW | Denaturing (20% acetonitrile) HMW | Denaturing (20% acetonitrile) Main | Denaturing (20% acetonitrile) Tail | Denaturing (20% acetonitrile) LMW |
|---|---|---|---|---|---|---|---|---|
| >tr\|G3HCV4\|G3HCV4_ CRIGR Alpha-mannosidase | 100.0% | 0.0% | 0.0% | 0.0% | 100.0% | 0.0% | 0.0% | 0.0% |
| >tr\|G3GZB2\|G3GZB2_ CRIGR Acid ceramidase | 100.0% | 0.0% | 0.0% | 0.0% | 100.0% | 0.0% | 0.0% | 0.0% |
| >tr\|G3GYY6\|G3GYY6_ CRIGR Catalase | 100.0% | 0.0% | 0.0% | 0.0% | 100.0% | 0.0% | 0.0% | 0.0% |
| >tr\|G3HIM1\|G3HIM1_ CRIGR Basement membrane-specific heparan sulfate proteoglycan core protein | 100.0% | 0.0% | 0.0% | 0.0% | 100.0% | 0.0% | 0.0% | 0.0% |
| >tr\|G3H928\|G3H928_ CRIGR Adenylate kinase 2, mitochondrial | 100.0% | 0.0% | 0.0% | 0.0% | 100.0% | 0.0% | 0.0% | 0.0% |
| >tr\|G3HF46\|G3HF46_ CRIGR Polypyrimidine tract-binding protein 1 | 100.0% | 0.0% | 0.0% | 0.0% | 100.0% | 0.0% | 0.0% | 0.0% |
| >tr\|G3GX17\|G3GX17_ CRIGR Polypeptide N-acetylgalactosaminyl-transferase | 100.0% | 0.0% | 0.0% | 0.0% | 100.0% | 0.0% | 0.0% | 0.0% |
| >tr\|G3IKH3\|G3IKH3_ CRIGR Collagen alpha-2(V) chain | 100.0% | 0.0% | 0.0% | 0.0% | 100.0% | 0.0% | 0.0% | 0.0% |
| >tr\|G3H7I6\|G3H7I6_ CRIGR Sulfhydryl oxidase | 100.0% | 0.0% | 0.0% | 0.0% | 100.0% | 0.0% | 0.0% | 0.0% |
| >tr\|G3H2P3\|G3H2P3_ CRIGR Beta-galactosidase (Fragment) | 100.0% | 0.0% | 0.0% | 0.0% | 100.0% | 0.0% | 0.0% | 0.0% |
| >tr\|G3I2T9\|G3I2T9_ CRIGR 3-phosphoinositide-dependent protein kinase 1 | 100.0% | 0.0% | 0.0% | 0.0% | 100.0% | 0.0% | 0.0% | 0.0% |
| >tr\|G3IKH4\|G3IKH4_ CRIGR Collagen alpha-2(V) chain | 100.0% | 0.0% | 0.0% | 0.0% | 100.0% | 0.0% | 0.0% | 0.0% |
| >tr\|G3IA26\|G3IA26_ CRIGR Heparanase | 100.0% | 0.0% | 0.0% | 0.0% | 100.0% | 0.0% | 0.0% | 0.0% |
| >tr\|G3HRF8\|G3HRF8_ CRIGR CD166 antigen | 100.0% | 0.0% | 0.0% | 0.0% | 100.0% | 0.0% | 0.0% | 0.0% |
| >tr\|G3IN86\|G3IN86_ CRIGR DPP7 | 100.0% | 0.0% | 0.0% | 0.0% | 87.5% | 0.0% | 12.5% | 0.0% |
| >tr\|G3I255\|G3I255_CRIGR L-lactate dehydrogenase | 97.1% | 0.0% | 2.9% | 0.0% | 91.7% | 0.0% | 8.3% | 0.0% |
| >Q06830ups\|PRDX1_ HUMAN_UPS Peroxiredoxin | 100.0% | 0.0% | 0.0% | 0.0% | 85.7% | 0.0% | 14.3% | 0.0% |

TABLE 2-continued

<table>
<tr><th colspan="9">Host cell protein separation by size exclusion chromatography in native or denaturing conditions</th></tr>
<tr><th></th><th colspan="4">Native</th><th colspan="4">Denaturing (20% acetonitrile)</th></tr>
<tr><th>HCP</th><th>HMW</th><th>Main</th><th>Tail</th><th>LMW</th><th>HMW</th><th>Main</th><th>Tail</th><th>LMW</th></tr>
<tr><td>1 (Chain 2-199)-Homo sapiens (Human)</td><td></td><td></td><td></td><td></td><td></td><td></td><td></td><td></td></tr>
<tr><td>>tr|G3I5L3|G3I5L3_ CRIGR Annexin</td><td>89.3%</td><td>0.0%</td><td>0.0%</td><td>10.7%</td><td>100.0%</td><td>0.0%</td><td>0.0%</td><td>0.0%</td></tr>
<tr><td>>tr|G3IHT7|G3IHT7_ CRIGR Semaphorin-4B</td><td>90.2%</td><td>2.4%</td><td>7.3%</td><td>0.0%</td><td>82.4%</td><td>0.0%</td><td>17.6%</td><td>0.0%</td></tr>
<tr><td>>tr|G3HCL3|G3HCL3_ CRIGR TNFSF9</td><td>100.0%</td><td>0.0%</td><td>0.0%</td><td>0.0%</td><td>87.5%</td><td>0.0%</td><td>0.0%</td><td>12.5%</td></tr>
<tr><td>>tr| G3HBD3|G3HBD3_ CRIGR Nucleoside diphosphate kinase</td><td>100.0%</td><td>0.0%</td><td>0.0%</td><td>0.0%</td><td>64.3%</td><td>0.0%</td><td>35.7%</td><td>0.0%</td></tr>
<tr><td>>tr|G3GZZ0|G3GZZ0_ CRIGR Aspartate aminotransferase</td><td>100.0%</td><td>0.0%</td><td>0.0%</td><td>0.0%</td><td>63.6%</td><td>0.0%</td><td>36.4%</td><td>0.0%</td></tr>
<tr><td>>tr|G3H8A8|G3H8A8_ CRIGR Mesencephalic astrocyte-derived neurotrophic factor</td><td>100.0%</td><td>0.0%</td><td>0.0%</td><td>0.0%</td><td>42.9%</td><td>57.1%</td><td>0.0%</td><td>0.0%</td></tr>
<tr><td>>tr|G3H5Q0|G3H5Q0_ CRIGR Actin, alpha cardiac muscle 1</td><td>100.0%</td><td>0.0%</td><td>0.0%</td><td>0.0%</td><td>0.0%</td><td>50.0%</td><td>50.0%</td><td>0.0%</td></tr>
<tr><td>>tr|G3GS79|G3GS79_ CRIGR Zinc finger protein DZIP1</td><td>100.0%</td><td>0.0%</td><td>0.0%</td><td>0.0%</td><td>72.7%</td><td>0.0%</td><td>0.0%</td><td>27.3%</td></tr>
<tr><td>>tr|G3I7X7|G3I7X7_ CRIGR Carboxylic ester hydrolase</td><td>97.0%</td><td>3.0%</td><td>0.0%</td><td>0.0%</td><td>22.8%</td><td>0.0%</td><td>63.2%</td><td>14.0%</td></tr>
<tr><td>>tr|G3GS89|G3GS89_ CRIGR Uncharacterized protein</td><td>100.0%</td><td>0.0%</td><td>0.0%</td><td>0.0%</td><td>8.3%</td><td>33.3%</td><td>25.0%</td><td>33.3%</td></tr>
<tr><td>>tr|G3GRE1|G3GRE1_ CRIGR Bifunctional aminoacyl-tRNA synthetase (Fragment)</td><td>100.0%</td><td>0.0%</td><td>0.0%</td><td>0.0%</td><td>34.4%</td><td>0.0%</td><td>25.0%</td><td>40.6%</td></tr>
<tr><td>>tr|G3I4W7|G3I4W7_ CRIGR Cathepsin D</td><td>100.0%</td><td>0.0%</td><td>0.0%</td><td>0.0%</td><td>25.0%</td><td>0.0%</td><td>25.0%</td><td>50.0%</td></tr>
<tr><td>>tr|G3HS71|G3HS71_ CRIGR Vasorin</td><td>100.0%</td><td>0.0%</td><td>0.0%</td><td>0.0%</td><td>25.0%</td><td>0.0%</td><td>25.0%</td><td>50.0%</td></tr>
<tr><td>>tr|G3HGW6|G3HGW6_ CRIGR Laminin subunit alpha-5</td><td>100.0%</td><td>0.0%</td><td>0.0%</td><td>0.0%</td><td>27.6%</td><td>0.0%</td><td>20.7%</td><td>51.7%</td></tr>
<tr><td>>tr|G3GYP9|G3GYP9_ CRIGR Peroxiredoxin</td><td>82.5%</td><td>7.8%</td><td>7.8%</td><td>1.8%</td><td>66.8%</td><td>4.0%</td><td>19.9%</td><td>9.3%</td></tr>
<tr><td>>tr|G3IBH0|G3IBH0_ CRIGR Metalloproteinase inhibitor 1</td><td>78.8%</td><td>0.0%</td><td>15.2%</td><td>6.1%</td><td>37.9%</td><td>4.2%</td><td>24.2%</td><td>33.7%</td></tr>
<tr><td>>tr|G3I5Z5|G3I5Z5_ CRIGR Prostaglandin reductase 1</td><td>76.8%</td><td>0.0%</td><td>23.2%</td><td>0.0%</td><td>40.0%</td><td>0.0%</td><td>52.5%</td><td>7.5%</td></tr>
<tr><td>>tr|G3GR64|G3GR64_ CRIGR Inter-alpha-trypsin inhibitor heavy chain H5</td><td>76.1%</td><td>0.0%</td><td>23.9%</td><td>0.0%</td><td>30.3%</td><td>0.0%</td><td>39.4%</td><td>30.3%</td></tr>
<tr><td>>tr|G3IIK9|G3IIK9_ CRIGR Cornifin-A</td><td>100.0%</td><td>0.0%</td><td>0.0%</td><td>0.0%</td><td>13.3%</td><td>0.0%</td><td>6.7%</td><td>80.0%</td></tr>
<tr><td>>tr|G3IKQ6|G3IKQ6_ CRIGR CSTB</td><td>100.0%</td><td>0.0%</td><td>0.0%</td><td>0.0%</td><td>5.6%</td><td>0.0%</td><td>0.0%</td><td>94.4%</td></tr>
<tr><td>>tr|G3H0S7|G3H0S7_ CRIGR Beta-2-microglobulin</td><td>100.0%</td><td>0.0%</td><td>0.0%</td><td>0.0%</td><td>0.0%</td><td>0.0%</td><td>0.0%</td><td>100.0%</td></tr>
<tr><td>>tr|G3I3G8|G3I3G8_ CRIGR Transaldolase</td><td>78.6%</td><td>0.0%</td><td>0.0%</td><td>21.4%</td><td>0.0%</td><td>0.0%</td><td>0.0%</td><td>100.0%</td></tr>
<tr><td>>tr|G3HUU6|G3HUU6_ CRIGR Protein S100</td><td>66.7%</td><td>0.0%</td><td>0.0%</td><td>33.3%</td><td>0.0%</td><td>0.0%</td><td>0.0%</td><td>100.0%</td></tr>
<tr><td>>tr|G3I4E8|G3I4E8_ CRIGR Fatty acid-binding protein, adipocyte</td><td>55.6%</td><td>22.2%</td><td>0.0%</td><td>22.2%</td><td>5.3%</td><td>0.0%</td><td>0.0%</td><td>94.7%</td></tr>
<tr><td>>tr|G3IDN7|G3IDN7_ CRIGR Protein FAM3C</td><td>35.6%</td><td>0.0%</td><td>0.0%</td><td>64.4%</td><td>4.2%</td><td>0.0%</td><td>0.0%</td><td>95.8%</td></tr>
<tr><td>>tr| G3HH30| G3HH30_ CRIGR Aldose reductase</td><td>64.4%</td><td>0.0%</td><td>0.0%</td><td>35.6%</td><td>15.6%</td><td>0.0%</td><td>0.0%</td><td>84.4%</td></tr>
<tr><td>>tr|G3IEU2|G3IEU2_ CRIGR Protein DJ-1</td><td>48.1%</td><td>0.0%</td><td>0.0%</td><td>51.9%</td><td>22.2%</td><td>0.0%</td><td>0.0%</td><td>77.8%</td></tr>
</table>

TABLE 2-continued

<table>
<tr><th colspan="9">Host cell protein separation by size exclusion chromatography in native or denaturing conditions</th></tr>
<tr><th></th><th colspan="4">Native</th><th colspan="4">Denaturing (20% acetonitrile)</th></tr>
<tr><th>HCP</th><th>HMW</th><th>Main</th><th>Tail</th><th>LMW</th><th>HMW</th><th>Main</th><th>Tail</th><th>LMW</th></tr>
<tr><td>>tr|G3I3Y6|G3I3Y6_ CRIGR Glutathione S-transferase P</td><td>47.1%</td><td>0.0%</td><td>2.0%</td><td>51.0%</td><td>8.3%</td><td>0.0%</td><td>1.7%</td><td>90.0%</td></tr>
<tr><td>>tr|G3IDN7|G3IDN7_ CRIGR Protein FAM3C</td><td>35.6%</td><td>0.0%</td><td>0.0%</td><td>64.4%</td><td>4.2%</td><td>0.0%</td><td>0.0%</td><td>95.8%</td></tr>
<tr><td>>tr|G3HAI3|G3HAI3_ CRIGR Follistatin-related protein 1</td><td>64.3%</td><td>35.7%</td><td>0.0%</td><td>0.0%</td><td>0.0%</td><td>57.9%</td><td>0.0%</td><td>42.1%</td></tr>
<tr><td>>tr|G3I7Y4|G3I7Y4_ CRIGR Ubiquitin-protein ligase E3A (Fragment)</td><td>55.6%</td><td>44.4%</td><td>0.0%</td><td>0.0%</td><td>0.0%</td><td>80.0%</td><td>20.0%</td><td>0.0%</td></tr>
<tr><td>>tr|G3I6T1|G3I6T1_ CRIGR Phospholipase B-like</td><td>53.2%</td><td>22.6%</td><td>11.3%</td><td>12.9%</td><td>8.0%</td><td>11.5%</td><td>19.5%</td><td>61.1%</td></tr>
<tr><td>>tr|G3I5N6|G3I5N6_ CRIGR IGFBP4</td><td>50.0%</td><td>33.3%</td><td>0.0%</td><td>16.7%</td><td>33.3%</td><td>13.9%</td><td>8.3%</td><td>44.4%</td></tr>
<tr><td>>tr|G3INC5|G3INC5_ CRIGR Cathepsin L1</td><td>47.3%</td><td>0.0%</td><td>12.7%</td><td>40.0%</td><td>25.6%</td><td>0.0%</td><td>25.6%</td><td>48.8%</td></tr>
<tr><td>>tr|G3GTT2|G3GTT2_ CRIGR C-C motif chemokine</td><td>55.6%</td><td>0.0%</td><td>0.0%</td><td>44.4%</td><td>30.0%</td><td>0.0%</td><td>20.0%</td><td>50.0%</td></tr>
<tr><td>>tr|G3I3K5|G3I3K5_ CRIGR G-protein coupled receptor 56</td><td>63.2%</td><td>0.0%</td><td>13.2%</td><td>23.7%</td><td>51.2%</td><td>7.3%</td><td>22.0%</td><td>19.5%</td></tr>
<tr><td>>tr|G3IG05|G3IG05_ CRIGR Annexin</td><td>55.8%</td><td>3.8%</td><td>5.8%</td><td>34.6%</td><td>47.6%</td><td>14.3%</td><td>9.5%</td><td>28.6%</td></tr>
<tr><td>>P02768ups|ALBU_ HUMAN_UPS Serum albumin (Chain 26-609)-Homo sapiens (Human)</td><td>27.7%</td><td>0.8%</td><td>57.1%</td><td>14.3%</td><td>14.7%</td><td>0.0%</td><td>55.2%</td><td>30.2%</td></tr>
<tr><td>>tr|G3H3Z4|G3H3Z4_ CRIGR SWI/SNF-related matrix-associated actin-dependent regulator</td><td>26.9%</td><td>23.1%</td><td>9.6%</td><td>40.4%</td><td>32.1%</td><td>20.8%</td><td>22.6%</td><td>24.5%</td></tr>
<tr><td>>tr|G3INL9|G3INL9_ CRIGR CMP-N-acetylneuraminate-beta-galactosamide-alpha-2, 3-sialyltransferase</td><td>48.6%</td><td>0.0%</td><td>51.4%</td><td>0.0%</td><td>48.0%</td><td>0.0%</td><td>52.0%</td><td>0.0%</td></tr>
<tr><td>>P62988ups|UBIQ_ HUMAN_UPS Ubiquitin (Chain 1-76, N-terminal His tag)-Homo sapiens (Human)</td><td>45.5%</td><td>0.0%</td><td>27.3%</td><td>27.3%</td><td>21.6%</td><td>3.9%</td><td>9.8%</td><td>64.7%</td></tr>
<tr><td>>tr|G3H533|G3H533_ CRIGR Peptidyl-prolyl cis-trans isomerase</td><td>37.6%</td><td>5.8%</td><td>7.5%</td><td>49.1%</td><td>23.2%</td><td>6.3%</td><td>8.9%</td><td>61.6%</td></tr>
<tr><td>>tr|G3I664|G3I664_ CRIGR Procollagen C-endopeptidase enhancer 1</td><td>36.4%</td><td>0.0%</td><td>0.0%</td><td>63.6%</td><td>34.6%</td><td>0.0%</td><td>3.8%</td><td>61.5%</td></tr>
<tr><td>>tr|G3HTK8|G3HTK8_ CRIGR Acyl-CoA-binding protein</td><td>37.5%</td><td>25.0%</td><td>0.0%</td><td>37.5%</td><td>0.0%</td><td>100.0%</td><td>0.0%</td><td>0.0%</td></tr>
<tr><td>>tr|G3HSL4|G3HSL4_ CRIGR Elongation factor 2</td><td>25.0%</td><td>25.0%</td><td>8.3%</td><td>41.7%</td><td>0.0%</td><td>15.4%</td><td>23.1%</td><td>61.5%</td></tr>
<tr><td>>tr|G3GVW2|G3GVW2_ CRIGR Putative hydrolase RBBP9</td><td>25.0%</td><td>0.0%</td><td>8.3%</td><td>66.7%</td><td>0.0%</td><td>0.0%</td><td>0.0%</td><td>100.0%</td></tr>
<tr><td>>tr|G3I936|G3I936_ CRIGR Epididymal secretory protein E1</td><td>19.0%</td><td>0.0%</td><td>0.0%</td><td>81.0%</td><td>0.0%</td><td>0.0%</td><td>0.0%</td><td>100.0%</td></tr>
<tr><td>>tr|G3GUK0|G3GUK0_ CRIGR Putative fructose-2,6-bisphosphatase TIGAR</td><td>22.2%</td><td>38.9%</td><td>22.2%</td><td>16.7%</td><td>23.3%</td><td>13.3%</td><td>33.3%</td><td>30.0%</td></tr>
<tr><td>>tr|Q9EPP7|Q9EPP7_ CRIGR CTSZ</td><td>22.0%</td><td>0.0%</td><td>6.0%</td><td>72.0%</td><td>8.5%</td><td>0.0%</td><td>8.5%</td><td>83.0%</td></tr>
<tr><td>>tr|G3HN27|G3HN27_ CRIGR Semaphorin-3A</td><td>21.8%</td><td>35.6%</td><td>42.6%</td><td>0.0%</td><td>27.0%</td><td>34.8%</td><td>38.2%</td><td>0.0%</td></tr>
<tr><td>>tr|G3I4H6|G3I4H6_ CRIGR Fructose-bisphosphate aldolase</td><td>21.2%</td><td>4.1%</td><td>4.1%</td><td>70.5%</td><td>31.4%</td><td>2.0%</td><td>5.9%</td><td>60.8%</td></tr>
<tr><td>>tr|G3I7X9|G3I7X9_ CRIGR Liver carboxylesterase 1</td><td>18.9%</td><td>0.0%</td><td>29.7%</td><td>51.4%</td><td>17.2%</td><td>0.0%</td><td>37.9%</td><td>44.8%</td></tr>
<tr><td>>sp|G3I8R9|BIP_CRIGR Endoplasmic reticulum chaperone Bip</td><td>16.7%</td><td>0.0%</td><td>10.0%</td><td>73.3%</td><td>12.5%</td><td>0.0%</td><td>9.7%</td><td>77.8%</td></tr>
</table>

TABLE 2-continued

Host cell protein separation by size exclusion chromatography in native or denaturing conditions

| | Native | | | | Denaturing (20% acetonitrile) | | | |
|---|---|---|---|---|---|---|---|---|
| HCP | HMW | Main | Tail | LMW | HMW | Main | Tail | LMW |
| >tr\|G3HGT4\|G3HGT4_ CRIGR Uncharacterized protein KIAA0564-like | 13.5% | 36.5% | 33.8% | 16.2% | 15.3% | 37.5% | 27.8% | 19.4% |
| >tr\|G3I7X5\|G3I7X5_ CRIGR Liver carboxylesterase 4 | 12.1% | 0.0% | 48.5% | 39.4% | 17.9% | 0.0% | 33.3% | 48.7% |
| >tr\|G3I5L0\|G3I5L0_ CRIGR Liver carboxylesterase 4 | 8.4% | 1.3% | 63.7% | 26.5% | 14.0% | 2.2% | 47.8% | 36.0% |
| >tr\|G3H892\|G3H892_ CRIGR Aminoacylase-1A | 23.1% | 76.9% | 0.0% | 0.0% | 20.7% | 0.0% | 79.3% | 0.0% |
| >tr\|G3HAR0\|G3HAR0_ CRIGR Fer-1-like protein 4 | 0.0% | 100.0% | 0.0% | 0.0% | 15.0% | 35.0% | 50.0% | 0.0% |
| >tr\|G3HI03\|G3HI03_ CRIGR U4/U6 small nuclear ribonucleoprotein Prp4 | 0.0% | 100.0% | 0.0% | 0.0% | 0.0% | 1.6% | 45.3% | 53.1% |
| >tr\|G3IG81\|G3IG81_ CRIGR NEDD4-binding protein 2 | 0.0% | 100.0% | 0.0% | 0.0% | 0.0% | 0.0% | 0.0% | 100.0% |
| >tr\|G3GRS9\|G3GRS9_ CRIGR N-acetylgalactosamine-6-sulfatase | 0.0% | 0.0% | 63.0% | 37.0% | 5.0% | 0.0% | 74.0% | 21.0% |
| >tr\|G3I1R6\|G3I1R6_ CRIGR Epididymal secretory protein E3-beta | 0.0% | 0.0% | 42.9% | 57.1% | 0.0% | 0.0% | 60.0% | 40.0% |
| >tr\|G3HD51\|G3HD51_ CRIGR LisH domain and HEAT repeat-containing protein KIAA1468 | 0.0% | 0.0% | 0.0% | 100.0% | 0.0% | 0.0% | 47.0% | 53.0% |
| >tr\|G3H3C3\|G3H3C3_ CRIGR Serine/threonine-protein kinase Nek1 | 0.0% | 0.0% | 44.4% | 55.6% | 0.0% | 0.0% | 42.9% | 57.1% |
| >tr\|G3I234\|G3I234_ CRIGR Protein FAM55A (Fragment) | 0.0% | 0.0% | 42.9% | 57.1% | 0.0% | 0.0% | 41.2% | 58.8% |
| >tr\|G3IQ82\|G3IQ82_ CRIGR Uncharacterized protein KIAA1267 | 0.0% | 0.0% | 0.0% | 100.0% | 0.0% | 0.0% | 33.3% | 66.7% |
| >tr\|G3I5K8\|G3I5K8_ CRIGR Carboxylic ester hydrolase | 0.0% | 0.0% | 100.0% | 0.0% | 0.0% | 0.0% | 16.7% | 83.3% |
| >P01031ups\|CO5_ HUMAN_UPS Complement C5 (C5a anaphylatoxin) (Chain 678-751)-Homo sapiens (Human) | 0.0% | 0.0% | 0.0% | 100.0% | 5.7% | 0.0% | 0.0% | 94.3% |
| >P62937ups\|PPIA_ HUMAN_UPS Peptidyl-prolyl cis-trans isomerase A (Chain 1-165, N terminal His tag)-Homo sapiens (Human) | 0.0% | 0.0% | 0.0% | 100.0% | 2.4% | 0.0% | 0.0% | 97.6% |
| >tr\|G3HXI5\|G3HXI5_ CRIGR Peptidylprolyl isomerase domain and WD repeat-containing protein 1 | 0.0% | 0.0% | 20.0% | 80.0% | 0.0% | 0.0% | 0.0% | 100.0% |
| >P61626ups\|LYSC_ HUMAN_UPS Lysozyme C (Chain 19-148)-Homo sapiens (Human) | 0.0% | 0.0% | 0.0% | 100.0% | 0.0% | 0.0% | 0.0% | 100.0% |
| >tr\|G3GVD0\|G3GVD0_ CRIGR ACTB | 0.0% | 0.0% | 0.0% | 100.0% | 0.0% | 0.0% | 0.0% | 100.0% |
| >tr\|G3HH92\|G3HH92_ CRIGR Pirin | 0.0% | 0.0% | 0.0% | 100.0% | 0.0% | 0.0% | 0.0% | 100.0% |
| >tr\|G3HNJ3\|G3HNJ3_ CRIGR Clusterin | 0.0% | 0.0% | 0.0% | 100.0% | 0.0% | 0.0% | 0.0% | 100.0% |
| >tr\|G3HCH0\|G3HCH0_ CRIGR MYDGF | 0.0% | 0.0% | 0.0% | 100.0% | 0.0% | 0.0% | 0.0% | 100.0% |
| >tr\|G3GU60\|G3GU60_ CRIGR Phosphatidylethanolamine-binding protein 1 | 0.0% | 0.0% | 0.0% | 100.0% | 0.0% | 0.0% | 0.0% | 100.0% |
| >tr\|G3H0U6\|G3H0U6_ CRIGR Protein disulfide-isomerase A3 | 0.0% | 0.0% | 0.0% | 100.0% | 0.0% | 0.0% | 0.0% | 100.0% |

TABLE 2-continued

<table>
<tr><th colspan="9">Host cell protein separation by size exclusion chromatography in native or denaturing conditions</th></tr>
<tr><th></th><th colspan="4">Native</th><th colspan="4">Denaturing (20% acetonitrile)</th></tr>
<tr><th>HCP</th><th>HMW</th><th>Main</th><th>Tail</th><th>LMW</th><th>HMW</th><th>Main</th><th>Tail</th><th>LMW</th></tr>
<tr><td>>tr|G3H1D5|G3H1D5_ CRIGR Carboxypeptidase</td><td>0.0%</td><td>0.0%</td><td>0.0%</td><td>100.0%</td><td>0.0%</td><td>0.0%</td><td>0.0%</td><td>100.0%</td></tr>
<tr><td>>tr|G3I973|G3I973_ CRIGR Hypoxia up-regulated protein 1</td><td>0.0%</td><td>0.0%</td><td>0.0%</td><td>100.0%</td><td>0.0%</td><td>0.0%</td><td>0.0%</td><td>100.0%</td></tr>
<tr><td>>tr|G3HKD0|G3HKD0_ CRIGR Peptidyl-prolyl cis-trans isomerase</td><td>0.0%</td><td>0.0%</td><td>0.0%</td><td>100.0%</td><td>0.0%</td><td>0.0%</td><td>0.0%</td><td>100.0%</td></tr>
<tr><td>>tr|G3I278|G3I278_ CRIGR Laminin subunit beta-1</td><td>0.0%</td><td>0.0%</td><td>0.0%</td><td>100.0%</td><td>0.0%</td><td>0.0%</td><td>0.0%</td><td>100.0%</td></tr>
<tr><td>>tr|G3IE06|G3IE06_ CRIGR Transmembrane protein 132A</td><td>0.0%</td><td>0.0%</td><td>0.0%</td><td>100.0%</td><td>0.0%</td><td>0.0%</td><td>0.0%</td><td>100.0%</td></tr>
<tr><td>>tr|G3IBK2|G3IBK2_ CRIGR Filamin-A</td><td>0.0%</td><td>0.0%</td><td>0.0%</td><td>100.0%</td><td>0.0%</td><td>0.0%</td><td>0.0%</td><td>100.0%</td></tr>
<tr><td>>tr|G3HIQ0|G3HIQ0_ CRIGR Threonyl-tRNA synthetase, cytoplasmic</td><td>0.0%</td><td>0.0%</td><td>0.0%</td><td>100.0%</td><td>0.0%</td><td>0.0%</td><td>0.0%</td><td>100.0%</td></tr>
<tr><td>>tr|G3I018|G3I018_ CRIGR 26S proteasome non-ATPase regulatory subunit 7</td><td>0.0%</td><td>0.0%</td><td>0.0%</td><td>100.0%</td><td>0.0%</td><td>0.0%</td><td>0.0%</td><td>100.0%</td></tr>
<tr><td>>tr|G3IDD9|G3IDD9_ CRIGR 40S ribosomal protein S3</td><td>0.0%</td><td>0.0%</td><td>0.0%</td><td>100.0%</td><td>0.0%</td><td>0.0%</td><td>0.0%</td><td>100.0%</td></tr>
<tr><td>>tr| G3HG95|G3HG95_ CRIGR Lamin-A/C</td><td>11.1%</td><td>0.0%</td><td>0.0%</td><td>88.9%</td><td>33.3%</td><td>0.0%</td><td>0.0%</td><td>66.7%</td></tr>
<tr><td>>P00918ups|CAH2_ HUMAN_UPS Carbonic anhydrase 2 (Chain 2-260)-Homo sapiens (Human)</td><td>0.0%</td><td>0.0%</td><td>0.0%</td><td>99.4%</td><td>23.4%</td><td>0.0%</td><td>0.0%</td><td>76.6%</td></tr>
<tr><td>>tr|G3H9Z5|G3H9Z5_ CRIGR Epidermal growth factor receptor kinase substrate 8</td><td>41.0%</td><td>0.0%</td><td>0.0%</td><td>59.0%</td><td>60.9%</td><td>0.0%</td><td>0.0%</td><td>39.1%</td></tr>
<tr><td>>tr|G3IKC3|G3IKC3_ CRIGR Glutathione S-transferase Mu 6</td><td>48.3%</td><td>0.0%</td><td>16.8%</td><td>34.9%</td><td>66.7%</td><td>0.0%</td><td>0.0%</td><td>33.3%</td></tr>
<tr><td>>tr|G3HXN7|G3HXN7_ CRIGR Beta-hexosaminidase</td><td>53.9%</td><td>6.3%</td><td>15.6%</td><td>24.2%</td><td>76.1%</td><td>4.3%</td><td>13.0%</td><td>6.5%</td></tr>
<tr><td>>tr|G3I413|G3I413_ CRIGR Hexosyltransferase</td><td>47.8%</td><td>0.0%</td><td>26.1%</td><td>26.1%</td><td>100.0%</td><td>0.0%</td><td>0.0%</td><td>0.0%</td></tr>
<tr><td>>tr|G3HCW9|G3HCW9_ CRIGR Peroxiredoxin</td><td>33.3%</td><td>0.0%</td><td>0.0%</td><td>66.7%</td><td>100.0%</td><td>0.0%</td><td>0.0%</td><td>0.0%</td></tr>
<tr><td>>tr|G3GUR1|G3GUR1_ CRIGR Complement C1r-A subcomponent</td><td>58.5%</td><td>7.5%</td><td>26.4%</td><td>7.5%</td><td>100.0%</td><td>0.0%</td><td>0.0%</td><td>0.0%</td></tr>
<tr><td>>P15559ups|NQO1_ HUMAN_UPS NAD(P)H dehydrogenase [quinone] 1 (Chain 2-274)-Homo sapiens (Human)</td><td>0.0%</td><td>0.0%</td><td>0.0%</td><td>100.0%</td><td>100.0%</td><td>0.0%</td><td>0.0%</td><td>0.0%</td></tr>
<tr><td>>P02144ups|MYG_ HUMAN_UPS Myoglobin (Chain2-154)-Homo sapiens (Human)</td><td>0.0%</td><td>0.0%</td><td>0.0%</td><td>100.0%</td><td>95.0%</td><td>0.0%</td><td>0.0%</td><td>5.0%</td></tr>
<tr><td>>P68871ups|HBB_ HUMAN_UPS Hemoglobin subunit beta (Chain 2-147)-Homo sapiens (Human)</td><td>0.0%</td><td>0.0%</td><td>0.0%</td><td>100.0%</td><td>82.1%</td><td>3.6%</td><td>0.0%</td><td>14.3%</td></tr>
<tr><td>>P69905ups|HBA_ HUMAN_UPS Hemoglobin subunit alpha (Chain 2-142) - Homo sapiens (Human)</td><td>0.0%</td><td>0.0%</td><td>0.0%</td><td>100.0%</td><td>63.9%</td><td>0.0%</td><td>0.0%</td><td>36.1%</td></tr>
<tr><td>>P00915ups|CAH1_ HUMAN_UPS Carbonic anhydrase 1 (Chain 2-261)-Homo sapiens (Human)</td><td>0.0%</td><td>0.0%</td><td>0.6%</td><td>99.4%</td><td>61.4%</td><td>0.6%</td><td>0.0%</td><td>38.0%</td></tr>
<tr><td>>tr|G3H7B3|G3H7B3_ CRIGR Galectin</td><td>0.0%</td><td>0.0%</td><td>0.0%</td><td>100.0%</td><td>40.0%</td><td>0.0%</td><td>0.0%</td><td>60.0%</td></tr>
</table>

A comparison of the SEC separation of each HCP in each condition can be used to infer the binding properties of each HCP to the biotherapeutic. For example, HCPs that were found in the HMW fraction in both native and denaturing conditions could be inferred to have relatively strong binding to mAb1, which could not be dissociated by the mild denaturing of 20% acetonitrile, as shown in FIG. 18A. HCPs that were found in the LMW fraction in both conditions could be inferred to have effectively no binding to mAb1, as shown in FIG. 18B. HCPs that were found in the HMW fraction in the native condition but shifted to earlier fractions in the denaturing condition could be inferred to have relatively weak binding to mAb1 that was disrupted by 20% acetonitrile, as shown in FIG. 18C. HCPs that were found in a mix of HMW and other fractions in both conditions could be inferred to have relatively weak binding to mAb1 that was not affected by 20% acetonitrile. Finally, HCPs that were found predominantly in the HMW fraction in the denaturing condition but not in the native condition could be inferred to have binding that is re-equilibrated by acetonitrile.

Using this analysis, a binding profile of HCPs of particular interest for a given biotherapeutic can be generated. FIG. 19 shows a binding profile of HCPs of interest in mAb1 drug substance. For example, it was found that cathepsin D is bound to mAb1 in the purification process, but that this interaction is weak and can be disrupted using 20% acetonitrile. This HCP binding profile analysis can be used to inform process development for any biotherapeutic.

Example 5. Surfactant-Assisted Size Exclusion Chromatography Method for Host Cell Protein Analysis A surfactant-assisted dissociation method was developed to enrich HCPs from a biotherapeutic sample, informed by the HCP binding profile analysis described above.

Figure 20:
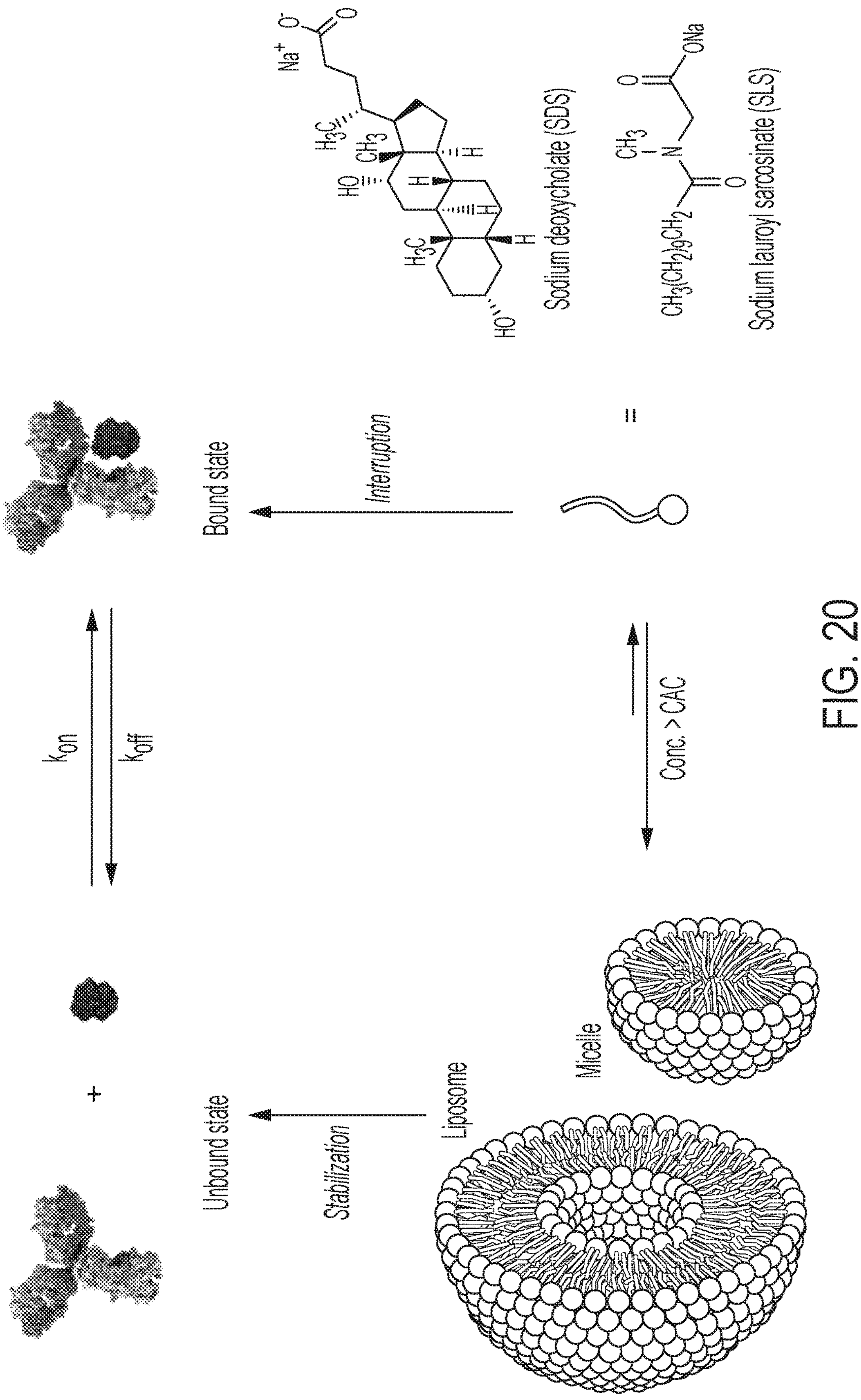
FIG. 20 illustrates the use of detergents to affect the equilibrium of bound and unbound HCPs in a biotherapeutic drug substance, according to an exemplary embodiment.
Figure 21:
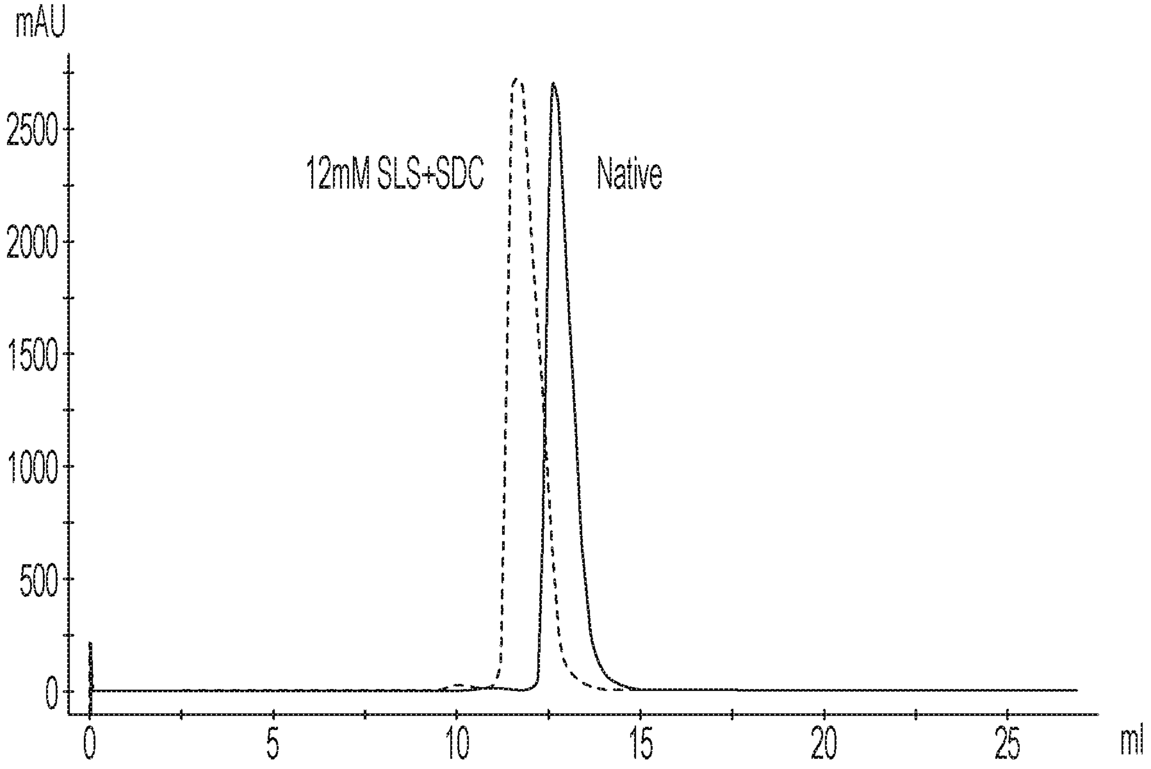
FIG. 21 shows an SEC chromatogram of mAb1 drug substance using the method of the present invention with native mobile phase or 12 mM SLS and SDC, according to an exemplary embodiment.

HCPs may exist in an equilibrium between a biotherapeutic-bound and unbound state, as shown in FIG. 20. In order to disrupt the bound state of this equilibrium and stabilize the unbound state, thereby preventing HCPs from co-purifying with a biotherapeutic, various detergents were tested as part of a biotherapeutic production process. An SEC separation profile of mAb1 sample was generated using either a native mobile phase or a mobile phase comprising 12 mM sodium lauroyl sarcosinate (SLS) and 12 mM sodium deoxycholate (SDC), as shown in FIG. 21. A shift in retention time was observed, indicating partial denaturation of the antibody and/or formation of a micelle/liposome.

Figure 22:
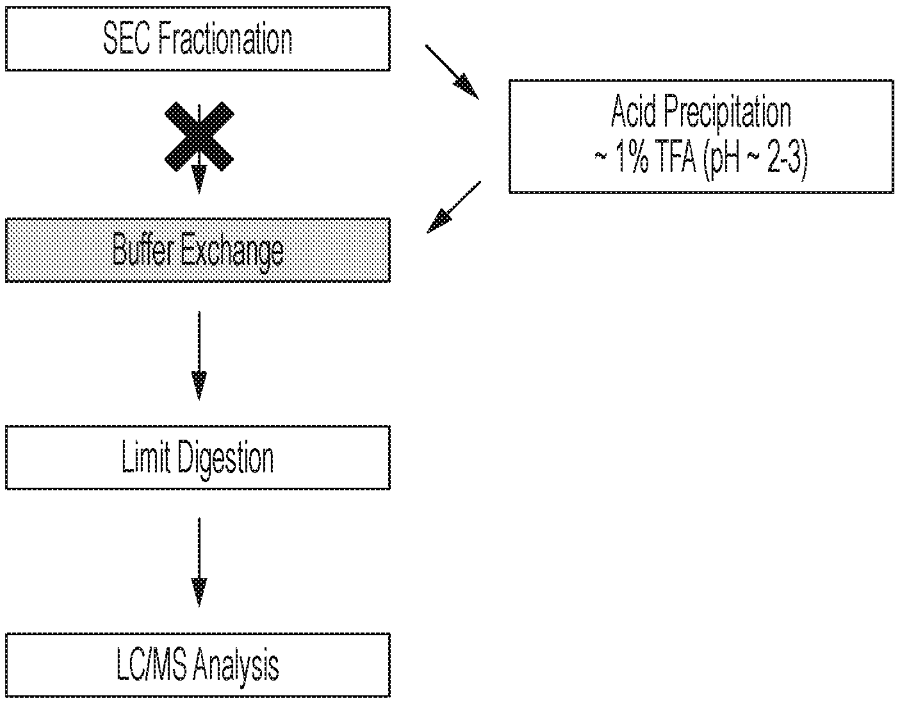
FIG. 22 shows a workflow of biotherapeutic analysis including an acid precipitation step to remove detergents, according to an exemplary embodiment.

High levels of surfactants can adversely affect digestion and MS analysis. Surfactants were found to be difficult to remove during buffer exchange. In order to solve the problem of effective surfactant removal prior to digestion and MS analysis, an optimized sample preparation method was developed, as shown in FIG. 22. An acid precipitation step using about 1% trifluoroacetic acid (TFA) was used to remove the surfactants prior to the buffer exchange step, which successfully removed SLS and SDC; this is referred to as the "surfactant-assisted" or "surfactant-aided" SEC method of the present invention.

Figure 23:
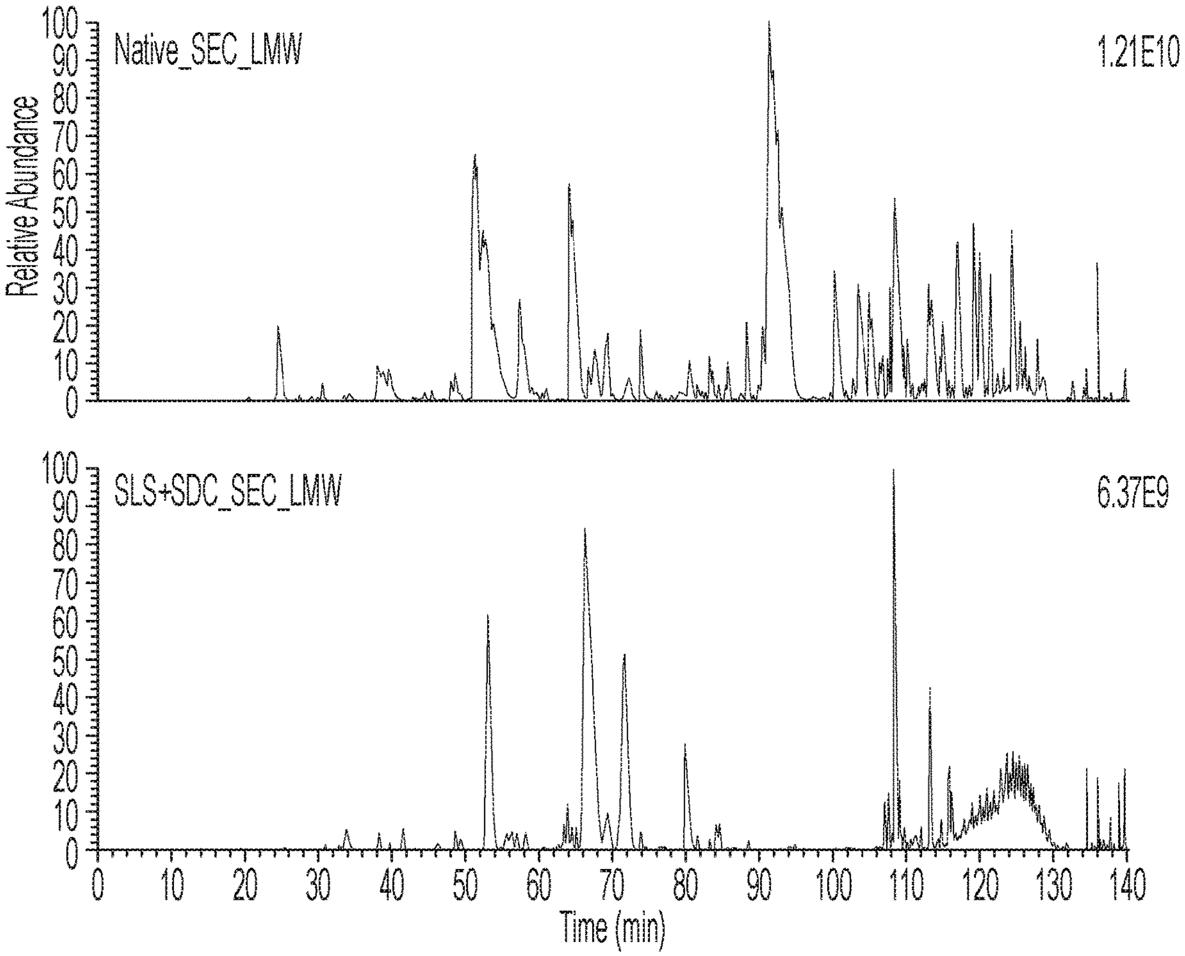
FIG. 23 shows a UV chromatogram of the LMW fraction of mAb1 drug substance with either native mobile phase or the surfactant-assisted and acid-precipitated process, according to an exemplary embodiment.
Figure 24A:
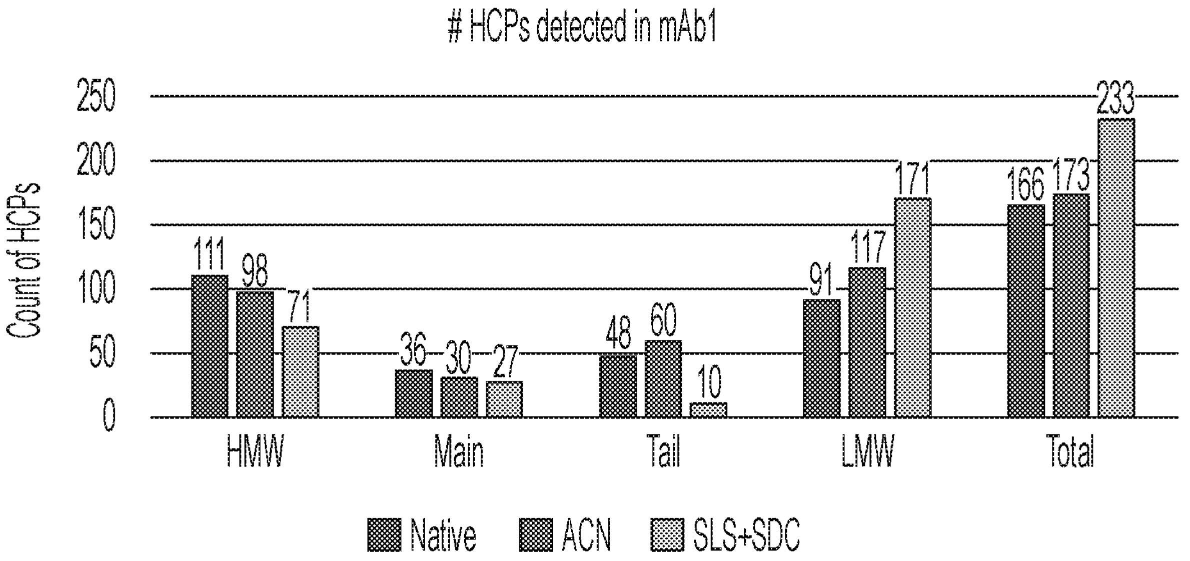
FIG. 24A shows the number of HCPs detected in each SEC fraction using native mobile phase, ACN mobile phase, or the surfactant-assisted and acid-precipitated process, according to an exemplary embodiment.
Figure 24B:
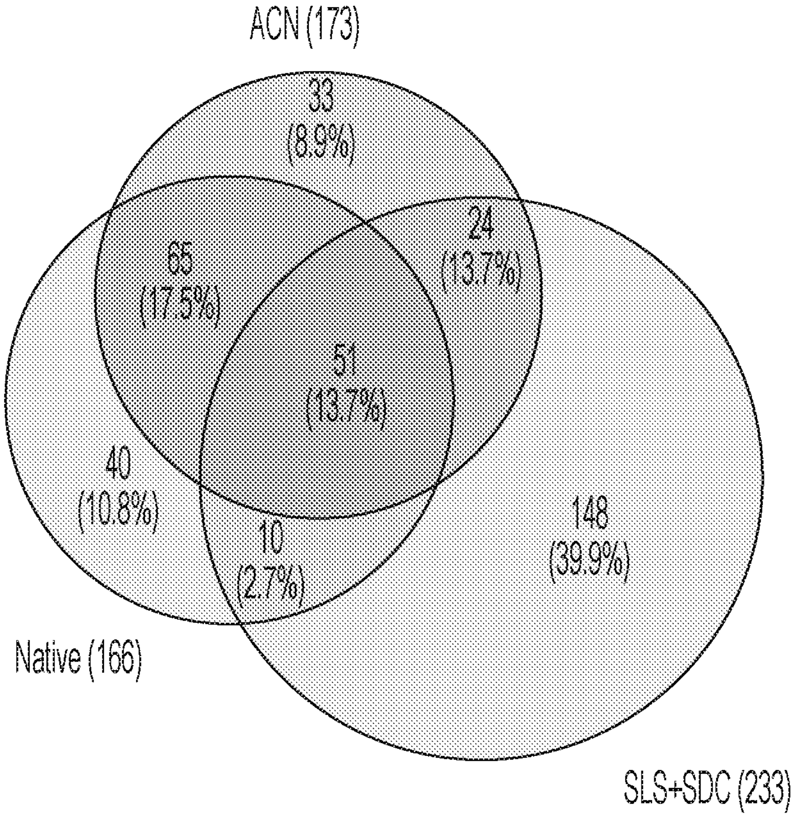
FIG. 24B shows the overlap in HCPs detected in mAb1 drug substance using native mobile phase, ACN mobile phase, or the surfactant-assisted and acid-precipitated process, according to an exemplary embodiment.

The effects of acid precipitation on HCP enrichment and analysis were further assessed. Acid precipitation led to the partial removal of mAb1, as shown in FIG. 23. The ability of the optimized surfactant-assisted method using SLS and SDC along with acid precipitation to detect HCPs in a mAb1 sample was compared to the method using a native mobile phase or ACN mobile phase, as shown in FIG. 24A and FIG. 24B. A greater number of HCPs were detected using the surfactant-assisted method compared to using the native or ACN mobile phases.

The sensitivity of the method was tested using UPS2 standard, and the surfactant-assisted method (SLS+SDC) was shown to be more sensitive than the method using native or ACN mobile phases, as shown in Table 3. Without being bound by theory, it is possible that the acid precipitation step preferentially precipitates mAb1 compared to HCPs due to the larger size of mAb1, thereby further enriching the sample for HCPs. This effect would be expected for any large protein of interest, for example an antibody or antibody fusion protein.

TABLE 3

UPS2 detected using native mobile phase, acetonitrile mobile phase or surfactant-assisted method

| Mobile Phase | # UPS2 Detected | 1.875 × $10^1$ ppm | 1.875 × $10^0$ ppm | 1.875 × $10^{-1}$ ppm | 1.875 × $10^{-2}$ ppm | 1.875 × $10^{-3}$ ppm | 1.875 × $10^{-4}$ ppm |
|---|---|---|---|---|---|---|---|
| Native | 15/48 | 7/8 | 4/8 | 2/8 | 1/8 | 1/8 | 0/8 |
| Acetonitrile | 16/48 | 7/8 | 7/8 | 1/8 | 1/8 | 0/8 | 0/8 |
| SLS + SDC | 17/48 | 7/8 | 4/8 | 1/8 | 1/8 | 2/8 | 2/8 |

The surfactant-assisted method shifted HCPs of interest from the HMW fraction to the LMW fraction, demonstrating the successful disruption of HCP binding to the biotherapeutic and improvement in HCP enrichment and analysis, as shown in FIG. 25.

Figure 26:
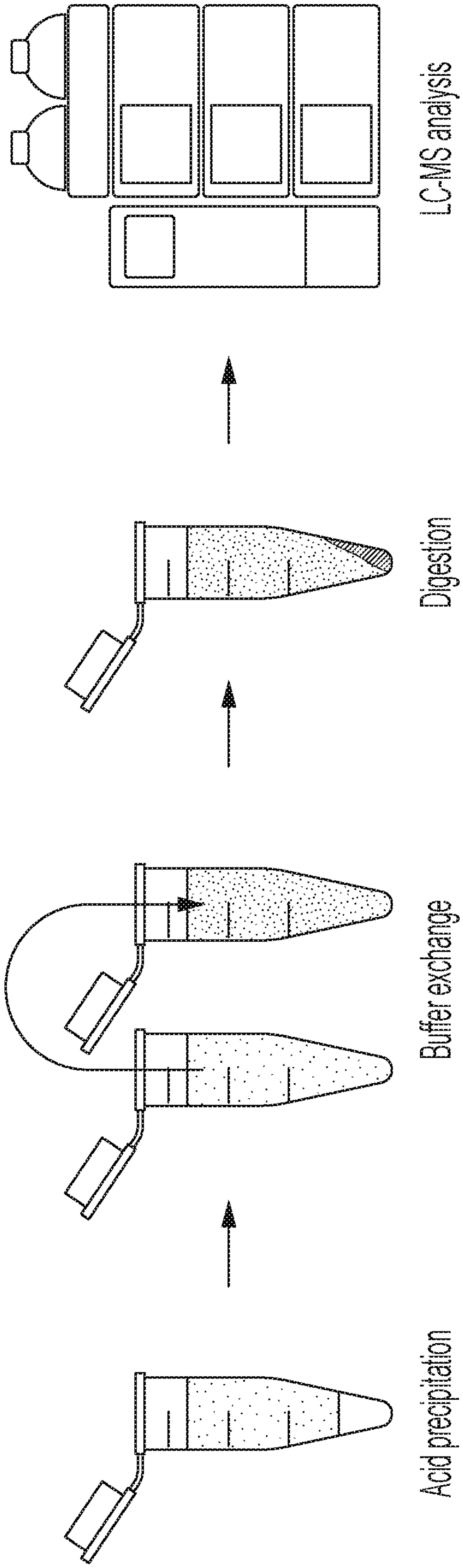
FIG. 26 shows a workflow of biotherapeutic analysis using a method of the present invention that includes surfactant-assisted dissociation and acid precipitation to remove surfactants and biotherapeutic, according to an exemplary embodiment.

Example 6. Optimization of a Surfactant-Assisted Acid Precipitation Method for Host Cell Protein Analysis FIG. 26 shows a workflow of a surfactant-assisted acid precipitation method that was used to enrich and identify HCPs in biotherapeutic samples. In the acid precipitation step, biotherapeutic samples were incubated in surfactants, followed by acids, and centrifuged to remove the surfactants and biotherapeutics. Ultraviolet absorption at 280 nm (UV A280) was used to determine the protein concentrations of samples after acid precipitation, which served as an indicator of the efficacy of acid precipitation parameters. Subsequently, sample buffers were exchanged, and biotherapeutic samples were digested, desalted and analyzed using nano liquid chromatography-mass spectrometry and Protein Metrics Byonic. The clarity of the spectra in the total ion chromatograms and host cell protein identification also served as indicators of the efficacy of acid precipitation parameters.

Figure 27A:
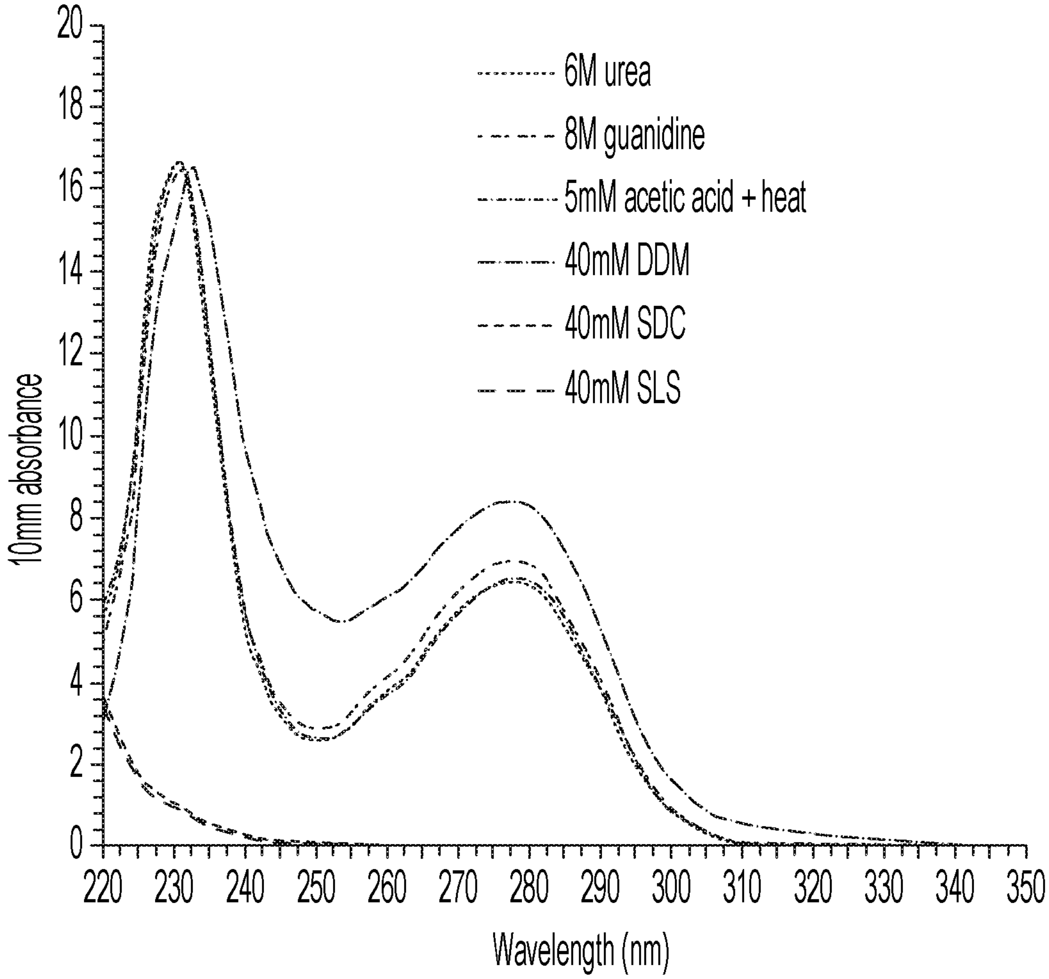
FIG. 27A shows the protein spectra of biotherapeutic samples at 280 nm following incubation in 6 M urea, 8 M guanidine, 5 mM acetic acid with heat, 40 mM sodium deoxycholate, 40 mM sodium lauroyl sarcosinate or 40 mM n-dodecyl-β-D-maltoside and acid precipitation, according to an exemplary embodiment.
Figure 27B:
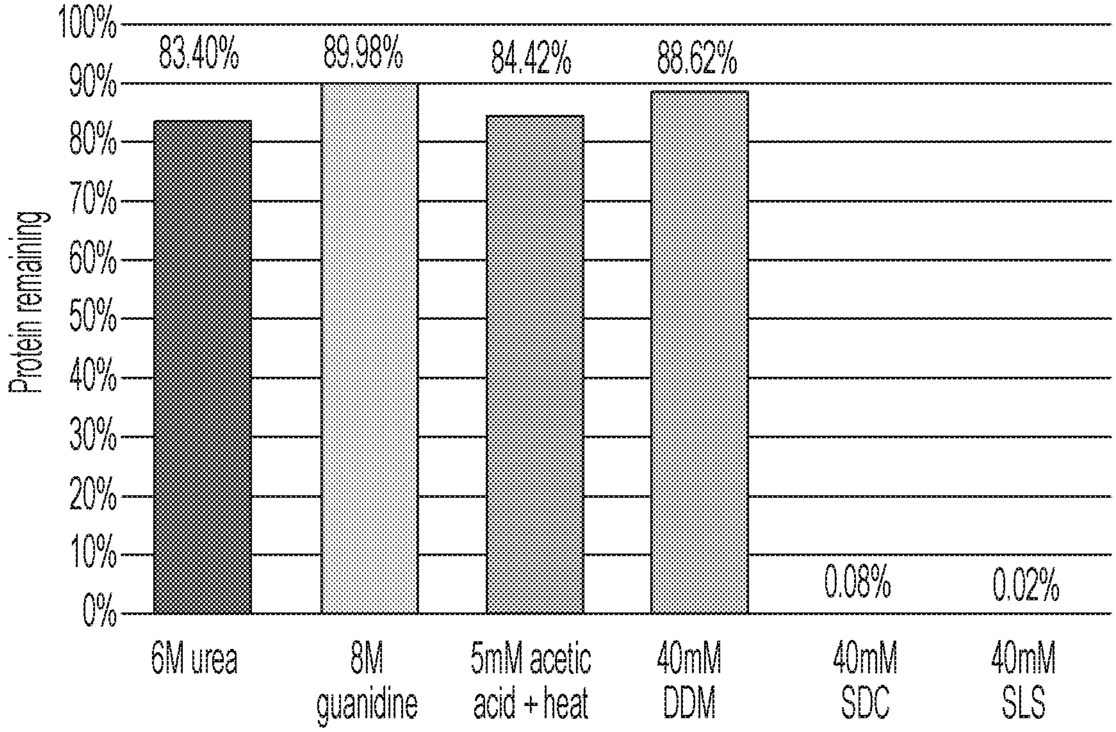
FIG. 27B shows the percentage of protein remaining in biotherapeutic samples following incubation in 6 M urea, 8 M guanidine, 5 mM acetic acid with heat, 40 mM sodium deoxycholate, 40 mM sodium lauroyl sarcosinate or 40 mM n-dodecyl-β-D-maltoside and acid precipitation, according to an exemplary embodiment.

The effects various dissociation reagents have on protein in biotherapeutic samples subjected to acid precipitation were assessed. The surfactants sodium deoxycholate, sodium lauroyl sarcosinate and n-dodecyl-β-D-maltoside can be used as dissociation reagents. FIG. 27A and FIG. 27B show that acid precipitation depleted 99.92%, 99.98% and 11.38% of the protein in biotherapeutic samples that were incubated in 40 mM sodium deoxycholate, 40 mM sodium lauroyl sarcosinate and 40 mM n-dodecyl-β-D-maltoside, respectively. Additionally, 6 M urea, 8 M guanidine and 5 mM acetic acid with heat can be used as dissociation reagents. FIG. 27A and FIG. 27B show that acid precipitation depleted 16.6%, 10.02% and 15.58% of the protein in biotherapeutic samples that were incubated in 6 M urea, 8 M guanidine and 5 mM acetic acid with heat, respectively. These data demonstrate that sodium deoxycholate and sodium lauroyl sarcosinate are unique surfactants that can be used in conjunction with acid precipitation to deplete protein in biotherapeutic samples.

Figure 28A:
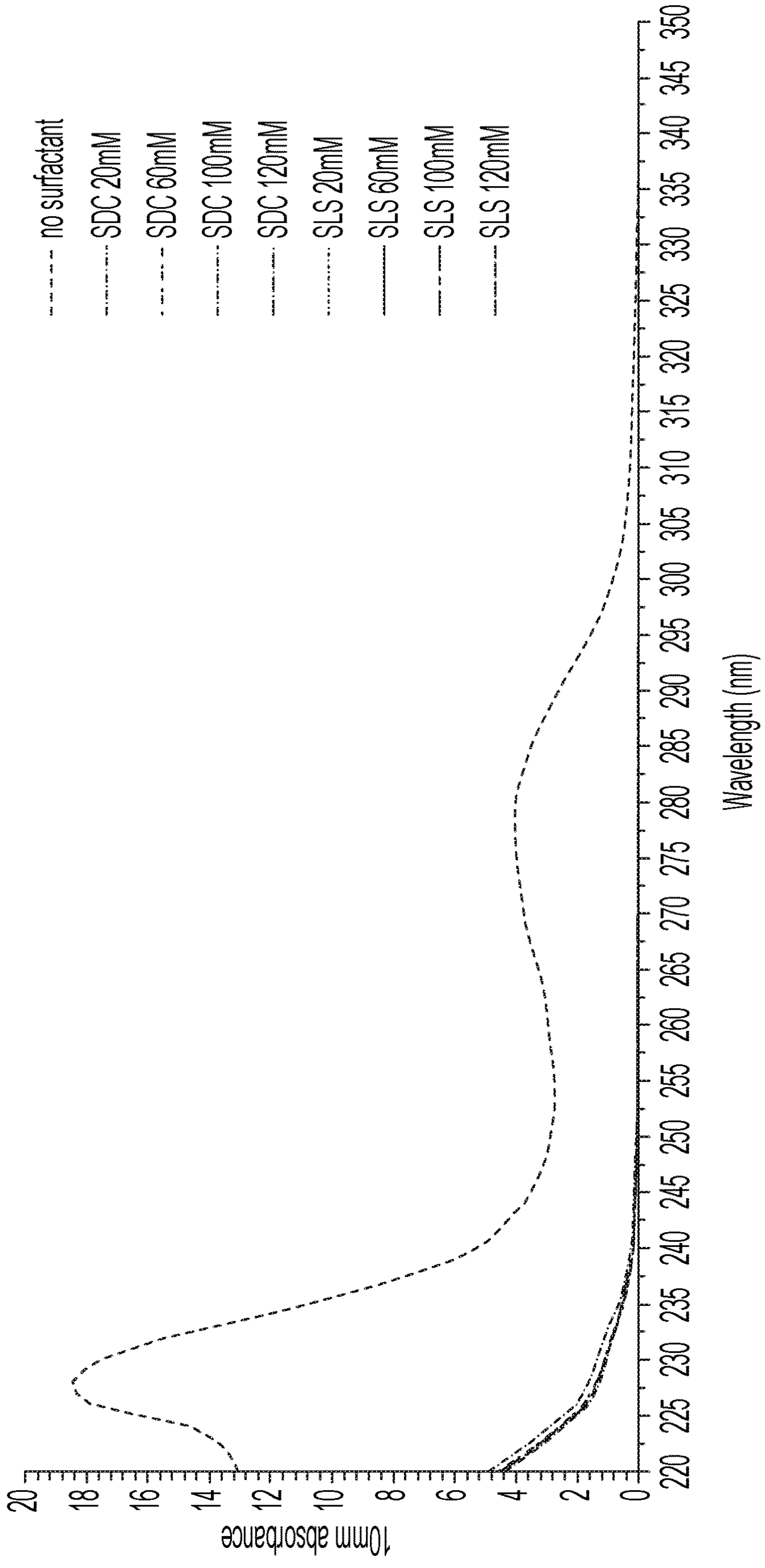
FIG. 28A shows the protein spectra of biotherapeutic samples at 280 nm after 500 L samples containing 5 mg of the biotherapeutic were incubated in 0 mM, 20 mM, 60 mM, 100 mM or 120 mM sodium deoxycholate or sodium lauroyl sarcosinate for 2 hours and 10% trifluoroacetic acid (v/v) for 30 minutes, according to an exemplary embodiment.
Figure 28B:
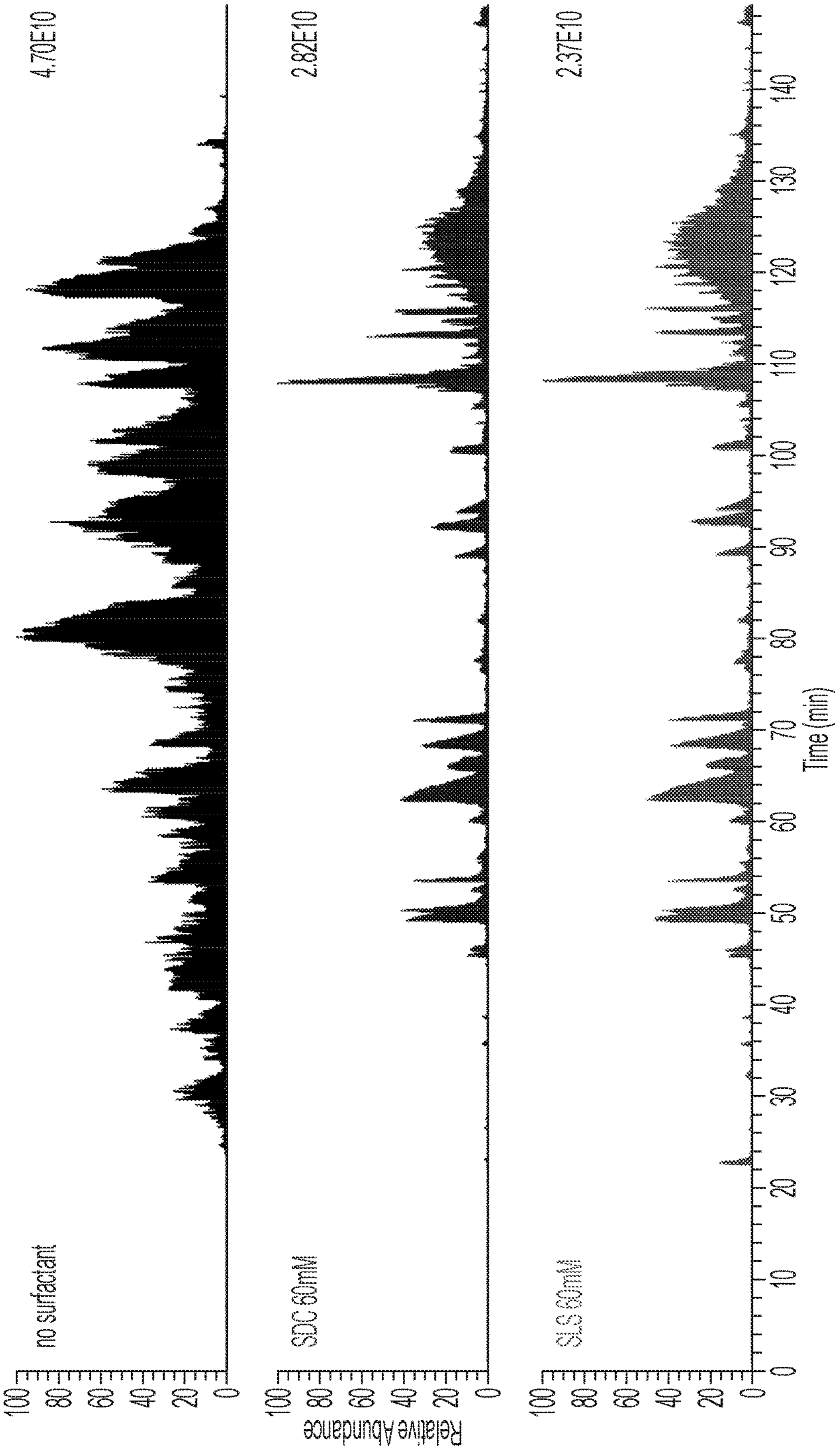
FIG. 28B shows the total ion chromatograms of biotherapeutic samples obtained using nano liquid chromatography-mass spectrometry after 500 μL samples containing 5 mg of the biotherapeutic were incubated in no surfactant (top panel), 60 mM sodium deoxycholate (middle panel) or 60 mM sodium lauroyl sarcosinate (bottom panel) for 2 hours and 10% trifluoroacetic acid (v/v) for 30 minutes, according to an exemplary embodiment.
Figure 29A:
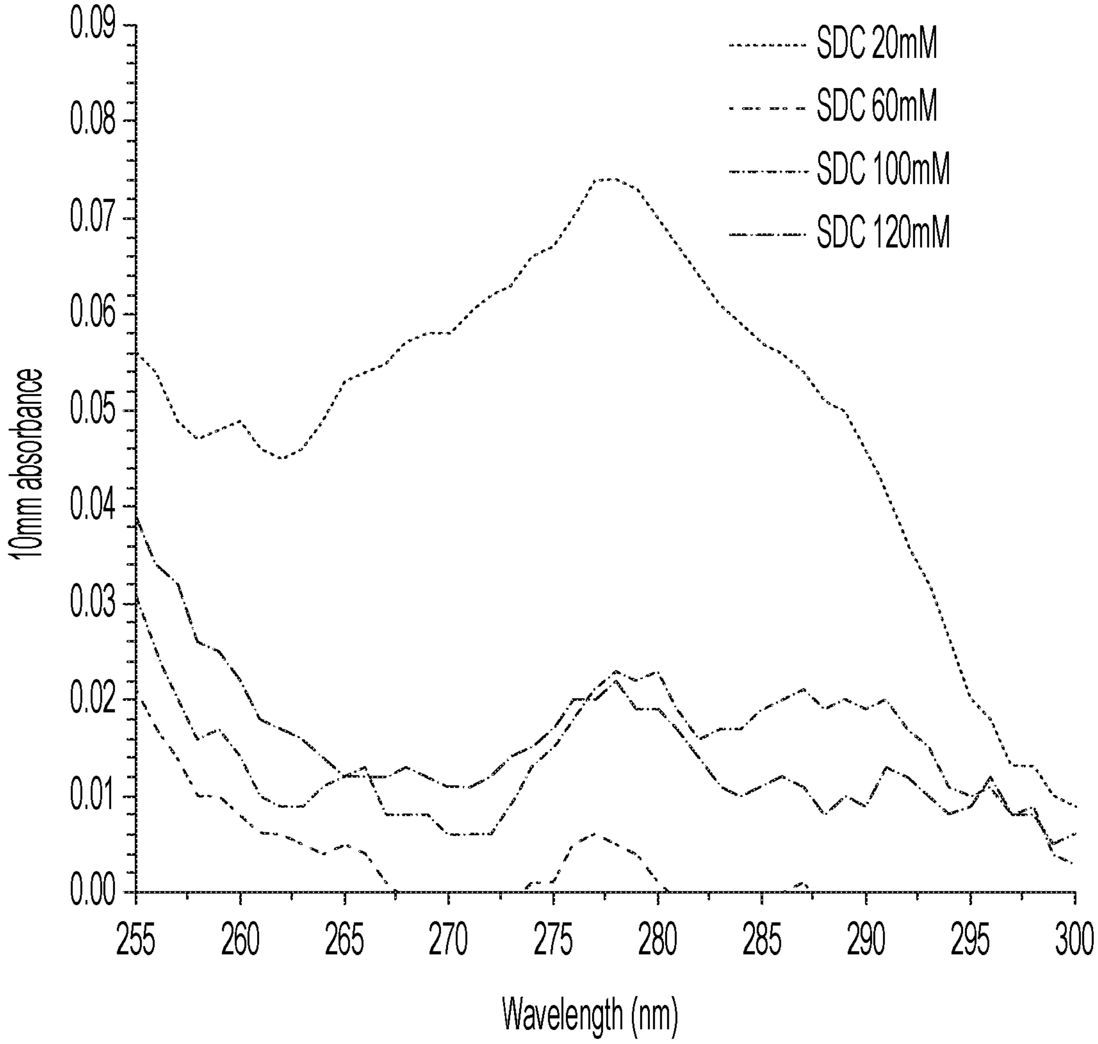
FIG. 29A shows the protein spectra of biotherapeutic samples at 280 nm after 500 L samples containing 5 mg of the biotherapeutic were incubated in 20 mM, 60 mM, 100 mM or 120 mM sodium deoxycholate for 2 hours and 10% trifluoroacetic acid (v/v) for 30 minutes, according to an exemplary embodiment.
Figure 29B:
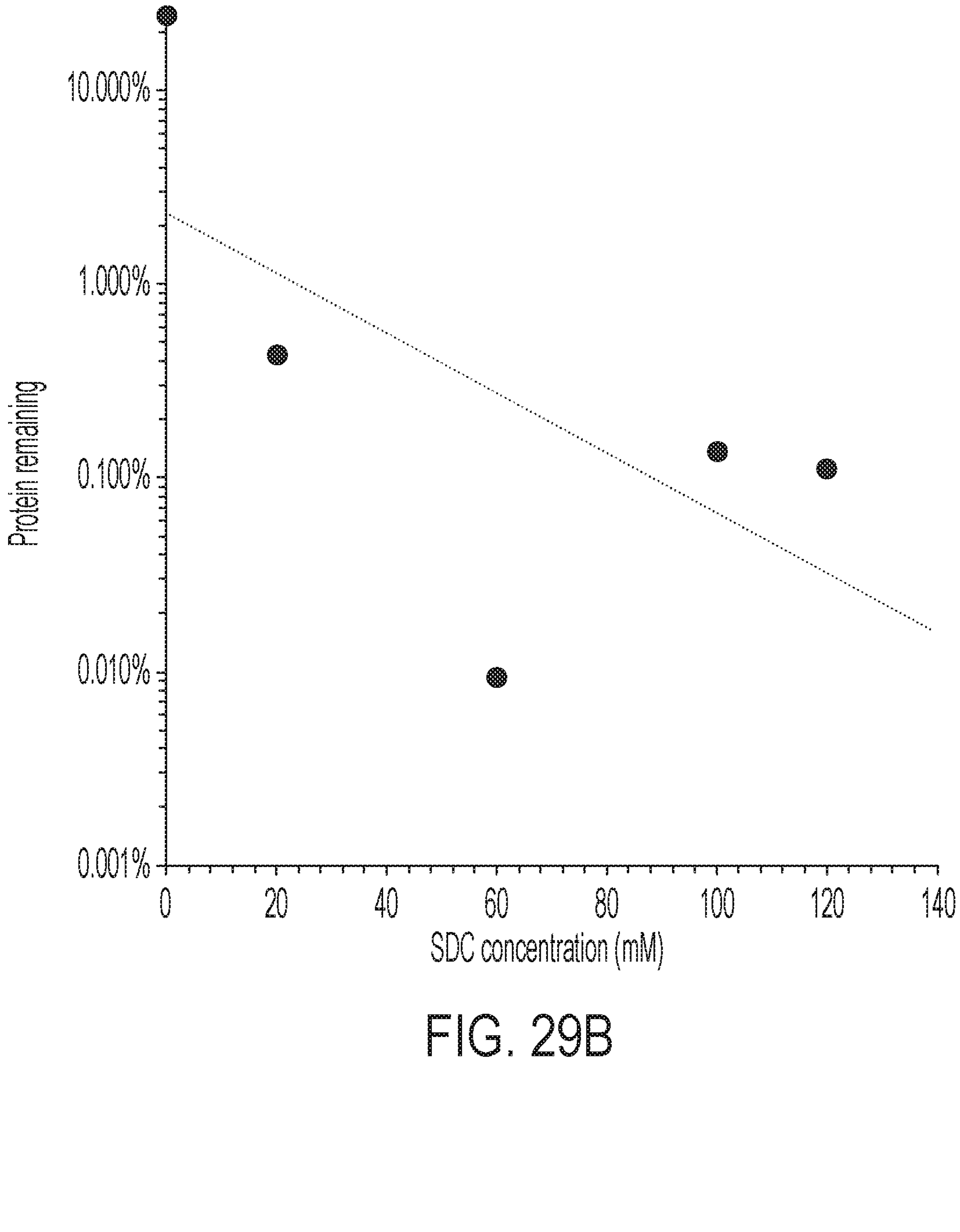
FIG. 29B shows the percentage of protein remaining in biotherapeutic samples after 500 μL samples containing 5 mg of the biotherapeutic were incubated in 20 mM, 60 mM, 100 mM or 120 mM sodium deoxycholate for 2 hours and 10% trifluoroacetic acid (v/v) for 30 minutes, according to an exemplary embodiment.
Figure 30A:
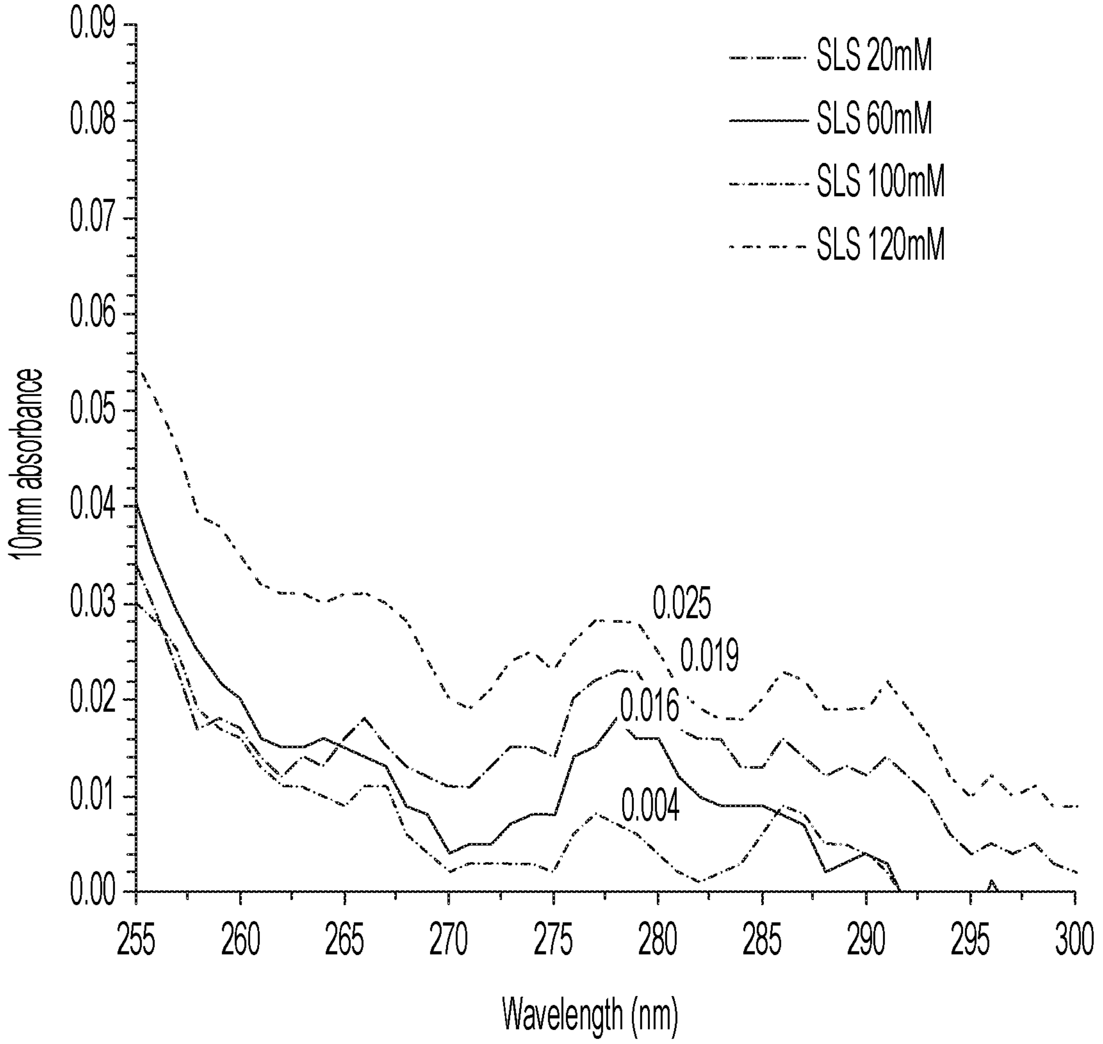
FIG. 30A shows the protein spectra of samples of a biotherapeutic at 280 nm after 500 μL samples containing 5 mg of the biotherapeutic were incubated in 20 mM, 60 mM, 100 mM or 120 mM sodium lauroyl sarcosinate for 2 hours and 10% trifluoroacetic acid (v/v) for 30 minutes, according to an exemplary embodiment.
Figure 30B:
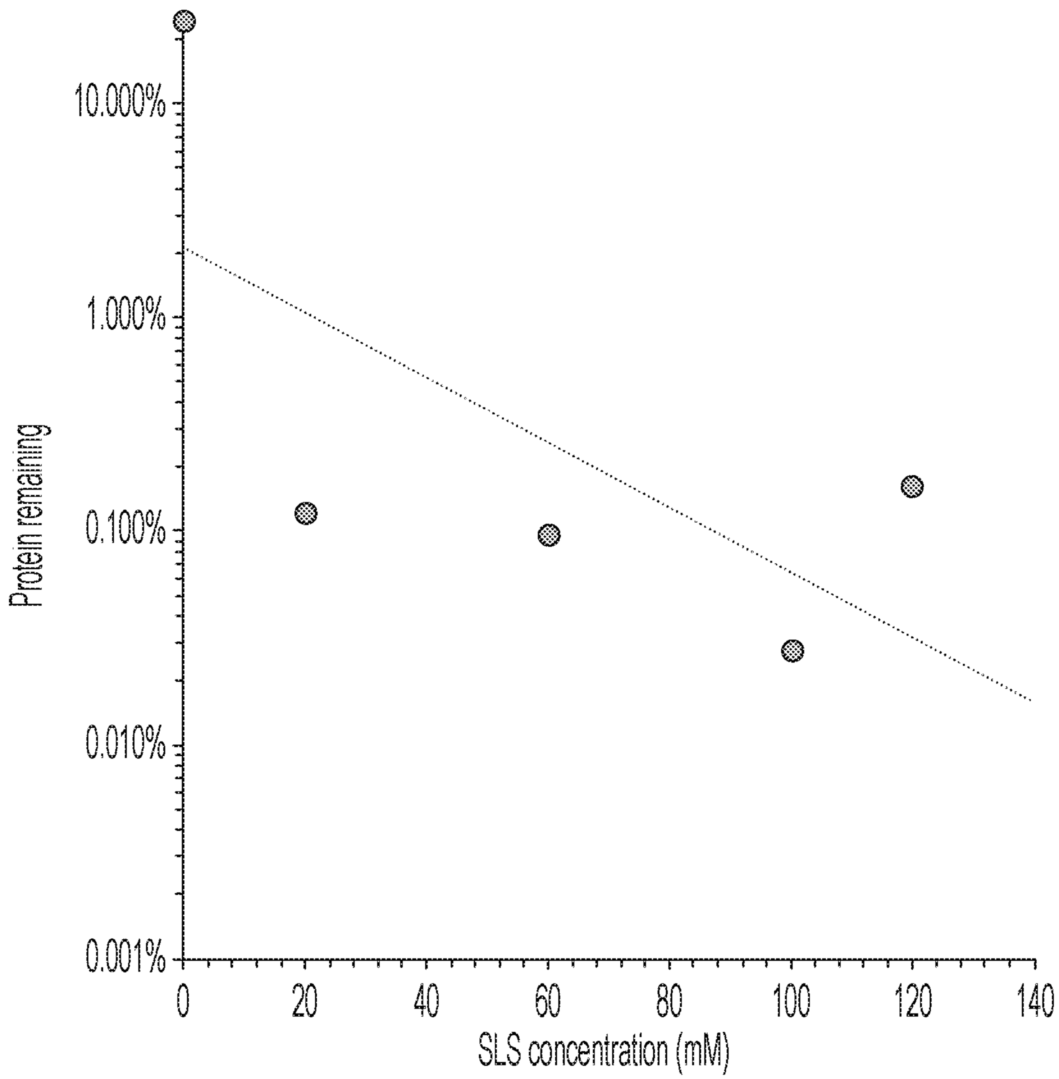
FIG. 30B shows the percentage of protein remaining in biotherapeutic samples after 500 μL samples containing 5 mg of the biotherapeutic were incubated in 20 mM, 60 mM, 100 mM or 120 mM sodium lauroyl sarcosinate for 2 hours and 10% trifluoroacetic acid (v/v) for 30 minutes, according to an exemplary embodiment.

The effects sodium deoxycholate and sodium lauroyl sarcosinate concentration have on protein depletion in biotherapeutic samples subjected to acid precipitation were examined. Each biotherapeutic sample was 500 μL, contained 5 mg of a biotherapeutic, and was incubated in 0 mM, 20 mM, 60, mM, 100 mM or 120 mM sodium deoxycholate or sodium lauroyl sarcosinate for 2 hours and 10% acid (v/v) for 30 minutes. FIG. 28 shows that acid precipitation depleted protein more effectively in biotherapeutic samples that were incubated in sodium deoxycholate or sodium lauroyl sarcosinate. FIG. 29 and FIG. 30 demonstrate that incubating biotherapeutic samples in 10% acid (v/v) for 30 minutes can deplete 99.5% of protein in biotherapeutic samples following incubation in 40 mM sodium deoxycholate and 40 mM sodium lauroyl sarcosinate for 2 hours, respectively.

Figure 31A:
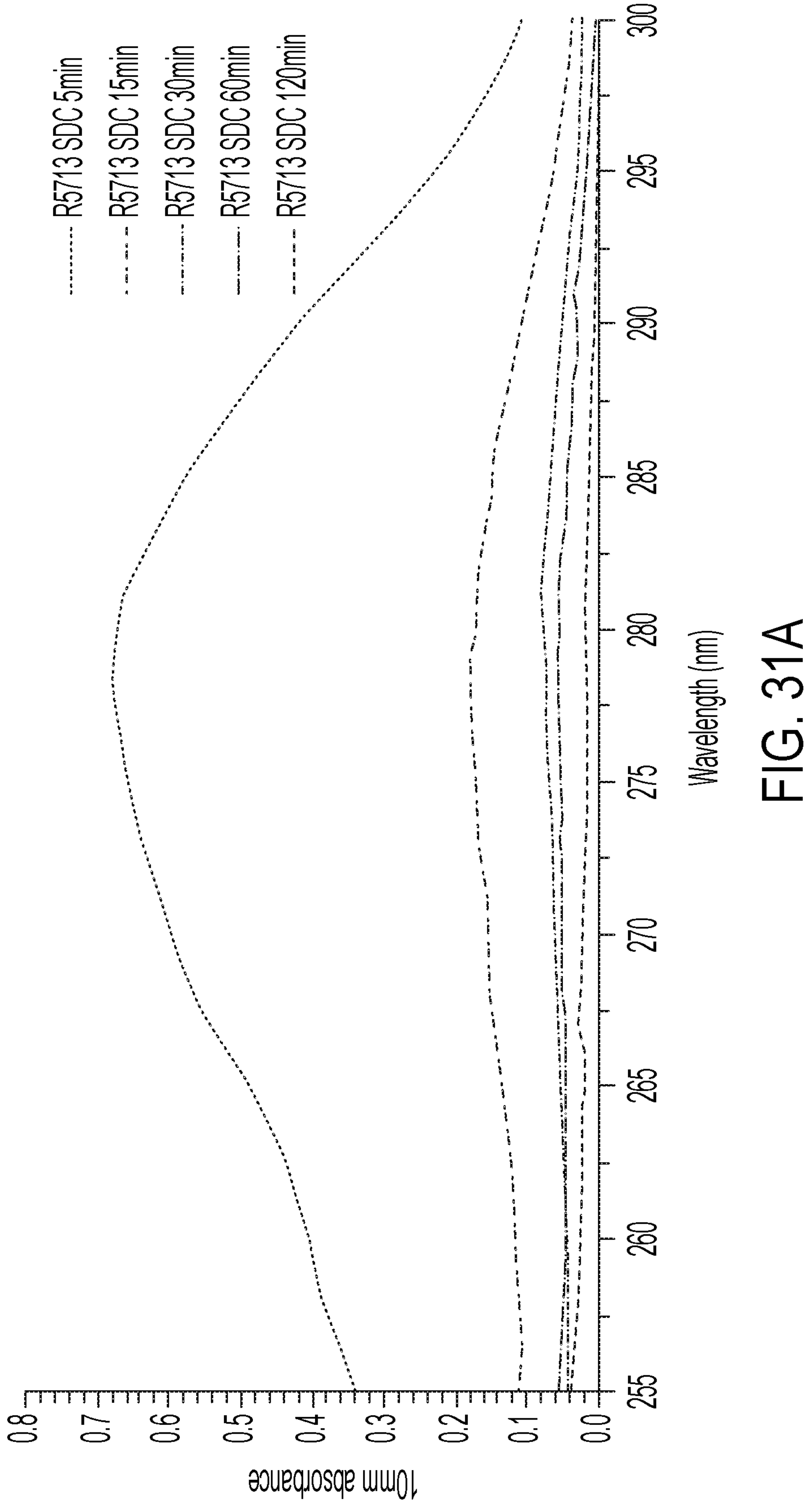
FIG. 31A shows the protein spectra of biotherapeutic samples at 280 nm after incubation in 20 mM sodium deoxycholate for 5 minutes, 15 minutes, 30 minutes, 60 minutes or 120 minutes and acid precipitation, according to an exemplary embodiment.
Figure 31B:
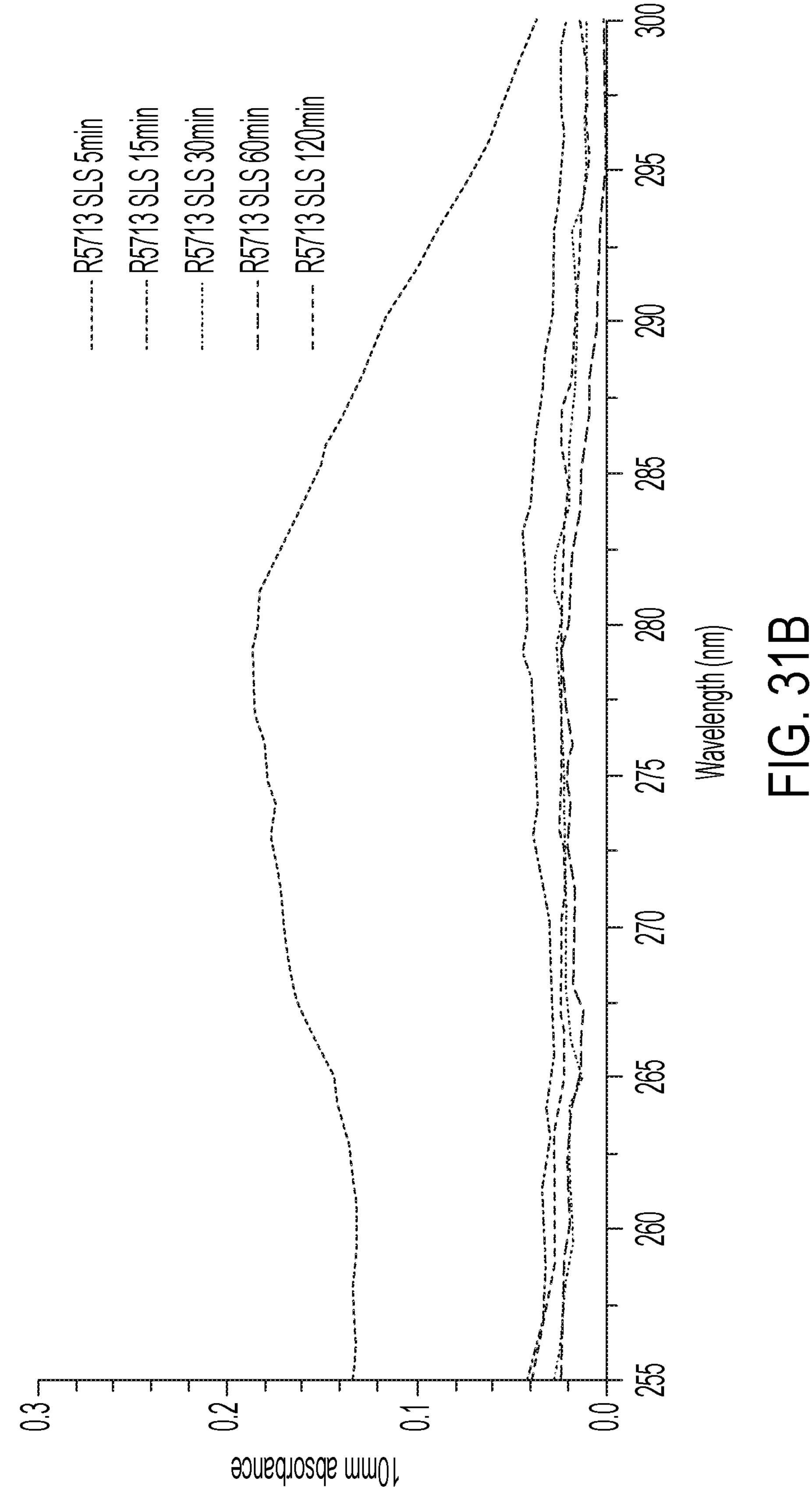
FIG. 31B shows the protein spectra of biotherapeutic samples at 280 nm after incubation in 20 mM sodium lauroyl sarcosinate for 5 minutes, 15 minutes, 30 minutes, 60 minutes or 120 minutes and acid precipitation, according to an exemplary embodiment.
Figure 31C:
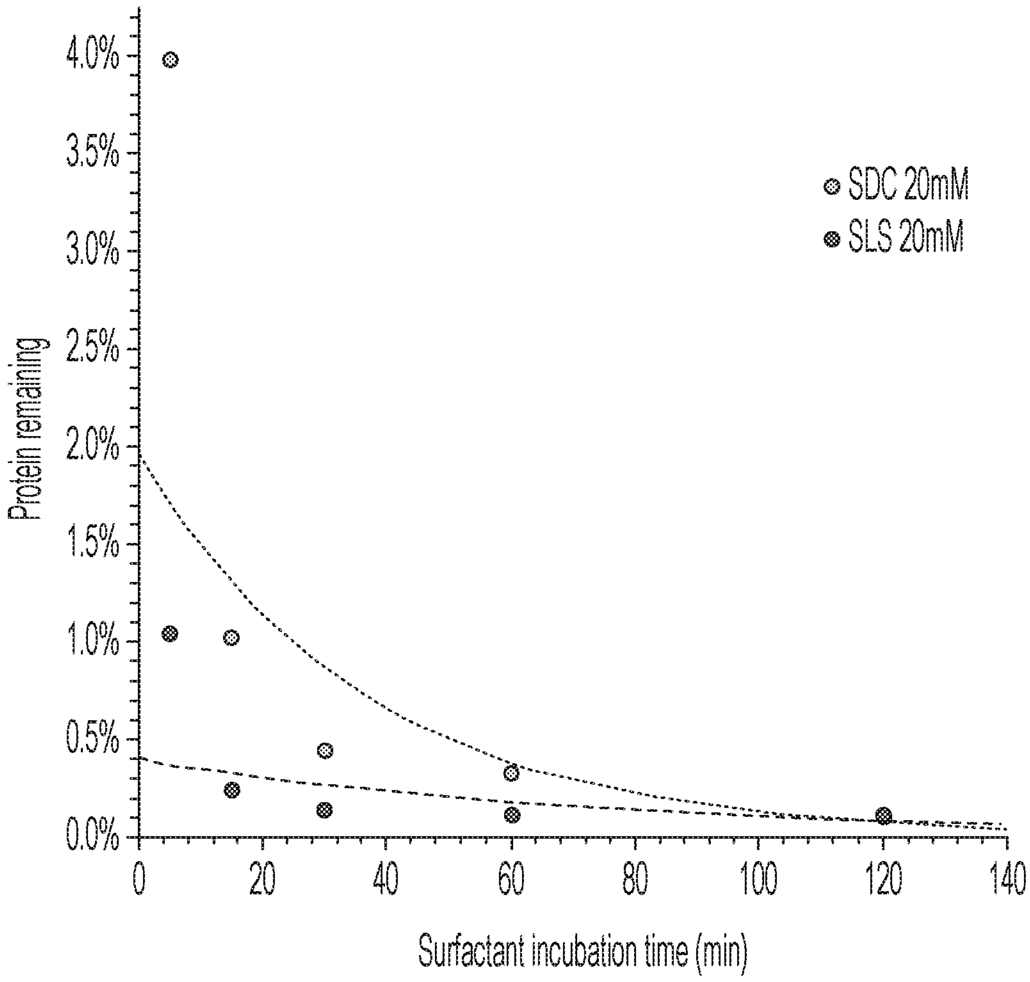
FIG. 31C shows the percentage of protein remaining in biotherapeutic samples after incubation in 20 mM sodium deoxycholate or 20 mM sodium lauroyl sarcosinate for 5 minutes, 15 minutes, 30 minutes, 60 minutes or 120 minutes and acid precipitation, according to an exemplary embodiment.

The effects that sodium deoxycholate and sodium lauroyl sarcosinate incubation time have on protein depletion in biotherapeutic samples subjected to acid precipitation were assayed. Each biotherapeutic sample was incubated in 20 mM sodium deoxycholate or 20 mM sodium lauroyl sarcosinate for 5 minutes, 15 minutes, 30 minutes, 60 minutes or 120 minutes prior to acid precipitation. FIG. 31 shows that acid precipitation depleted protein in biotherapeutic samples more effectively the longer that samples were incubated in 20 mM sodium deoxycholate or 20 mM sodium lauroyl sarcosinate, especially for incubation times up to about 60 minutes, which depleted more than 99.5% of protein.

Figure 32A:
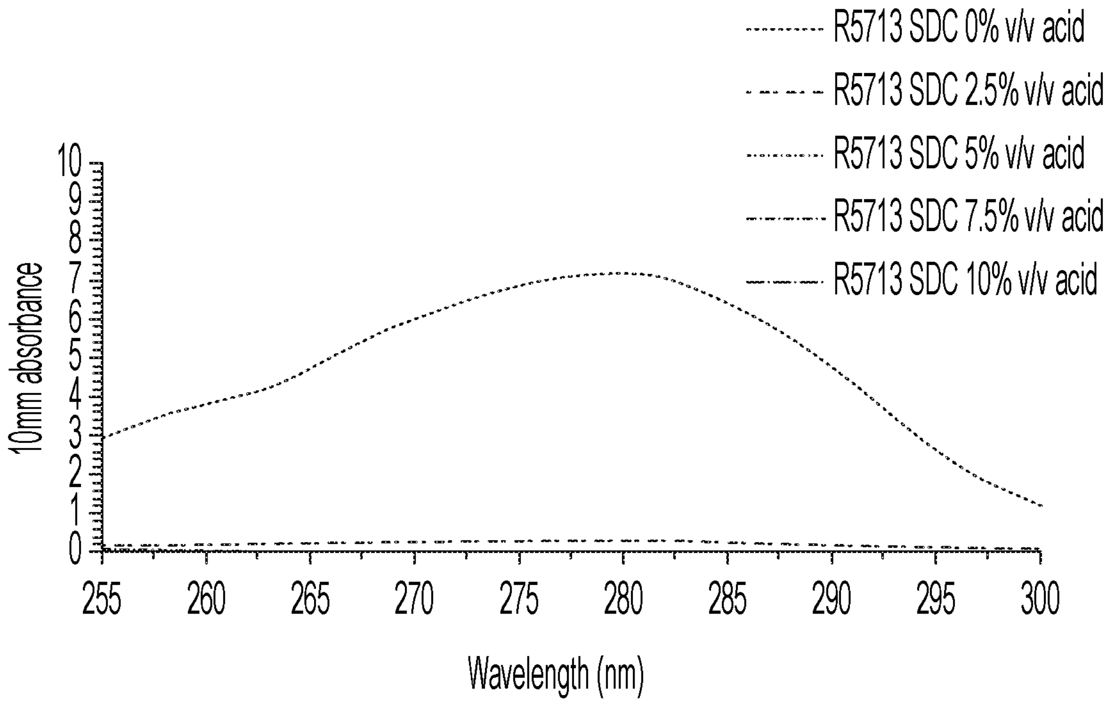
FIG. 32A shows the protein spectra of biotherapeutic samples at 280 nm after incubation in 20 mM sodium deoxycholate and 0%, 2.5%, 5%, 7.5% or 10% (v/v) 10% trifluoroacetic acid, according to an exemplary embodiment.
Figure 32B:
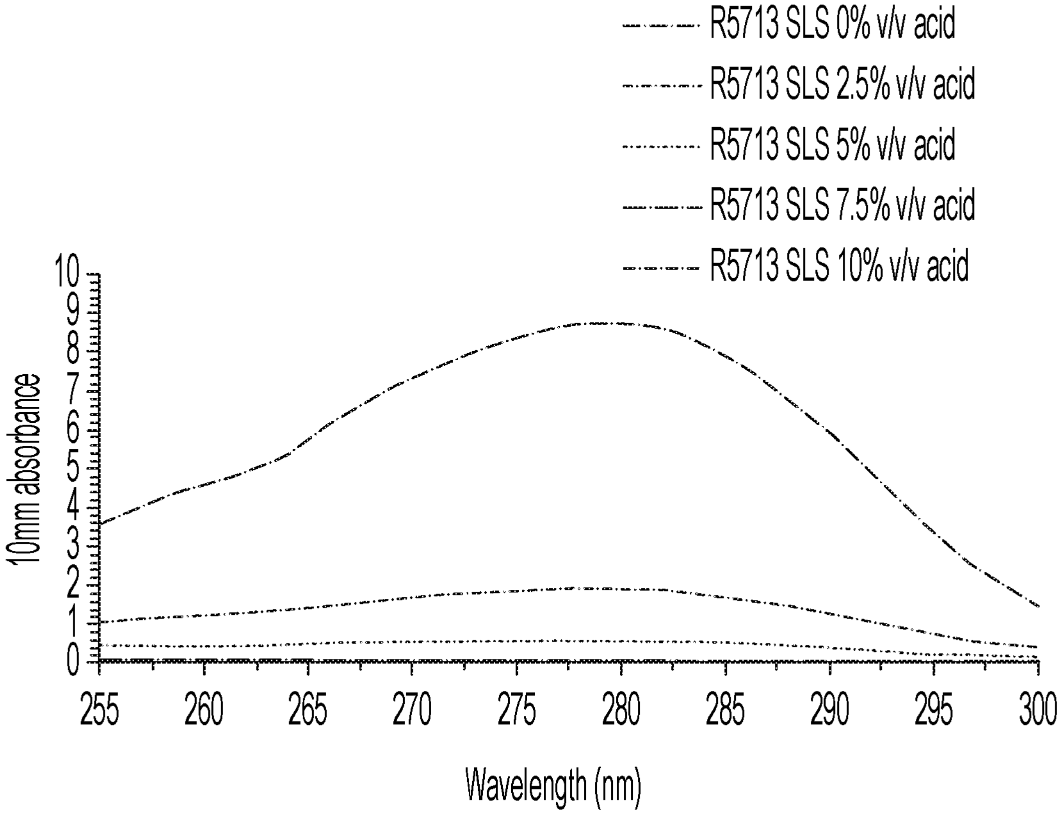
FIG. 32B shows the protein spectra of biotherapeutic samples at 280 nm after incubation in 20 mM sodium lauroyl sarcosinate and 0%, 2.5%, 5%, 7.5% or 10% (v/v) 10% trifluoroacetic acid, according to an exemplary embodiment.
Figure 32C:
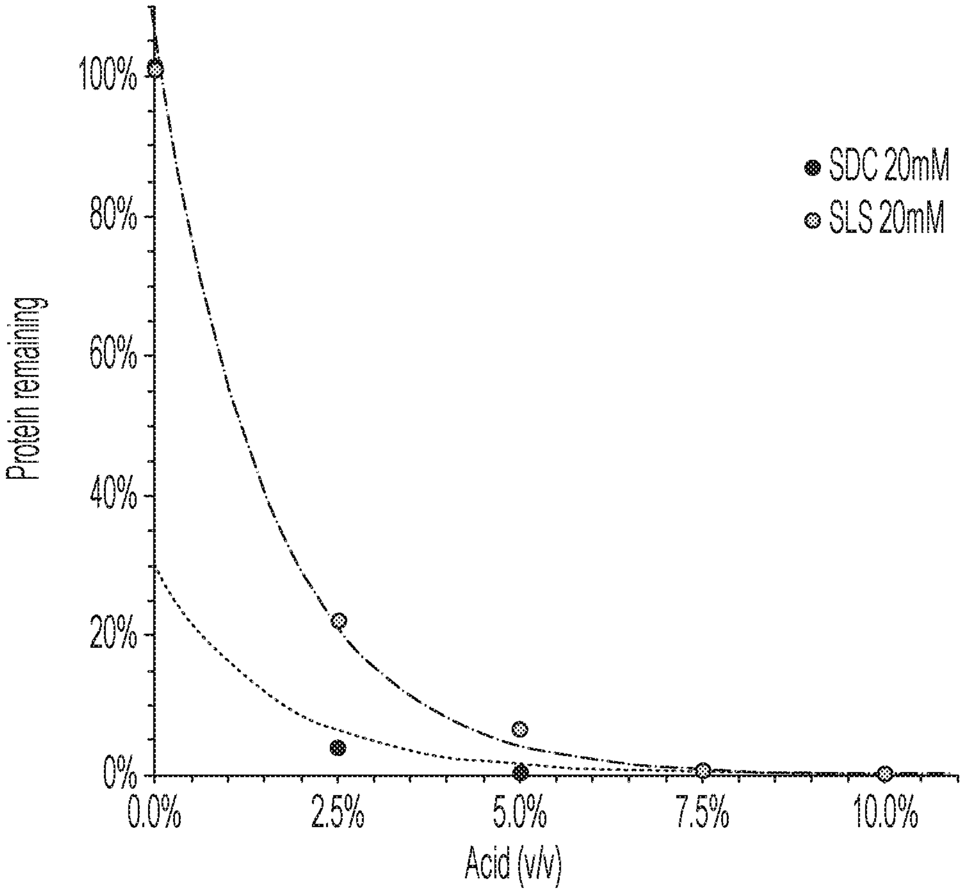
FIG. 32C shows the percentage of protein remaining in biotherapeutic samples after incubation in 20 mM sodium deoxycholate or 20 mM sodium lauroyl sarcosinate and 0%, 2.5%, 5%, 7.5% or 10% (v/v) 10% trifluoroacetic acid, according to an exemplary embodiment.

The effect acid precipitation pH has on protein depletion in biotherapeutic samples was investigated. Each biotherapeutic sample was incubated in 20 mM sodium deoxycholate or 20 mM sodium lauroyl sarcosinate and 0%, 2.5%, 5%, 7.5% or 10% (v/v) 10% trifluoroacetic acid. FIG. 32 shows that lowering acid precipitation pH using a higher percentage (v/v) of 10% trifluoroacetic acid depleted protein more effectively, especially for percentages (v/v) of 10% trifluoroacetic acid up to about 7.5%, and that using more than 7.5% (v/v) 10% trifluoroacetic acid for precipitation depleted more than 99.5% of protein.

Figure 33A:
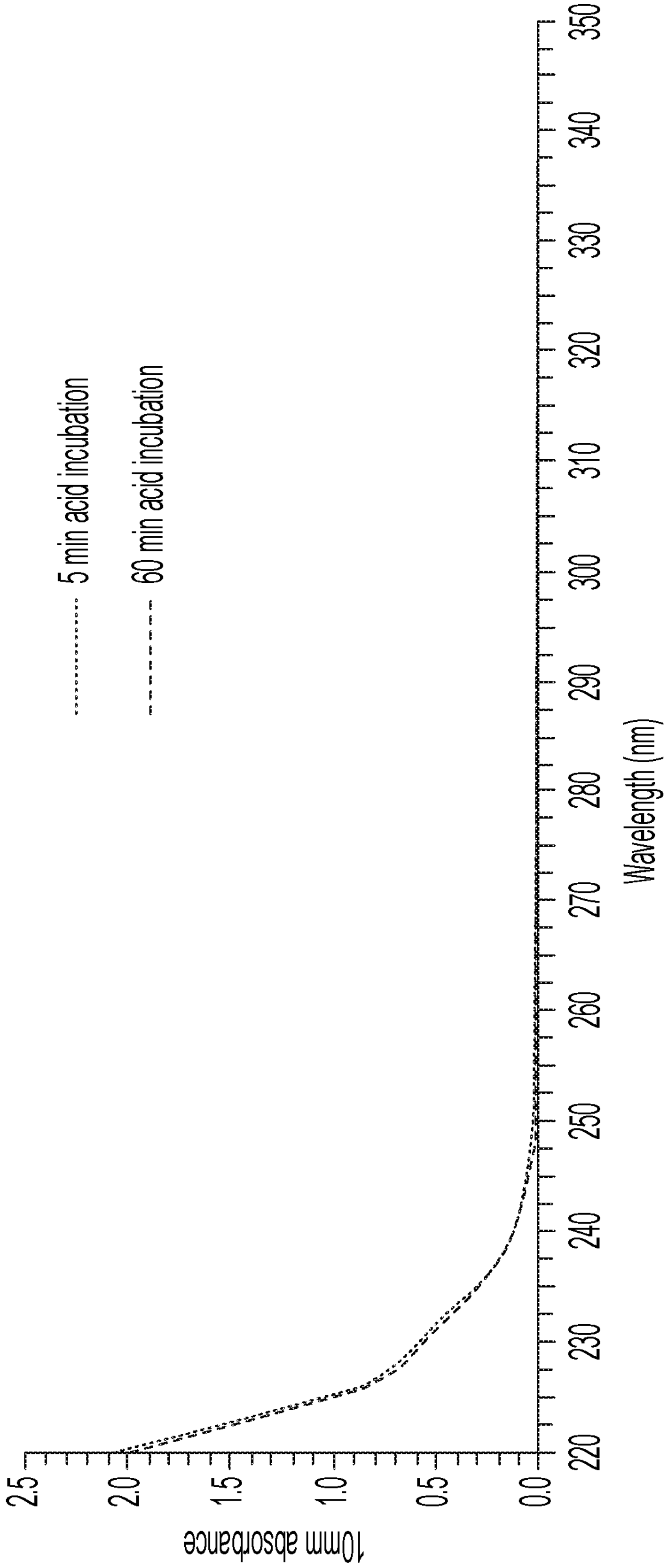
FIG. 33A shows the protein spectra of biotherapeutic samples at 280 nm after acid precipitation for 5 minutes or 60 minutes, according to an exemplary embodiment.
Figure 33B:
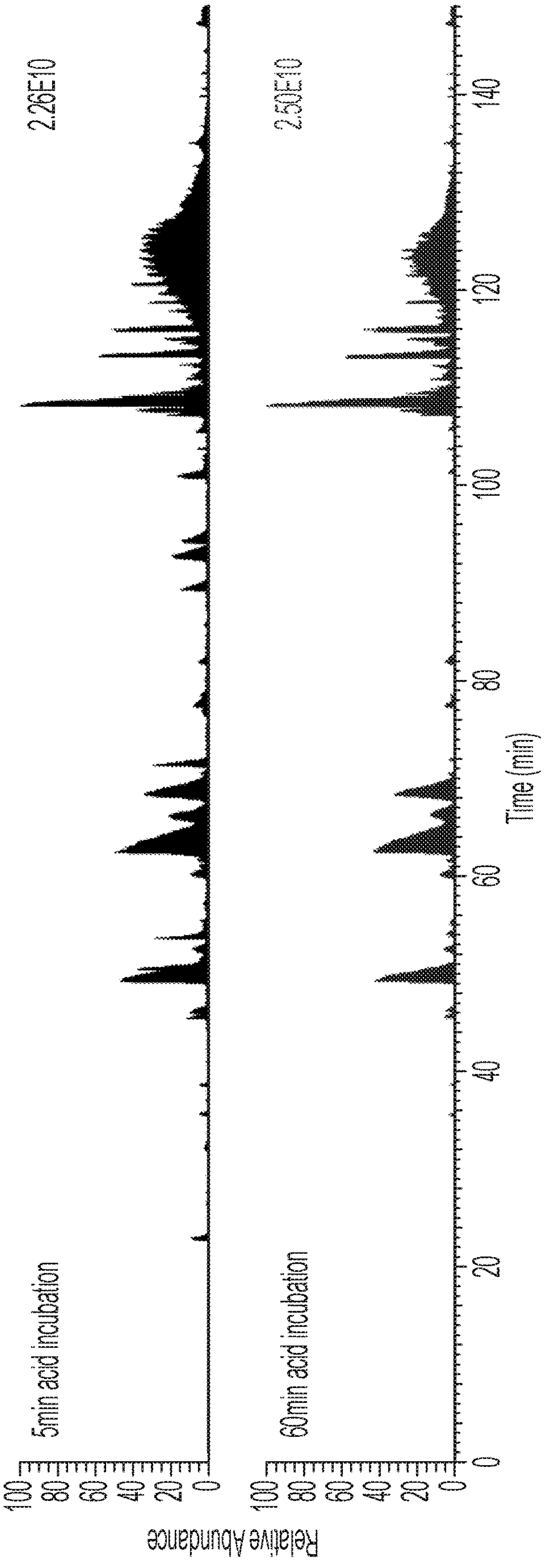
FIG. 33B shows the total ion chromatogram of biotherapeutic samples obtained using nano liquid chromatography-mass spectrometry after acid precipitation for 5 minutes or 60 minutes, according to an exemplary embodiment.
Figure 33C:
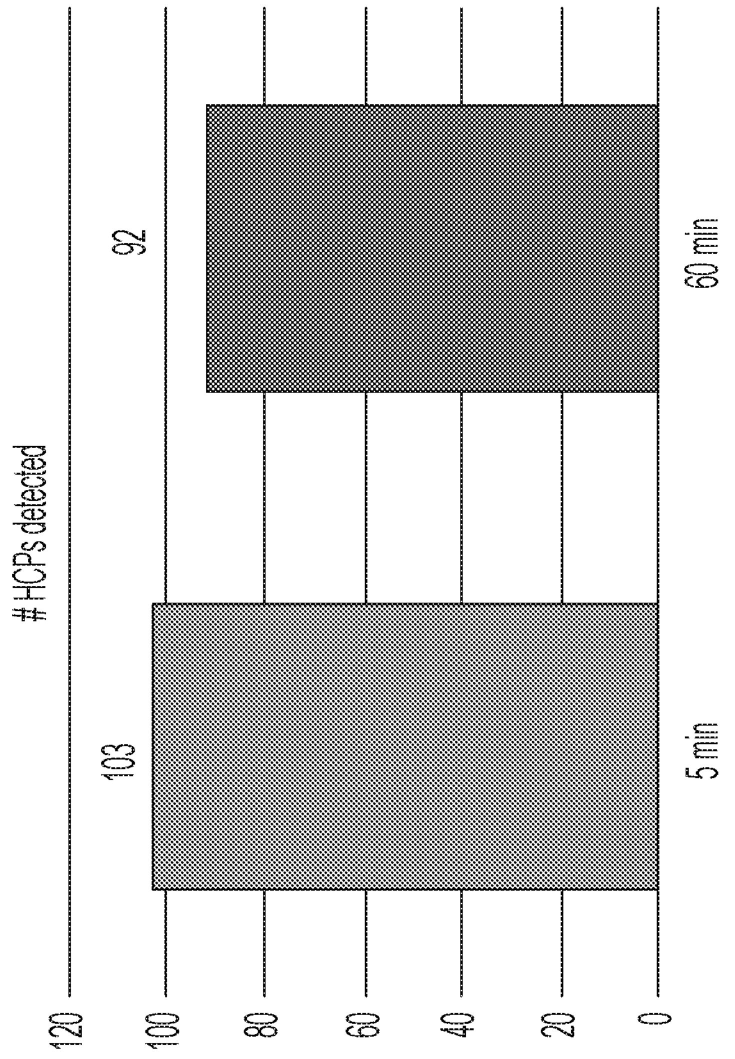
FIG. 33C shows the number of HCPs identified in biotherapeutic samples using nano liquid chromatography-mass spectrometry and Protein Metrics Byonic after acid precipitation for 5 minutes or 10 minutes, according to an exemplary embodiment.

The effect that acid incubation time has on protein depletion in biotherapeutic protein samples was assessed. Each biotherapeutic sample was incubated in acid for 5 minutes or 60 minutes. FIG. 33A and FIG. 33B show that incubating biotherapeutic samples in acid longer than 5 minutes did not deplete protein in samples more effectively. Furthermore, FIG. 33C shows that incubating biotherapeutic samples in acid longer than 5 minutes did not enable identification of more HCPs.

Figure 34A:
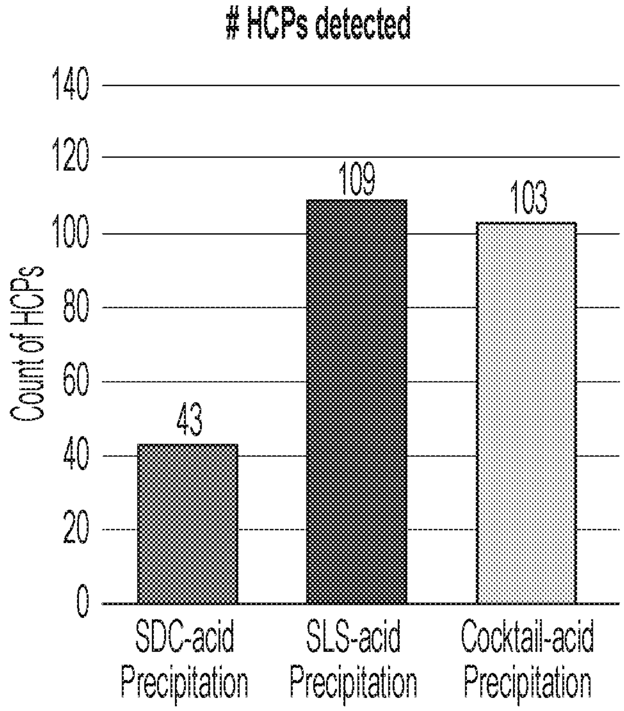
FIG. 34A shows the number of HCPs identified in biotherapeutic samples using nano liquid chromatography-mass spectrometry and Protein Metrics Byonic after incubation in 40 mM sodium deoxycholate, 40 mM sodium lauroyl sarcosinate or both 20 mM sodium deoxycholate and 20 mM sodium lauroyl sarcosinate and acid precipitation, according to an exemplary embodiment.
Figure 34B:
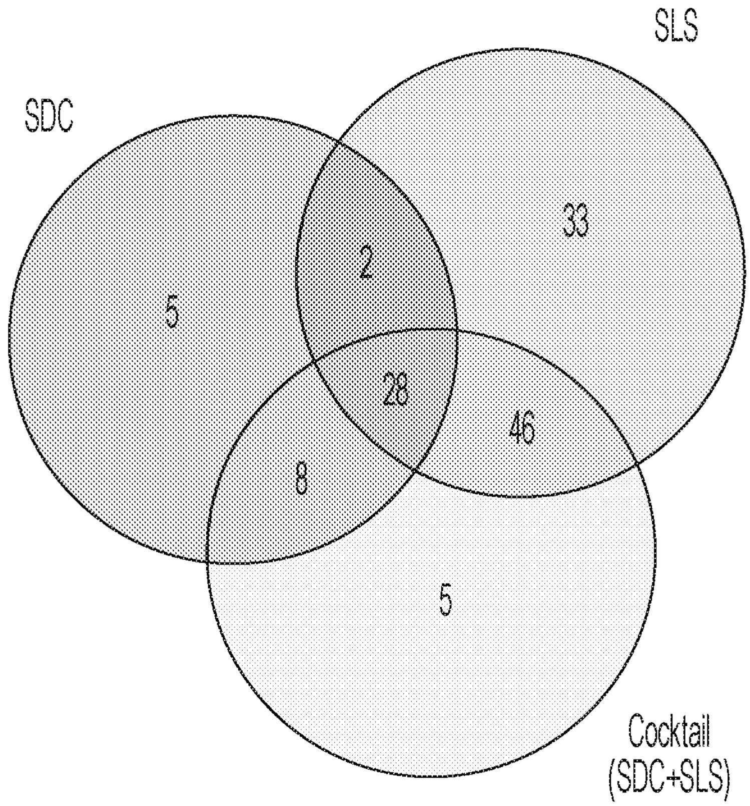
FIG. 34B shows a Venn diagram and number of HCPs identified in biotherapeutic samples using nano liquid chromatography-mass spectrometry and Protein Metrics Byonic after incubation in 40 mM sodium deoxycholate, 40 mM sodium lauroyl sarcosinate or both 20 mM sodium deoxycholate and 20 mM sodium lauroyl sarcosinate and acid precipitation, according to an exemplary embodiment.
Figure 35A:
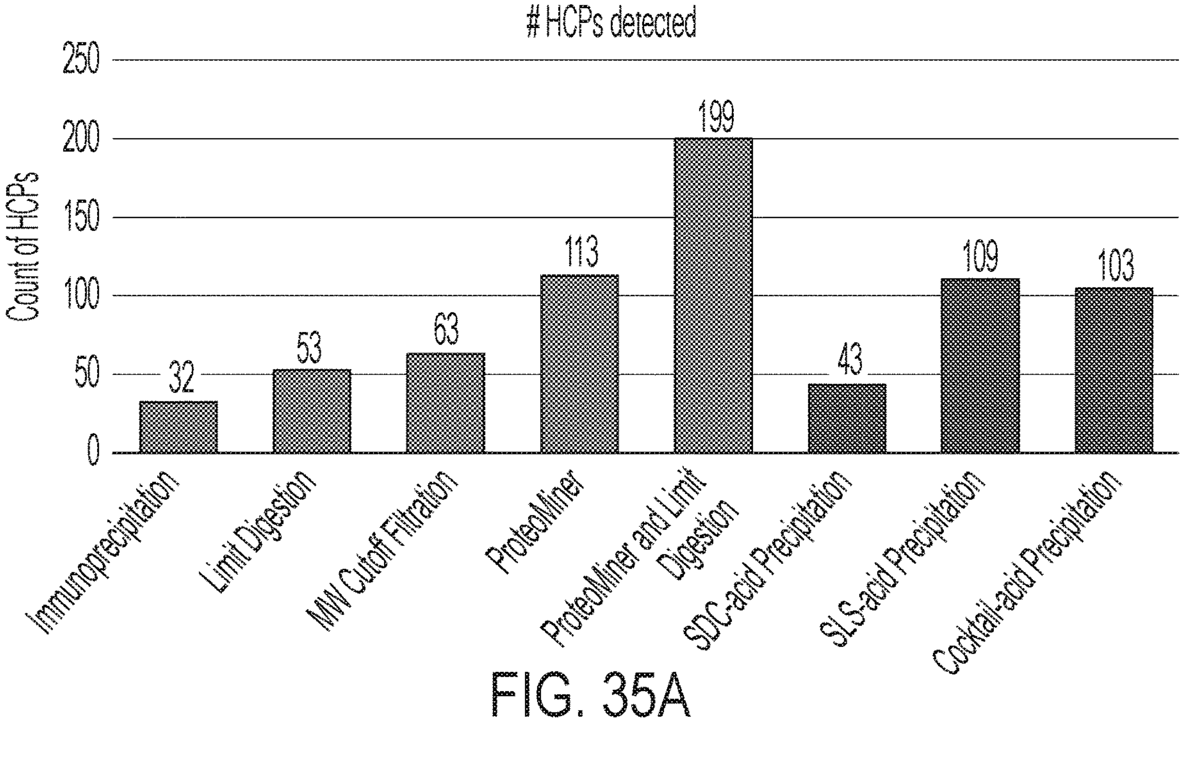
FIG. 35A shows the number of HCPs identified in samples of a biotherapeutic using nano liquid chromatography-mass spectrometry and Protein Metrics Byonic after incubation in 40 mM sodium deoxycholate, 40 mM sodium lauroyl sarcosinate or both 20 mM sodium deoxycholate and 20 mM sodium lauroyl sarcosinate and acid precipitation, or existing methods, according to an exemplary embodiment.
Figure 35B:
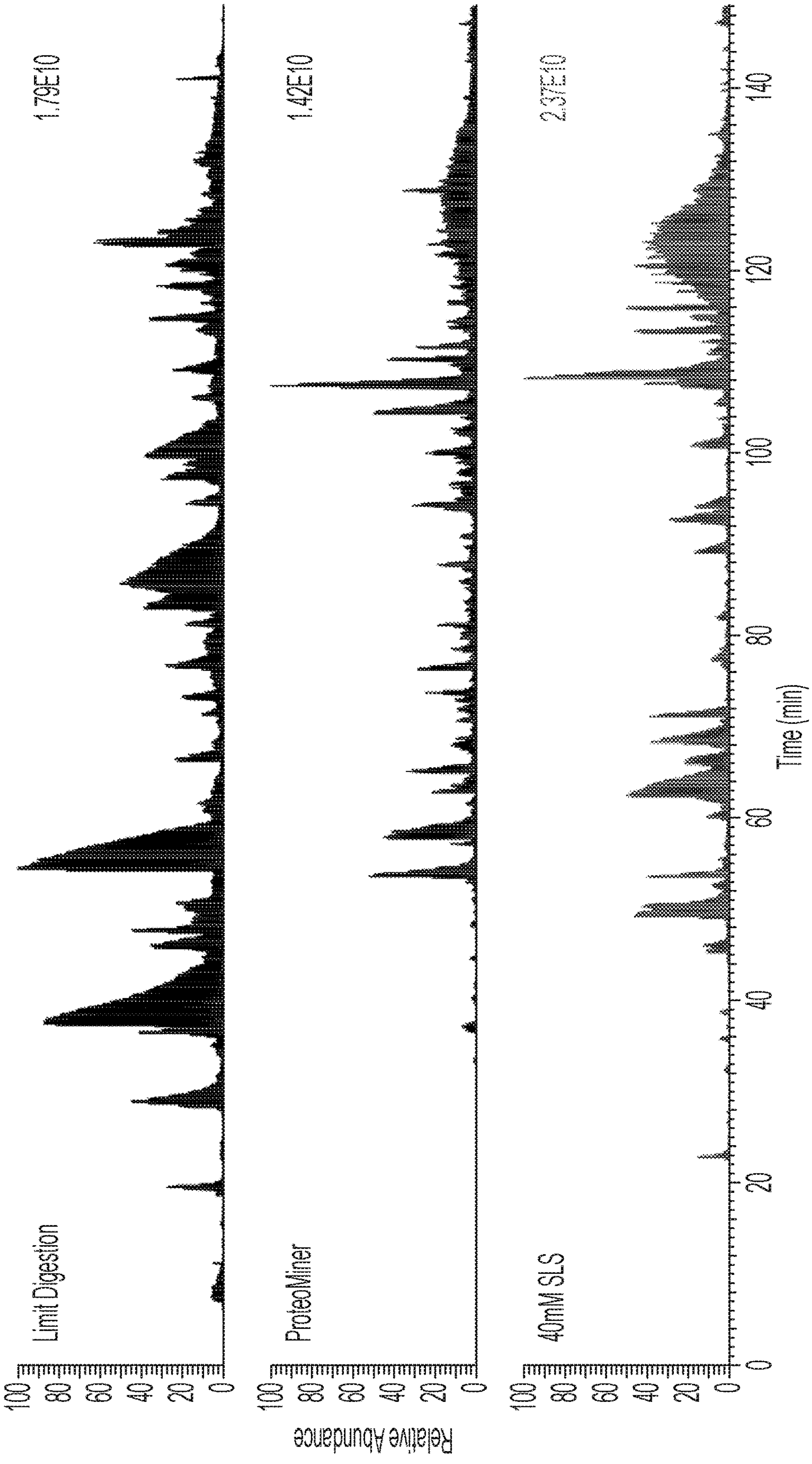
FIG. 35B shows the total ion chromatograms of samples of a biotherapeutic obtained using nano liquid chromatography-mass spectrometry and Protein Metrics Byonic after incubation in 40 mM sodium lauroyl sarcosinate and acid precipitation, or a limited digestion, molecular weight cutoff filtration or ProteoMiner method, according to an exemplary embodiment.
Figure 35C:
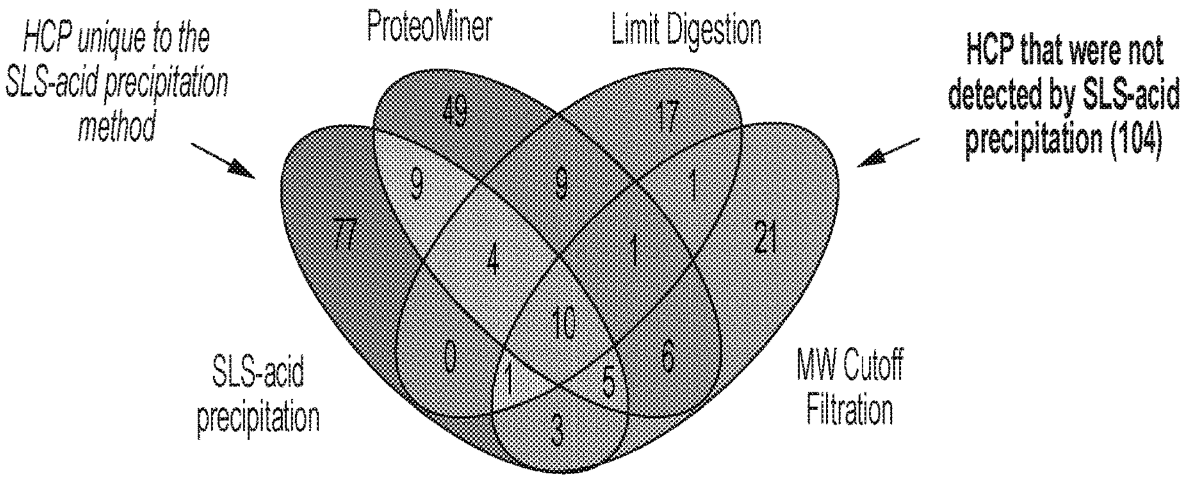
FIG. 35C shows a Venn diagram and number of HCPs identified in samples of a biotherapeutic using nano liquid chromatography-mass spectrometry and Protein Metrics Byonic after incubation in 40 mM sodium lauroyl sarcosinate and acid precipitation, or a limited digestion, molecular weight cutoff filtration or ProteoMiner method, according to an exemplary embodiment.

The effects that incubating biotherapeutic samples in sodium deoxycholate and sodium lauroyl sarcosinate has on HCP identification using the surfactant-assisted acid precipitation method were assayed. Each biotherapeutic sample was incubated in 40 mM sodium deoxycholate, 40 mM sodium lauroyl sarcosinate, or both 20 mM sodium deoxycholate and 20 mM sodium lauroyl sarcosinate and subjected to acid precipitation before HCP identification using nano liquid chromatography-mass spectrometry and Protein Metrics Byonic. FIG. 34 shows that the surfactant-assisted acid precipitation method identified 109, 103 and 43 HCPs in biotherapeutic samples that were incubated in 40 mM sodium lauroyl sarcosinate, both 20 mM sodium deoxycholate and 20 mM sodium deoxycholate, and 40 mM sodium deoxycholate, respectively. These data demonstrate that incubating a biotherapeutic sample in sodium lauroyl sarcosinate enabled identification of the most HCPs using the surfactant-assisted acid precipitation method, followed by incubating biotherapeutic samples in both sodium deoxycholate and sodium lauroyl sarcosinate, and sodium deoxycholate, respectively. In comparison, FIG. 35 shows that ProteoMiner with limited digestion, ProteoMiner, molecular weight cutoff filtration, limited digestion and immunoprecipitation methods identified 199, 113, 63, 53 and 32 HCPs in samples of the same biotherapeutic, respectively, 104 of which weren't identified using the surfactant-assisted acid precipitation method following incubation in 40 mM sodium lauroyl sarcosinate. These data suggest that the HCPs identified using the surfactant-assisted acid precipitation method following incubation in sodium lauroyl sarcosinate may have unique properties that precluded detection using other methods.

Figure 36A:
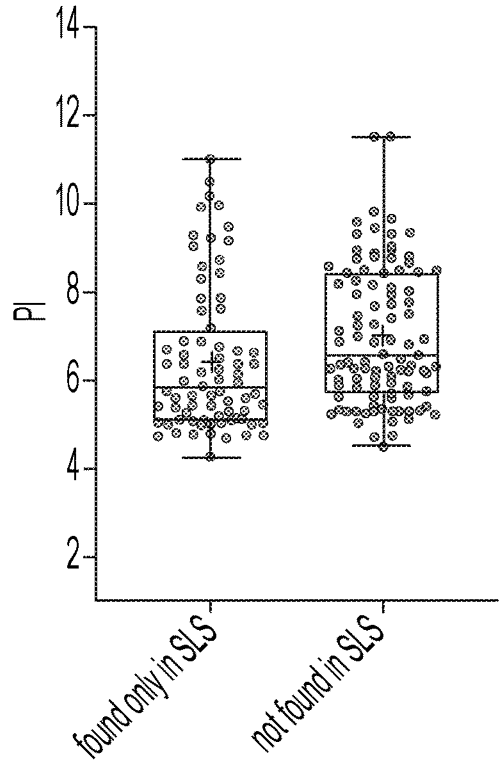
FIG. 36A shows distributions of the isoelectric point of HCPs that were only identified using nano liquid chromatography-mass spectrometry and Protein Metrics Byonic after incubation in 40 mM sodium lauroyl sarcosinate and acid precipitation, or limited digestion, molecular weight cutoff filtration and ProteoMiner methods, according to an exemplary embodiment.
Figure 36B:
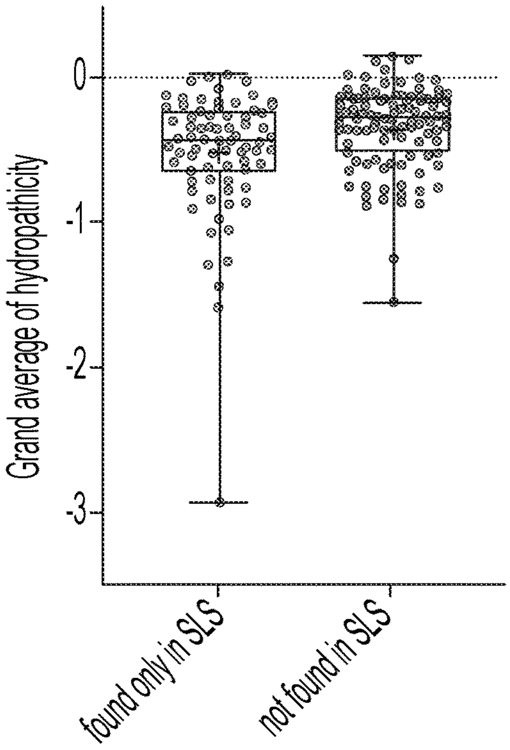
FIG. 36B shows distributions of the hydropathicity of HCPs that were only identified using nano liquid chromatography-mass spectrometry and Protein Metrics Byonic after incubation in 40 mM sodium lauroyl sarcosinate and acid precipitation, or limited digestion, molecular weight cutoff filtration and ProteoMiner methods, according to an exemplary embodiment.
Figure 37A:
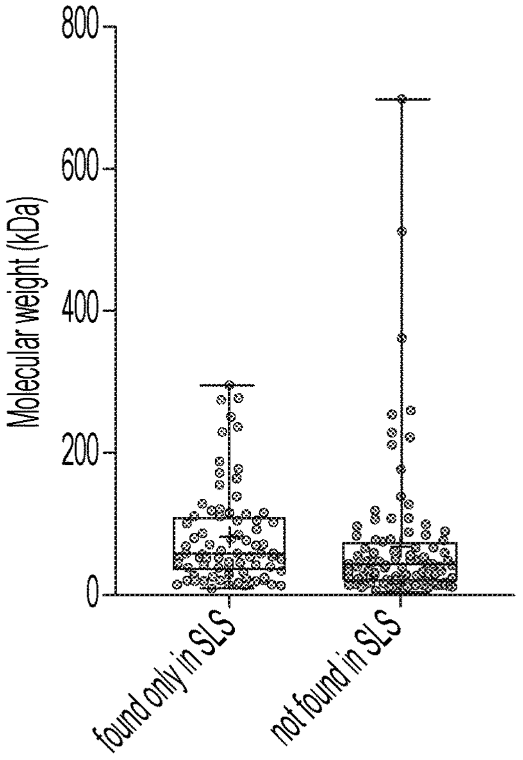
FIG. 37A shows distributions of the molecular weight of HCPs that were only identified using nano liquid chromatography-mass spectrometry and Protein Metrics Byonic after incubation in 40 mM sodium lauroyl sarcosinate and acid precipitation, or limited digestion, molecular weight cutoff filtration and ProteoMiner methods, according to an exemplary embodiment.
Figure 37B:
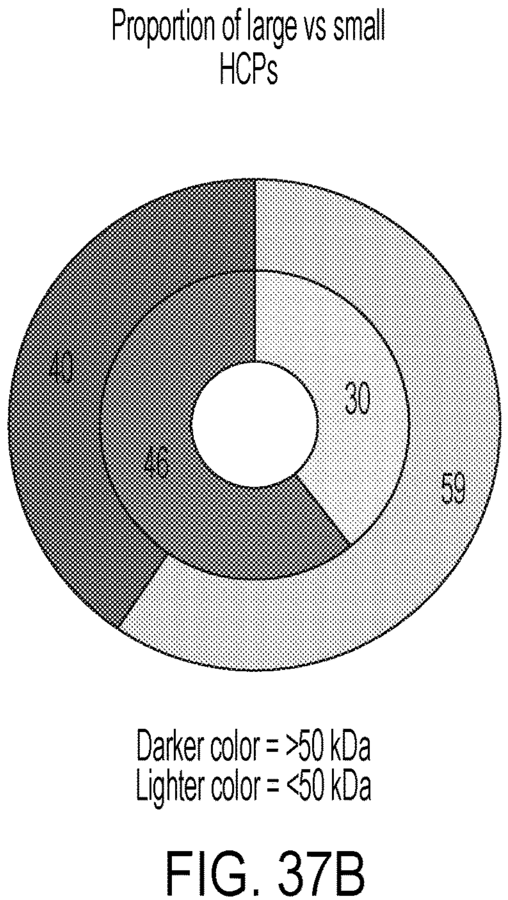
FIG. 37B shows the number of HCPs greater than 50 kDa (dark) and less than 50 kDa (light) that were only identified using nano liquid chromatography-mass spectrometry and Protein Metrics Byonic after incubation in 40 mM sodium lauroyl sarcosinate and acid precipitation (outer circle) or limited digestion, molecular weight cutoff filtration and ProteoMiner methods (inner circle), according to an exemplary embodiment.
Figure 38A:
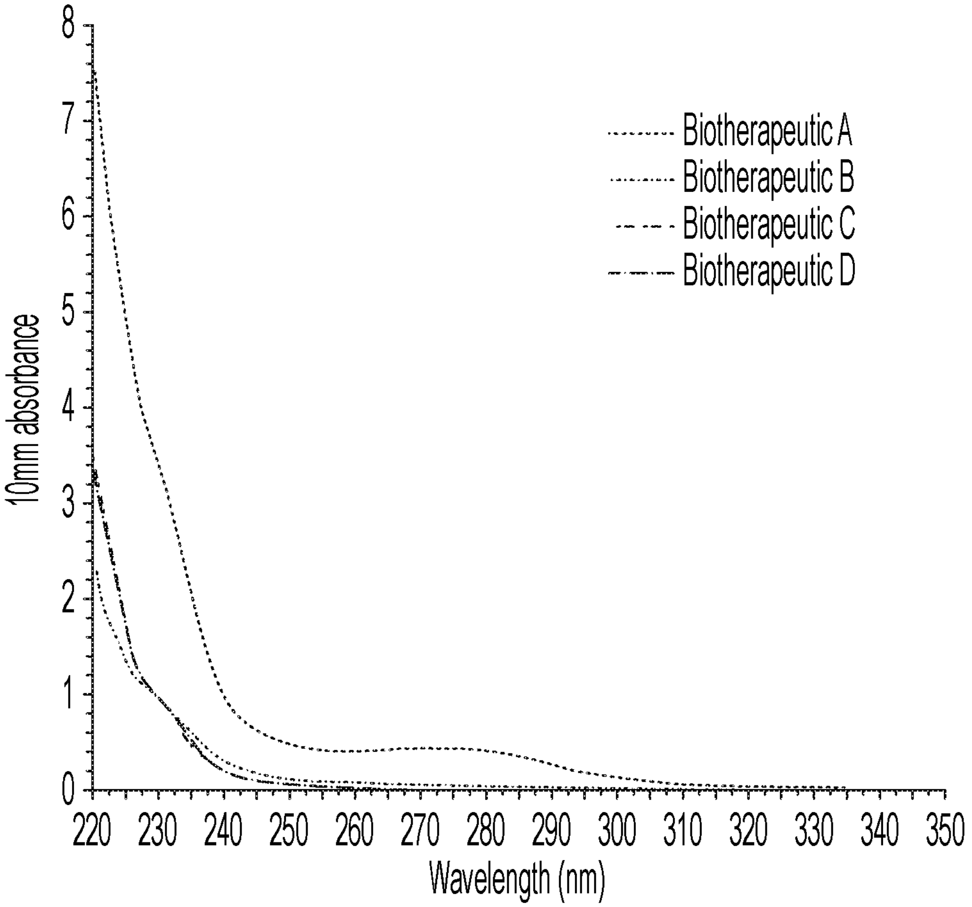
FIG. 38A shows the protein spectra of samples of four different biotherapeutic proteins at 280 nm after surfactant-assisted dissociation using 40 mM sodium lauroyl sarcosinate and acid precipitation, according to an exemplary embodiment.
Figure 38B:
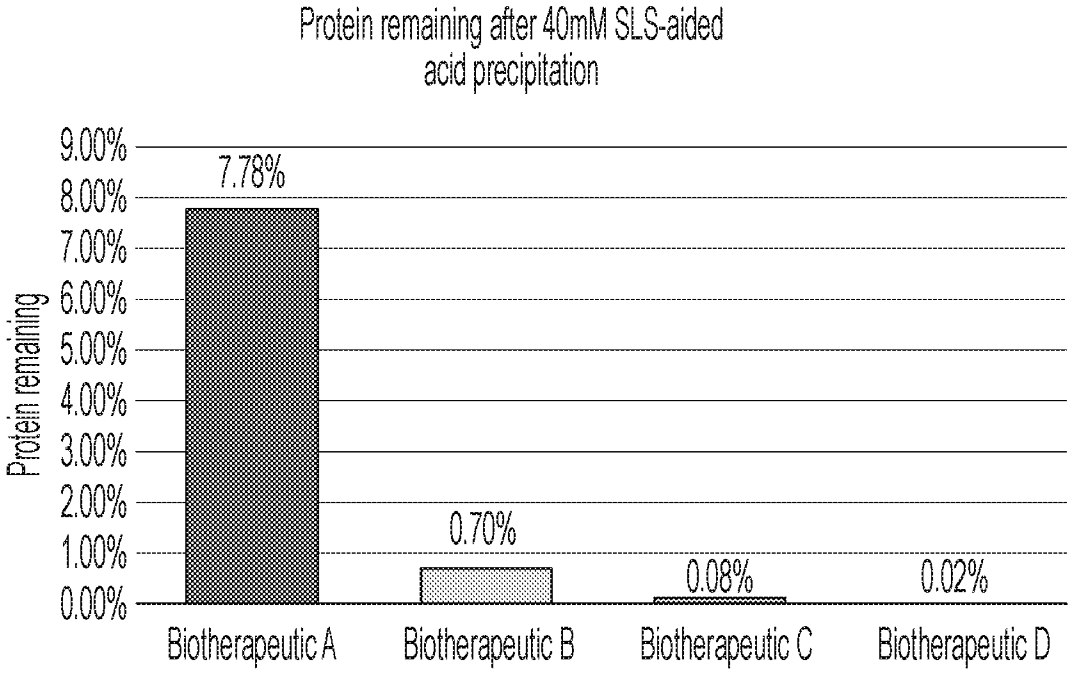
FIG. 38B shows the percentage of protein remaining in samples of four different biotherapeutic proteins after surfactant-assisted dissociation using 40 mM sodium lauroyl sarcosinate and acid precipitation, according to an exemplary embodiment.

The HCPs identified using the surfactant-assisted acid precipitation method following incubation in 40 mM sodium lauroyl sarcosinate were characterized. FIG. 36 shows that the HCPs identified using the surfactant-assisted acid precipitation method following incubation in 40 mM sodium lauroyl sarcosinate were generally more acidic and hydrophilic than the HCPs identified using the limited digestion, molecular weight cutoff filtration and ProteoMiner methods. Additionally, FIG. 37 shows that the HCPs identified using the surfactant-assisted acid precipitation method following incubation in 40 mM sodium lauroyl sarcosinate were generally larger (e.g., greater than 50 kDa) than the host cell proteins identified using the limited digestion, molecular weight cutoff filtration and ProteoMiner methods. These data suggest that characteristics of the HCPs identified using the surfactant-assisted acid precipitation method following incubation in 40 mM sodium lauroyl sarcosinate may affect their detection or depletion using other HCP identification methods. For example, FIG. 38 shows that incubating samples of four different biotherapeutics in 40 mM sodium lauroyl sarcosinate and acid precipitation depleted 92.22%, 99.3%, 99.92% and 99.98% of protein. These data suggest that that the efficacy of protein depletion in a biotherapeutic sample using 40 mM sodium lauroyl sarcosinate and acid precipitation is dependent on the physiochemical properties of the biotherapeutic, and the efficacy of protein depletion can affect the detection of HCPs.

Example 7. HCP Profiling in Enriched HMW Fractions

In order to further characterize HCP contaminants in recombinant protein samples, for example monoclonal antibody drug substance, novel methods were developed for identifying, characterizing, and removing HCPs from enriched HMW fractions of drug substance. This Example sets forth a workflow for the exemplary methods taught in the subsequent Examples.

Materials. Monoclonal antibody DS and enriched HMW were produced internally. A 10 KDa filter was purchased from Pall (New York, N.Y.), and 3K Amicon ultracentrifugal filters were obtained from MilliporeSigma (Burlington, Mass.). Dithiothreitol (DTT) and iodoacetamide (IAM) were purchased from Thermo Scientific (Rockford, Ill.). Sequencing grade modified trypsin was obtained from Promega (Madison, Wis.). Tris-HCl buffer (pH 7.5) was purchased from Invitrogen (Carlsbad, Calif.). Urea and acetic acid were purchased from Sigma-Aldrich (St. Louis, Mo.). PNGase F was purchased from New England Biolabs (Ipswich, Mass.). LC-MS grade 0.1% formic acid in water and 0.1% formic acid in acetonitrile were from Honeywell (Charlotte, N.C.).

Tryptic digestion of DS and enriched HMW species. The enriched HMW species were generated in house through preparative SEC of DS. HCP analyses of mAbs and enriched HMW fractions were performed using a native digestion approach similar to a previously published method (Huang et al.) with optimized enzyme to substance ratio and spiked recombinant protein internal standards. Briefly, all of the samples were buffer exchanged into the water using a 3 KDa centrifugal filter. The concentration of each sample was measured by nanodrop after buffer exchange. Subsequently, 2 mg of each sample was spiked with two internal protein standards, recombinant human IL33 and heavy isotope-labeled CHO putative phospholipase B-like 2 (PLBD2) at a known concentration. Samples were then digested with trypsin (1:1000 w/w enzyme:substrate ratio) at 37° C. overnight. After digestion, disulfide bonds were reduced by adding 2 μL of 25 mg/mL DTT and incubated at 90° C. for 20 minutes. The reduced samples were further alkylated by adding 2 μL of 0.25 M IAM for 30 min in dark at room temperature. The final digest was filtered with a 10 KDa MW molecular weight cutoff filter. Flow-through was acidified with 5 μL of 10% formic acid and collected for analysis.

Fraction collection. Enriched dimer, monomer and low molecular weight fractions were prepared through SEC from the DS. PNGase F was added to 100 μg of DS samples for deglycosylation (1:5 w/w enzyme to protein ratio) for 1 hour. Proteins were separated and collected on a Waters ACQUITY UPLC system equipped with an ACQUITY UPLC protein BEH SEC column (200 Å, 1.7 μm, 4.6 mm×300 mm), operated with isocratic flow at 0.2 mL/min with a mobile phase of 150 mM ammonium acetate. The UV detector was set at a 280 nm wavelength.

Tryptic digestion of fractionated samples. Each collected fraction was spiked with 0.01 μg of heavy isotope-labeled PLBD2 as an internal standard. All samples were dried with a SpeedVac instrument, then reconstituted in 20 μL of denaturing buffer composed of 0.1 M Tris-HCl, pH 7.5, 8 M urea, and 10 mM DTT. Samples were denatured and reduced at 56° C. for 30 minutes, then alkylated with 50 mM IAM for 30 minutes in the dark at room temperature. Subsequently, samples were digested with 100 μL of 20 ng/μL trypsin and incubated at 37° C. overnight. The digestion was quenched by adding 5 μL acetic acid.

LC-MS/MS analysis. The digested samples were analyzed with a Waters ACQUITY UPLC system coupled with a Thermo Scientific Q Exactive Plus Mass spectrometer. The UPLC system was equipped with a Waters CSH C18 column (1.7 μm particle size, 2.1 mm×150 mm). Mobile phase A was 0.1% formic acid in water, and mobile phase B was 0.1% formic acid in acetonitrile. The flow rate was 0.25 mL/min, and the linear LC gradient was set as follows: 0.1% B at 0-5 min, 32% B at 85 min, 40% B at 90 min, 90% B at 95-105 min, and 0.1% B at 106-125 min. The mass spectrum data acquisition was performed with the top ten DDA method. The MS1 scan range was 300-1500 m/z at 70 k resolution (m/z 400). The MS/MS isolation window was set to 3 m/z, and normal collision energy (NCE) was set to 28. The minimum automatic gain control (AGC) was set to 5e4 with a maximum IT of 300 ms.

The directly digested samples were analyzed with an UltiMate 3000 RSLCnano system (Thermo Scientific) coupled to a Q-Exactive HFX mass spectrometer (Thermo Scientific). The RSLCnano system was equipped with an Acclaim PepMap 100 75 μm×2 cm trap column and an Acclaim PepMap 75 μm×25 cm C18 analytical column. Mobile phase A was 0.1% formic acid in water, and mobile phase B was 0.1% formic acid in 80% acetonitrile. The flow rate was 300 nL/min, and the linear LC gradient was set as follows: 3% B at 0-5 min, 25% B at 40 min, 37% B at 48 min, 95% B at 53-58 min, and 3% B at 58-60 min. Each sample was analyzed with a full mass scan followed by parallel reaction monitoring (PRM) mode. One full mass scan was set at a resolution of 120 k, with an AGC target of 1e6, maximum IT of 60 ms, and scan range of 350-2000 m/z. PRM was set with an isolation window of 3 m/z, at a resolution of 30K, NCE was set to 27, the AGC was 2e5, and the maximum IT was 150 ms.

Data analysis. The raw files were searched against the Uniprot *Cricetulus griseus* proteome database using SEQUEST and Mascot (Matrix Science) through Proteome Discoverer 2.2 (Thermo Scientific). Precursor mass tolerance was set to 10 ppm and fragment ion mass tolerance was set to 0.02 Da. Trypsin was set as the digestion enzyme. Methionine oxidation was set as dynamic modification and cysteine alkylation was set as the static modification. Proteins with a minimum of two unique peptides detected and peptide length >6 amino acids with high-quality MS/MS spectra were filtered as true positives. Skyline was used for peak integration and further analysis.

For native digest samples, heavy isotope-labeled PLBD2 was used as a qualitative control to verify the digestion efficiency and HCP signal intensity. The relative abundance of each identified protein was quantified by averaging the peak area of the top two to three peptides for each host cell protein, divided by the average abundance from the top three peptides of recombinant human IL33, with the internal standard spiked in at 50 ppm (micromoles standard to moles of antibody). All results were calculated in mole ratio ppm.

For samples analyzed by PRM, the relative abundance of each protein was quantified by averaging the product ion area of peptides for each host cell protein divided by the average abundance of the top three peptides of heavy isotope-labeled PLBD2, with the internal standard spiked in at 0.01 μg for each sample. The results were calculated in fmol.

Experimental design. HCP analysis was performed on five in-house generated mAbs and their enriched HMW species. The DS and enriched HMW species were subjected to buffer exchange, and the concentration was determined prior to the sample analysis. The sample preparation was performed using the optimized native digestion method introduced by Huang in 2017. The native digestion method has been adopted in many HCP workflows in the industry because of its simplicity and effectiveness in decreasing the dynamic range of analytes. Briefly, a small amount of trypsin was added to the sample without a denaturing step. Antibodies were minimally digested under native conditions, whereas HCPs were preferentially digested. After digestion, the samples were denatured in a heating step, and the undigested antibodies were removed by precipitation. The HCP peptides were injected into the LC-MS/MS instrument for analysis with minimal matrix interference. The ratios of the top three most abundant peptides from HCPs to the spiked standards were used to calculate the levels of HCPs in mole ratio ppm (micromoles of HCP to moles of antibody). The reporting of molar ratio between HCP and antibody enables a fair comparison by taking into consideration the wide molecular weight distribution of HCPs present in the samples.

Example 8. HCP Profiling of DS and Enriched HMW Species from Five mAbs

Figure 39:
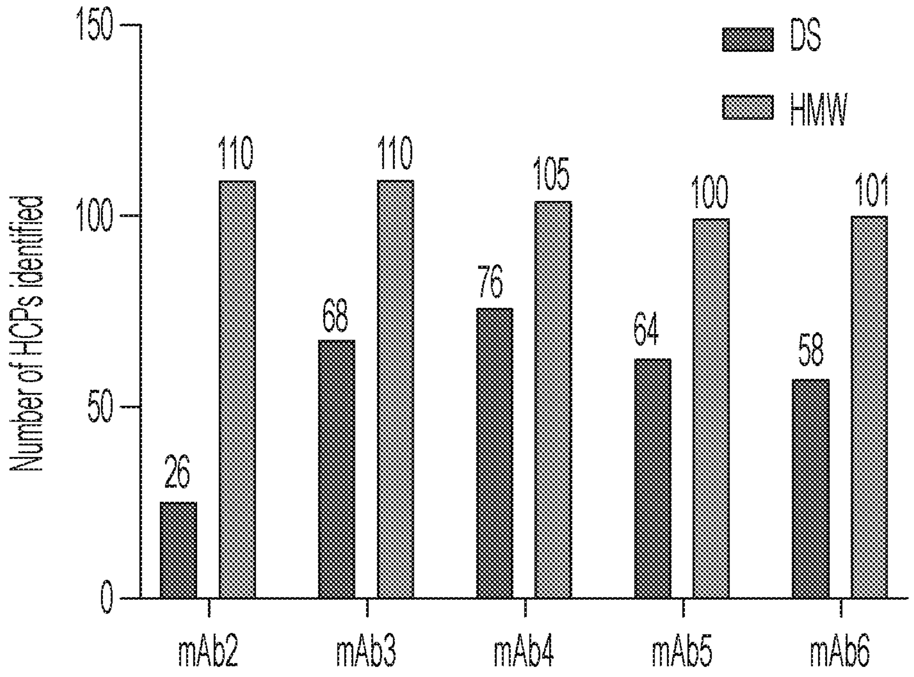
FIG. 39 shows a number of HCPs identified in DS and enriched HMW samples from various mAbs, according to an exemplary embodiment.

The number of HCPs (>0.1 ppm) identified across all samples using the workflow described in Example 7 is shown in FIG. 39. For each mAb, the blue bar on the left represents the number of HCPs identified from DS, and the red bar on the right represents the number of HCPs identified from enriched HMW. More HCPs were detected from enriched HMW than DS for all five mAbs. A total of 110, 110, 105, 100, and 101 HCPs were identified in the enriched HMW fractions from mAb2 to mAb6, respectively. In contrast, only 26, 68, 76, 64, and 58 HCPs were identified from mAb2 to mAb6 DS. The total identified HCPs from HMW varied across the samples, indicating the molecule dependence of HCP enrichment in HMW. Notably, for mAb2, the number of HCPs identified was four times greater in enriched HMW than DS.

Twenty-five frequently identified HCPs and the estimated amounts in mole ratio ppm are listed in FIG. 40. The HCPs are listed in order of abundance in HMW species of mAb2. The heatmap is colored by HCP abundance, ranging from 0 ppm (blue, not detected) to more than 100 ppm (red).

Most of the commonly identified HCPs were preferentially enriched in HMW for all five mAbs. For example, C-C motif chemokine was a dominant HCP, at 37.4 ppm in mAb2, and was identified at a higher abundance in enriched HMW than DS across all five mAbs. HMW of mAb2 exhibited a markedly higher C-C motif chemokine level (1738.5 ppm) than that in other mAb HMW fractions (20.9-61.6 ppm). Metalloproteinase inhibitor 1 (TIMP1), a frequently identified HCP from different processing steps (Singh et al., 2020, *Biotechnology Prog,* 36(2):e2936; Park et al., 2017, *Sci Rep,* 10(7):44246), had a level of 0.2 ppm in mAb2 DS and 11.4 ppm in mAb4 DS. In enriched HMW, the abundance of TIMP1 was 3-13 times higher than that in DS. Beta-hexosaminidase, which has been reported to be associated with N-glycan degradation when present at levels of several hundred ppm (Li et al., 2021, *Biotechnol Prog,* 37(3):e3128), was not detected in most of the mAb DS samples but had elevated levels in enriched HMW. Examples of other frequently identified HCPs include Cornifin-A, Peroxiredoxin, and Complement C1r-A subcomponent, which had higher abundance in enriched HMW than DS.

Lipases are a group of problematic host cell proteins that may degrade polysorbate, thus inducing the formation of aggregates and affecting the shelf life of drug products (Chiu et al.; McShan et al.; Zhang et al. 2020; Zhang et al. 2021). Sialate-O-acetylesterase, lipoprotein lipase, and other lipases exhibited higher abundance in enriched HMW than in DS, whereas PLBD2 was below the detection limit across all five mAbs and was present in trace levels in enriched HMW. The overall lipase level was less than 3 ppm in the five mAbs, thus indicating that the purification process effectively removed this group of HCPs.

Protease enzymatic activity is involved in proteolysis, and may induce the formation of small fragments and affect product quality. Cathepsin L1, which has been reported to induce fragmentation of mAb (Luo et al.), was detected at a significantly higher level in enriched HMW than DS in all five mAbs. Notably, the level of Cathepsin L1 in DS was less than 0.8 ppm in all mAb DS. Carboxypeptidase, another protease that cleaves both C-terminal lysine and arginine, was predominantly detected in enriched HMW for mAb2. Cathepsin D, which negatively affects product stability by causing mAb fragmentation and particle formation (Bee et al., 2015, *Biotechnol Prog,* 31(5):1360-1369), was not detectable in DS and was below 0.3 ppm in enriched HMW.

Previous studies have denoted the HCPs that escape multiple purification processes and are present in the final drug product as "hitch-hiker" proteins (Ranjan et al., 2019, *Biotechnol Bioeng,* 116(7):1684-1697). These HCPs are likely to have strong specific or nonspecific interactions with mAbs (Bee et al., 2017, *Biotechnol Prog,* 33(1):140-145) and cannot be removed by polishing steps based on their chemical properties. This disclosure demonstrates that certain HCPs are specifically or nonspecifically associated with mAb HMW species, because the abundance of HCP in enriched HMW was substantially higher than that in DS. In addition, these results indicate that the interaction between HCPs and HMW species is highly molecule-dependent, as the abundance of the same HCP differed among the different mAbs.

Example 9. Properties of Host Cell Proteins in Enriched HMW

Figure 41A:
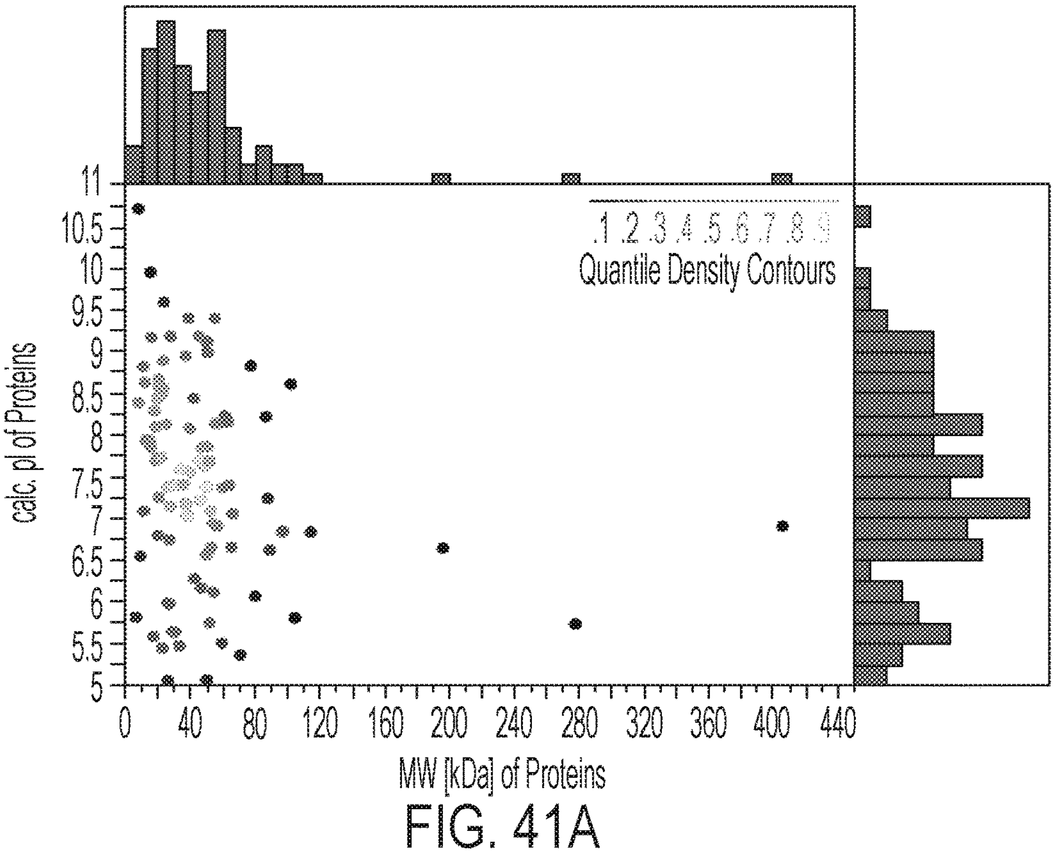
FIG. 41A shows a comparison of theoretical isoelectric points and molecular weight for all HCPs identified in five mAb DS samples, according to an exemplary embodiment.
Figure 41B:
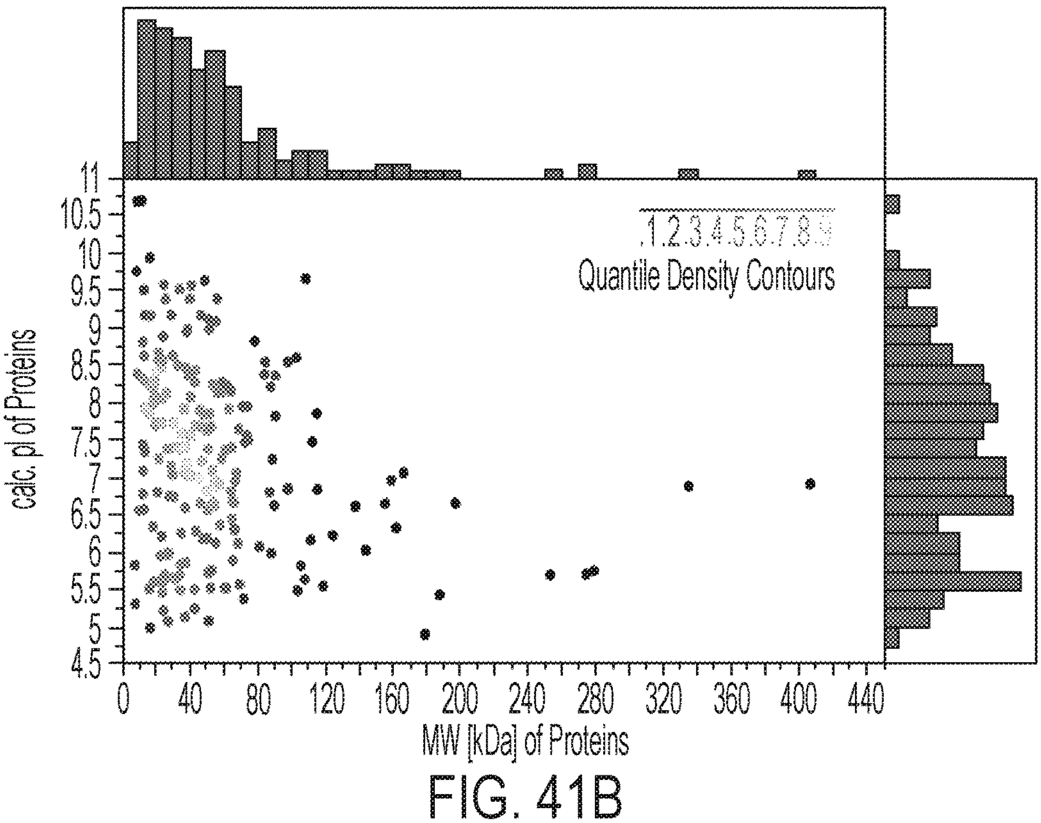
FIG. 41B shows a comparison of theoretical isoelectric points and molecular weight for all HCPs identified in five mAb enriched HMW samples, according to an exemplary embodiment.

Determining which specific properties of HCPs may contribute to enrichment in the high molecular weight fraction of a biotherapeutic product is important for informing process development. Thus, the predicted isoelectric point (pI) and molecular weight (MW) distributions of all HCPs across the analyzed enriched HMW of all five studied mAbs, shown in FIG. 41B, were compared with the properties of HCPs from DS of all five studied mAbs, shown in FIG. 41A. It was hypothesized that HCPs with high MW would coelute with HMW mAb species. However, most HCPs enriched in the HMW fraction had MWs between 10 kDa and 100 kDa, values lower than the MW of the mAbs. Therefore, a large proportion of HCPs were retained in the HMW fraction owing to the interactions with HMW mAb species rather than their own size. The pI distribution of HCPs identified from the HMW was comparable to that identified from the DS.

As stated earlier, C-C motif chemokine had the highest relative abundance in mAb2 and was 46 times more abundant in enriched HMW than DS. The C-C motif chemokine belongs to the chemokine family, and plays roles in immune and inflammatory responses. Based on the known features of this HCP and the measured abundance, it was determined that the relatively high level of C-C motif chemokine in mAb2 DS may be a safety concern. The chemical properties of C-C motif chemokine and detailed purification steps of mAb2 were reviewed to understand how this HCP was retained in the final DS.

C-C motif chemokine is a small HCP with a molecular weight of 15.8 kDa and an estimated pI of 9.16. The mAb was first purified by affinity chromatography, which captures mAb and washes out process impurity, and can effectively remove HCPs that are not bound to mAb or resin. In the following polishing step, the acidic HCPs in Protein A eluate will attach to the positively charged AEX ligand at neutral pH and be removed. The basic HCPs, such as C-C motif chemokine, are positively charged at neutral pH and coeluted with mAb in the flow-through mode of AEX purification. In the HIC purification step, highly hydrophobic impurities would bind to the column, while C-C motif chemokine is likely to flow through with mAb. Thus, the C-C motif chemokine can not be effectively removed by the conventional mAb purification steps based on its chemical properties if it is present in Protein A eluate. In the case of an HCP such as C-C motif chemokine, further analysis and potentially further purification steps may be necessary for optimal production of a biotherapeutic product.

Example 10. Comparing C-C Motif Chemokine in Dimer, vHMW and Enriched HMW from mAb1

The C-C motif chemokine had a higher abundance in mAb2 than in other products, thus demonstrating that the presence of this HCP was probably due to a specific interaction with mAb2 instead of the resin. Because the C-C motif chemokine was substantially more abundant in enriched HMW than DS, the association may occur between HMW species and this HCP. The HMW fraction contains heterogeneous species, including dimers and vHMW. In order to determine which particular HMW species are responsible for interaction with C-C motif chemokine, further studies were investigated using additional SEC fractionation of mAb2.

The mAb2 enriched HMW was further fractionated with another round of SEC to obtain enriched dimer and enriched vHMW fractions. The twenty most abundant HCPs identified from these three fractions are shown in FIG. 42. HCPs are listed in order of abundance in the enriched HMW of mAb2. The heatmap is colored by the HCP level, ranging from 0 ppm (blue, not detected) to more than 100 ppm (red).

A total of 123 HCPs were identified from the dimer fraction, compared with 110 and 102 HCPs in the enriched total HMW and vHMW fractions, respectively. The C-C motif chemokine abundance in all three HMW fractions was substantially higher than that in DS, and the levels varied across the fractions. The concentrations of C-C motif chemokine were 934.5 ppm, 1738.5 ppm, and 7733.9 ppm in the enriched vHMW, total HMW, and dimer fractions, respectively. The dimer fraction had the highest levels of C-C motif chemokine, at eight times that in enriched vHMW. Meanwhile, the C-C motif chemokine in the enriched vHMW fraction was almost half that in the enriched total HMW fraction. The findings indicated that C-C motif chemokine was most likely associated with dimers rather than vHMW species or total DS.

In addition to C-C motif chemokine, most HCPs detected, such as Carboxypeptidase and Beta-hexosaminidase, were specifically enriched in the dimer fraction. Other HCPs, such as Connective tissue growth factor, were substantially higher in the vHMW fraction than in the dimer fraction.

Example 11. SEC Fractionation and PRM Analysis

Figure 43:
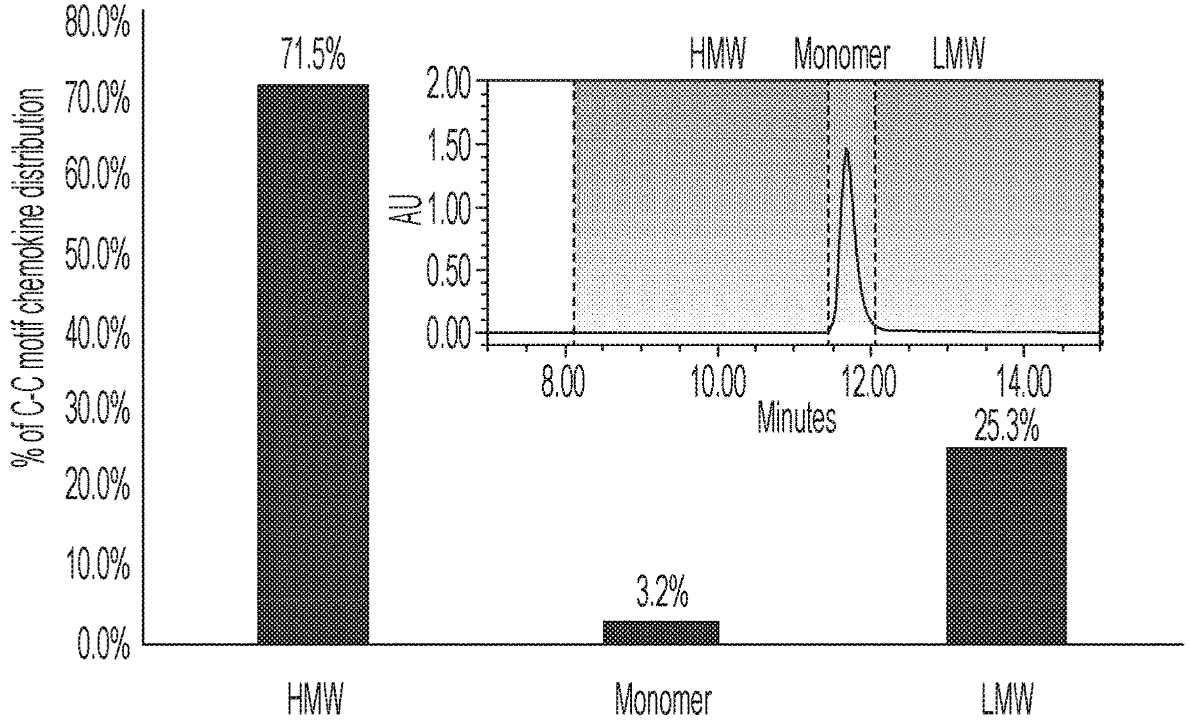
FIG. 43 shows a distribution of C-C motif chemokine in HMW, monomer, and LMW fractions of mAb2, according to an exemplary embodiment. The inset shows an SEC chromatogram indicating a HMW fraction, monomer fraction and LMW fraction of mAb2, according to an exemplary embodiment.

Because the C-C motif chemokine was enriched in the mAb2 HMW fraction, it was reasoned that removal of HMW species might facilitate the clearance of this HCP from the DS. To demonstrate this hypothesis, mAb2 DS was fractionated with SEC. HMW species, monomers, and LMW species were obtained after SEC fractionation, as shown in the inset of FIG. 43. The SEC fractions as well as the mAb2 DS were subjected to tryptic digestion and PRM analysis. The level of C-C motif chemokine was estimated by comparison to a spiked internal standard. The C-C motif chemokine distribution in different fractions is shown in FIG. 43.

Approximately 63.8 fmol C-C motif chemokine was present in unfractionated DS. After SEC column purification, the C-C motif chemokine level decreased to 2.4 fmol in the monomer fraction, representing 3.2% of the total C-C motif chemokine in the three fractions. Interestingly, the LMW fraction contained 25.3% of the C-C motif chemokine, which might have represented dissociated species. This finding indicated that, under SEC conditions, C-C motif chemokine is partially dissociated and exists in unbound form. The fraction volume collected for LMW was approximately six times higher than that of the monomers, and the C-C motif chemokine level was approximately eight times higher in LMW than in DS. The C-C motif chemokine present in mAb2 DS might have been the dissociated form after SEC fractionation. Despite the potential dissociation, most C-C motif chemokine levels were significantly enriched in the HMW fraction, at 53.2 fmol, or 71.5% of the total HCP.

These results demonstrate that HCPs present at a concerningly high abundance, such as C-C motif chemokine in mAb2 DS as shown in FIG. 40, may have particular interactions with HMW species such as antibody dimers, as shown in FIG. 42, and may thus be enriched in HMW fractions of the DS. Using SEC and LC-MS/MS, it is possible to assess the distribution and abundance of a problematic HCP, determine the specific antibody species responsible for the undesirable interaction, and to substantially remove the problematic HCP from the DS using SEC fractionation, as shown in FIG. 43. Therefore, this disclosure provides a novel method for improving production of a biotherapeutic product through specific removal of an HCP that may otherwise cause product instability or immunogenicity.

HMW species are product-related variants that may affect therapeutic protein product efficacy and safety. Immunogenicity assays have shown that the aggregates induce an immune response of FVIII (Reipert et al., 2007, *Br J Haematol,* 136(1):12-15; Purohit and Balasubramanian, 2008, *J Pharm Sci,* 95(2):358-371), recombinant human growth hormone (Fradkin and Randolph, 2009, *J Pharm Sci,* 98(9):3247-3264), and IgG (Joubert et al., 2012, *J Biol Chem,* 287(30):25266-25279). The mechanism through which HMW species cause immunogenicity remains unclear. The study described above demonstrates that high levels of HCPs may be present in the HMW fraction of biotherapeutic product DS. Therefore, immunogenicity may also be induced by the HCPs in addition to, or instead of, HMW therapeutic protein species themselves.

In this work, HCP analysis of SEC separated HMW fractions was performed. As with other chromatographic separation methods, the SEC fractionation of HMW resulted in detection of a higher number of HCPs. If appropriate, SEC can be incorporated as an alternative HCP enrichment strategy for HCP analysis to facilitate the detection of low abundance HCPs. Unlike HILIC chromatography, which denatures HCPs under a high organic gradient, SEC maintains the native status of HCPs and is easily coupled with native digestion. Thus, the detection sensitivity can be further improved by using native digestion after HCP enrichment.

Studying the associations between HCPs and mAbs is challenging because the levels of HCPs are very low with respect to those of the drug products. Previous studies have applied cross-interaction chromatography (Levy et al., 2013,

*Biotechnol Bioeng,* 111(5):904-912; Aboulaich et al., 2014, *Biotechnol Bioeng,* 30(5):1114-1124; Zhang et al., 2016, *Biotechnol Prog,* 32(3):708-717) or surface plasmon resonance (Bee et al. 2017) to determine the binding activity between mAbs and HCPs. The results described in the present disclosure indicate that the association between HCPs and HMW species might explain why certain HCPs are copurified with the DS. Although the interaction mechanism remains unclear, these findings suggest new directions for studying mAb and HCP associations. More importantly, removing HMW species from DS can significantly decrease the levels of certain HCPs and provide information to facilitate downstream purification process development. Thus, the present disclosure of HCP profiling of HMW species expands knowledge regarding the HCPs present in mAb preparations and their interaction mechanisms, aiding in the understanding of HMW species, immunogenicity, HCP identification, and HCP removal for overall development of therapeutic protein drugs.

What is claimed is:

1. A method for identifying host cell protein (HCP) impurities in a sample, comprising:

a) subjecting a sample including at least one protein of interest and at least one HCP impurity to size exclusion chromatography (SEC) analysis to produce fractions, wherein a mobile phase for said SEC analysis comprises about 12 mM sodium lauroyl sarcosinate and about 12 mM sodium deoxycholate;

b) subjecting said fractions to acid precipitation to produce detergent-depleted fractions, wherein said acid precipitation comprises contacting said fractions to about 1% trifluoroacetic acid;

c) subjecting said detergent-depleted fractions to buffer exchange to produce buffer-exchanged fractions;

d) subjecting said buffer-exchanged fractions to limited digestion to produce peptide digests, wherein said limited digestion comprises contacting said buffer-exchanged fractions to trypsin at an enzyme to protein ratio of between about 1:200 and about 1:2000; and e) subjecting said peptide digests to LC-MS analysis to identify said at least one HCP impurity.

2. The method of claim 1, wherein said at least one protein of interest is an antibody, a bispecific antibody, a monoclonal antibody, a fusion protein, an antibody-drug conjugate, an antibody fragment, or a protein pharmaceutical product.

3. The method of claim 1, wherein an amount of protein subjected to SEC is between about 0.5 mg and about 20 mg.

4. The method of claim 1, wherein an amount of protein subjected to SEC is about 10 mg.

5. The method of claim 1, wherein said fractions comprise a high molecular weight (HMW) fraction, a main fraction, and a low molecular weight (LMW) fraction.

6. The method of claim 5, wherein said fractions further comprise a tail fraction.

7. The method of claim 6, wherein said HMW fraction includes eluate of about 0.3 column volumes (CV) and about 5 milli absorbance units (mAU).

8. The method of claim 6, wherein said main fraction includes eluate between about 5 mAU and about 40 mAU.

9. The method of claim 6, wherein said tail fraction includes eluate between about 40 mAU and about 10 mAU.

10. The method of claim 6, wherein said LMW fraction includes eluate of about 10 mAU and about 1.1 CV.

11. The method of claim 6, wherein said tail fraction includes eluate between about 40 mAU and about 3 mAU.

12. The method of claim 6, wherein said LMW fraction includes eluate of about 3 mAU and about 1.1 CV.

13. The method of claim 1, wherein said LC-MS analysis comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

14. The method of claim 1, wherein said LC-MS analysis uses an electrospray ionization mass spectrometer, nano-electrospray ionization mass spectrometer, or an Orbitrap-based mass spectrometer, wherein said mass spectrometer is coupled to said liquid chromatography system.

15. The method of claim 1, wherein an amount of protein subjected to SEC is between about 1 mg and about 10 mg.

16. The method of claim 1, wherein an amount of protein subjected to SEC is between about 8 mg and about 12 mg.

17. The method of claim 1, wherein an amount of protein subjected to SEC is about 1 mg, about 5 mg, or about 20 mg.

18. A method for identifying host cell protein (HCP) impurities in a sample, comprising:

a) combining a sample including at least one protein of interest and at least one HCP impurity with a dissociation reagent to produce a first combination;

b) subjecting said first combination to acid precipitation to produce dissociation reagent-depleted fractions;

c) subjecting said dissociation reagent-depleted fractions to enzymatic digestion to produce peptide digests; and d) subjecting said dissociation reagent-depleted fractions to liquid chromatography-mass spectrometry analysis to identify said at least one HCP impurity.

19. The method of claim 18, wherein said enzymatic digestion is a limited digestion.

20. The method of claim 18, wherein said enzymatic digestion is performed by contacting said dissociation reagent-depleted fractions to trypsin.

21. The method of claim 18, wherein said enzymatic digestion is performed by contacting said dissociation reagent-depleted fractions to a digestive enzyme at an enzyme to protein ratio of between about 1:100 and about 1:2000.

22. The method of claim 21, wherein said enzyme to protein ratio is about 1:200.

23. The method of claim 18, further comprising desalting said peptide digests prior to the liquid chromatography-mass spectrometry analysis of step (d).

24. The method of claim 18, wherein said enzymatic digestion is performed by contacting said dissociation reagent-depleted fractions to a digestive enzyme at an enzyme to protein ratio of about 1:100, about 1:300, about 1:400, about 1:500, about 1:1000, or about 1:2000.

25. The method of claim 18, wherein a concentration of said at least one surfactant is between about 20 mM and about 120 mM.

26. A method for identifying host cell protein (HCP) impurities in a sample, comprising:

a) combining a sample including at least one protein of interest and at least one HCP impurity with a dissociation reagent to produce a first combination;

b) subjecting said first combination to acid precipitation to produce dissociation reagent- depleted fractions;

c) subjecting said dissociation reagent-depleted fractions to buffer exchange to produce buffer-exchanged fractions;

d) subjecting said buffer-exchanged fractions to enzymatic digestion to produce peptide digests; and e) subjecting said peptide digests to liquid chromatography-mass spectrometry analysis to identify said at least one HCP impurity.

27. The method of claim 26, wherein said at least one protein of interest is an antibody, a bispecific antibody, a monoclonal antibody, a fusion protein, an antibody-drug conjugate, an antibody fragment, or a protein pharmaceutical product.

28. The method of claim 26, wherein said dissociation reagent is at least one surfactant.

29. The method of claim 28, wherein a concentration of said at least one surfactant is about 20 mM, about 40 mM, about 60 mM, about 100 mM, or about 120 mM.

30. The method of claim 28, further comprising incubating said first combination for about 5 minutes, about 15 minutes, about 30 minutes, about 60 minutes, about 90 minutes, or about 120 minutes prior to the acid precipitation of step (b).

31. The method of claim 28, wherein said at least one surfactant is a detergent.

32. The method of claim 31, wherein said at least one detergent is sodium deoxycholate, wherein a concentration of sodium deoxycholate is about 20 mM, about 40 mM, about 60 mM, about 100 mM, or about 120 mM.

33. The method of claim 31, wherein said enzymatic digestion is performed by contacting said fractions to a digestive enzyme at an enzyme to protein ratio of between about 1:200 and about 1:2000.

34. The method of claim 26, wherein said at least one detergent is sodium lauroyl sarcosinate, wherein a concentration of sodium lauroyl sarcosinate is about 20 mM, about 40 mM, about 60 mM, about 100 mM, or about 120 mM.

35. The method of claim 31, wherein said at least one detergent is sodium lauroyl sarcosinate, wherein a concentration of sodium lauroyl sarcosinate is between about 20 mM-and about 120 mM.

36. The method of claim 31, wherein said at least one detergent is sodium deoxycholate and sodium lauroyl sarcosinate, wherein a concentration of sodium deoxycholate is between about 20 mM and about 120 mM, and a concentration of sodium lauroyl sarcosinate is between about 20 mM and about 120 mM.

37. The method of claim 31, wherein said at least one detergent is sodium deoxycholate, wherein a concentration of sodium deoxycholate is between about 20 mM and about 120 mM.

38. The method of claim 31, wherein said at least one detergent is selected from a group consisting of sodium deoxycholate, sodium lauroyl sarcosinate and a combination thereof.

39. The method of claim 38, wherein said first combination is incubated for between about 5 minutes and about 120 minutes prior to the acid precipitation of step (b).

40. The method of claim 31, wherein said at least one detergent is sodium deoxycholate and sodium lauroyl sarcosinate, wherein a concentration of sodium deoxycholate is about 20 mM, about 40 mM, about 60 mM, about 100 mM, or about 120 mM, and a concentration of sodium lauroyl sarcosinate is about 20 mM, about 40 mM, about 60 mM, about 100 mM, or about 120 mM.

41. The method of claim 26, wherein said enzymatic digestion is a limited digestion.

42. The method of claim 26, wherein said enzymatic digestion is performed by contacting said fractions to trypsin.

43. The method of claim 26, wherein said enzymatic digestion is performed by contacting said fractions to a digestive enzyme at an enzyme to protein ratio of between about 1:100 and about 1:2000.

44. The method of claim 43, wherein said enzyme to protein ratio is about 1:200.

45. The method of claim 26, further comprising desalting said peptide digests prior to the liquid chromatography-mass spectrometry analysis of step (e).

46. The method of claim 26, wherein said acid precipitation is incubated for between about 5 minutes and about 60 minutes.

47. The method of claim 26, wherein said acid precipitation comprises contacting said first combination to between about 2.5% and about 10% trifluoroacetic acid.

48. The method of claim 26, wherein said liquid chromatography comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

49. The method of claim 26, wherein said enzymatic digestion is performed by contacting said fractions to a digestive enzyme at an enzyme to protein ratio of about 1:100, about 1:300, about 1:400, about 1:500, about 1:1000, or about 1:2000.

50. The method of claim 26, further comprising incubating said acid precipitation for about 5 minutes or about 60 minutes.

51. The method of claim 26, wherein said acid precipitation comprises contacting said first combination to about 2.5% trifluoroacetic acid, about 5% trifluoroacetic acid, about 7.5% trifluoroacetic acid, or about 10% trifluoroacetic acid.

52. The method of claim 26, wherein said acid precipitation comprises contacting said first combination to about 2.5% trifluoroacetic acid, about 5% trifluoroacetic acid, about 7.5% trifluoroacetic acid, or about 10% trifluoroacetic acid.

* * * * *